(12) United States Patent
Tran et al.

(10) Patent No.: US 12,163,964 B2
(45) Date of Patent: *Dec. 10, 2024

(54) AMYLOID BETA DETECTION BY MASS SPECTROMETRY

(71) Applicant: QUEST DIAGNOSTICS INVESTMENTS LLC, Madison, NJ (US)

(72) Inventors: Diana Tran, Garden Grove, CA (US); Darren Weber, Rancho Santa Margarita, CA (US); Nigel Clarke, Vista, CA (US)

(73) Assignee: QUEST DIAGNOSTIC INVESTMENTS LLC, Madison, NJ (US)

(*) Notice: Subject to any disclaimer, the term of this patent is extended or adjusted under 35 U.S.C. 154(b) by 11 days.

This patent is subject to a terminal disclaimer.

(21) Appl. No.: 17/839,262

(22) Filed: Jun. 13, 2022

(65) Prior Publication Data

US 2022/0349897 A1 Nov. 3, 2022

Related U.S. Application Data

(63) Continuation of application No. 15/277,879, filed on Sep. 27, 2016, now Pat. No. 11,360,098.

(60) Provisional application No. 62/277,772, filed on Jan. 12, 2016, provisional application No. 62/234,027, filed on Sep. 28, 2015.

(51) Int. Cl.
*G01N 31/00* (2006.01)
*G01N 33/53* (2006.01)
*G01N 33/68* (2006.01)

(52) U.S. Cl.
CPC ..... *G01N 33/6848* (2013.01); *G01N 33/6827* (2013.01); *G01N 2333/4709* (2013.01); *G01N 2800/2814* (2013.01); *G01N 2800/2821* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,774,175 A | 9/1988 | Chang et al. |
| 11,360,098 B2* | 6/2022 | Tran .................. G01N 33/6848 |
| 11,391,744 B2 | 7/2022 | Miller-Jones et al. |
| 2004/0096907 A1 | 5/2004 | Bohrmann et al. |
| 2007/0225209 A1 | 9/2007 | Roch et al. |
| 2009/0134325 A1 | 5/2009 | Goldman et al. |
| 2009/0155766 A1 | 6/2009 | Goldman et al. |
| 2010/0285467 A1 | 11/2010 | Lohse et al. |
| 2013/0137120 A1 | 5/2013 | Nanjoh et al. |

FOREIGN PATENT DOCUMENTS

| | | |
|---|---|---|
| AU | 2014265047 A1 | 12/2014 |
| CN | 101048662 A | 10/2007 |
| CN | 101196526 A | 6/2008 |
| CN | 101946005 A | 1/2011 |
| CN | 102439451 A | 5/2012 |
| CN | 102596230 A | 7/2012 |
| CN | 104797715 A | 7/2015 |
| JP | 2005517517 A | 6/2005 |
| JP | 2012511154 A | 5/2012 |
| JP | 2013541718 A | 11/2013 |
| JP | 2015505365 A | 2/2015 |
| WO | 2007011639 A2 | 1/2007 |
| WO | 2010141421 A1 | 12/2010 |
| WO | 2011092796 A1 | 8/2011 |
| WO | 2014047316 A1 | 3/2014 |

OTHER PUBLICATIONS

Paraschiv et al. J. Mol. Recognit. 2013: 26: pp. 1-9 (Year: 2013).*
Abraham C.R., et al., "Immunochemical Identification of the Serine Protease Inhibitor α1-Antichymotrypsin in the Brain Amyloid Deposits of Alzheimer's Disease", Cell, Elsevier, Feb. 1988, vol. 52(4), pp. 487-501.
Bros P., et al., "Quantitative Detection of Amyloid Beta Peptides by Mass Spectrometry: State of the Art and Clinical Applications," Clinical Chemistry and Laboratory Medicine, Feb. 2015, vol. 53 (10), pp. 1483-1493.
Cerf E., et al., "High Ability of Apolipoprotein E4 to Stabilize Amyloid-Beta Peptide Oligomers, the Pathological Entities Responsible for Alzheimer's Disease", The Faseb Journal, vol. 25(5), May 2011, pp. 1585-1595.
Extended European Search Report for Application No. 16852474.2, mailed on Jul. 17, 2019.
Final Office Action mailed Jan. 9, 2020 for U.S. Appl. No. 15/277,879, filed Sep. 27, 2016.
Final Office Action mailed Jul. 24, 2020 for U.S. Appl. No. 15/277,879, filed Sep. 27, 2016.
Goda et al., "Evaluation of Peptide Adsorption-Controlled Liquid Chromatography-Tandem Mass Spectrometric (PAC-LC-MS/MS) Method for Simple and Simultaneous Quantitation of Amyloid B 1-38, 1-40, 1-42 and 1-43 Peptides in Dog Cerebrospinal Fluid" Journal of Chromatography B, 2012, vols. 895-896, pp. 137-145.
Guntert A., et al., "High Sensitivity Analysis of Amyloid-Beta Peptide Composition in Amyloid Deposits From Human and PS2APP Mouse Brain," Neuroscience, 2006, vol. 143, pp. 461-475.
International Search and Written Opinion Report for Application No. PCT/US2016/054148, mailed on Dec. 8, 2016, 13 pages.

(Continued)

*Primary Examiner* — Lisa V Cook
(74) *Attorney, Agent, or Firm* — Foley & Lardner LLP

(57) ABSTRACT

Provided are methods for the detection or quantitation of amyloid beta. In a particular aspect, provided herein are methods for detecting amyloid beta or fragments thereof by mass spectrometry. In another aspect, provided herein are methods for determining the ratio of amyloid beta 42 (Aβ42) to amyloid beta 40 (Aβ40). In another aspect, provided herein are methods for diagnosis or prognosis of Alzheimer's disease or dementia.

27 Claims, 17 Drawing Sheets

Specification includes a Sequence Listing.

(56) References Cited

OTHER PUBLICATIONS

Janelidze S., et al., "CSF A beta 42/40 and A beta 42/38 Ratios by prm Mass Spectrometry or Elisa: Improved Biomarkers of Alzheimer's Disease," Alzheimer's & Dementia, Jul. 2015, vol. 11 (7), pp. P866.

Kim et al., "Detection and Quantification of Plasma Amyloid Beta by Selected Reaction Monitoring Mass Spectrometry," Analytica Chimica Acta, 2014, vol. 840, pp. 1-9.

Lame et al., "Quantitation of Amyloid Beta Peptides Amyloid Beta 1-38, Amyloid Beta 1-40, and Amyloid Beta 1-42 in Human Cerebrospinal Fluid by Ultra-Performance Liquid Chromatography-Tandem Mass Spectrometry" Analytical Biochemistry, 2011, vol. 419, pp. 133-139.

Murphy M.P., et al., "Alzheimer's Disease and the Amyloid-Beta Peptide," Journal of Alzheimer's Disease, 2010, vol. 19 (1), 17 pages.

Non-Final Office Action mailed Apr. 4, 2019 for U.S. Appl. No. 15/277,879, filed Sep. 27, 2016.

Non-Final Office Action mailed May 27, 2021 for U.S. Appl. No. 15/277,879, filed Sep. 27, 2016.

Oe T., et al., "Quantitative Analysis of Amyloid Beta Peptides in Cerebrospinal Fluid of Alzheimer's Disease Patients by Immunoaffinity Purification and Stable Isotope Dilution Liquid Chromatography/ negative Electrospray Ionization Tandem Mass Spectrometry", Rapid Communications in Mass Spectrometry, John Wiley & Sons, GB, 2006, vol. 20 (24), pp. 3723-3735.

Pica-Mendez Am., et al., "Nonspecific Binding of A(Beta)42 to Polypropylene Tubes and the Effect of Tween-20", Clinica Chimica Acta, Elsevier BV, Amsterdam, NI, vol. 411(21-22), Nov. 2010, p. 1833.

Qiu T., et al., "AB42 and AB40: Similarities and Differences," Special Issue: 13th Chinese International Peptide Symposium, Jul. 2015, vol. 21 (7), pp. 522-529. (Abstract Only).

Tran D., et al., "Cerebrospinal Fluid Beta-Amyloid 40 and 42 Quantitation Using a Novel Stabilization Technique", Alzheimer's & Dementia, The Journal of the Alzheimer's Association, vol. 12(7), Jul. 2016, p. P555.

Lai et al., "A Combined Tryptic Peptide and Winged Peptide Internal Standard Approach for the Determination of a-lactalbumin in Dairy Products by Ultra High Performance Liquid Chromatography With Tandem Mass Spectrometry," Journal of Separation Science, 2015, vol. 38 (10), pp. 1800-1806.

Bilkova Z., et al., "Epitope Extraction Technique Using a Proteolytic Magnetic Reactor Combined With Fourier-transform Ion Cyclotron Resonance Mass Spectrometry as a Tool for the Screening of Potential Vaccine Lead Peptides," European Journal of Mass Spectrometry, Jan. 2005, vol. 11 (5), pp. 489-495, XP009084150, ISSN: 1469-0667, DOI: 10.1255/ejms.782.

Bilkova Z., et al., "Functionalized Magnetic Micro- and Nanoparticles: Optimization and Application to Micro-chip Tryptic Digestion," Electrophoresis, Apr. 2006, vol. 27 (9), pp. 1811-1824, XP071498453, ISSN: 0173-0835, DOI: 10.1002/elps.200500587.

Extended European Search Report for Application No. 23187203.7, mailed on Dec. 13, 2023, 10 Pages.

Inoue K., et al., "Liquid Chromatography/tandem Mass Spectrometry Characterization of Oxidized Amyloid Beta Peptides as Potential Biomarkers of Alzheimer's Disease," Rapid Communications in Mass Spectrometry, 2006, vol. 20(5), pp. 911-918. DOI: 10.1002/rcm.2395, [retrieved on Sep. 12, 2016] Retrieved from the Internet:[URL:https://analyticalsciencejournals.onlinelibrary.wiley.com/doi/epdf/10.1002/rcm.2395pdf].

Iurascu M.I., et al., "Structural Characterization of Beta-amyloid Oligomer-aggregates by Ion Mobility Mass Spectrometry and Electron Spin Resonance Spectroscopy," Analytical and Bioanalytical Chemistry, Dec. 2009, vol. 395 (8), pp. 2509-2519, XP019756706, ISSN: 1618-2650, DOI: 10.1007/s00216-009-3164-3.

Leinenbach A., et al., "Mass Spectrometry-Based Candidate Reference Measurement Procedure for Quantification of Amyloid-[beta] in Cerebrospinal Fluid," Clinical Chemistry, Jul. 2014, vol. 60(7), pp. 987-994, XP093105387, US ISSN: 0009-9147, DOI: 10.1373/clinchem.2013.220392.

Paraschiv G., et al., "Epitope Structure and Binding Affinity of Single Chain Llama Anti-[beta]-Amyloid Antibodies Revealed by Proteolytic Excision Affinity-mass Spectrometry," Journal of Molecular Recognition, Dec. 2012, vol. 26 (1), pp. 1-9, XP055109718, ISSN: 0952-3499, DOI: 10.1002/jmr.2210.

\* cited by examiner

FIGURE 1

Intact Aβ40 Sequence:

DAEFRHDSGYEVHHQKLVFFAEDVGSNKGAIIGLMVGGVV (SEQ ID NO:1)

Novel Aβ40 peptide monitored:

GAIIGLMVGGVV (SEQ ID NO:2)

Intact Aβ42 Sequence:

DAEFRHDSGYEVHHQKLVFFAEDVGSNKGAIIGLMVGGVVIA (SEQ ID NO:3)

Novel Aβ40 peptide monitored:

GAIIGLMVGGVVIA (SEQ ID NO:4)

FIGURE 11

| C8--100uL injection | Peak Area | Peak Area for 230uL Injection | Peak Area at 0.1ng/mL |
|---|---|---|---|
| 2ug Lysyl 4hour digest Microwave | 5016956 | 11538999 | 5769 |
| 4ug Lysyl 4hour digest Microwave | 5262118 | 12102870 | 6051 |
| 2ug Lysyl 4hour digest Microwave 1--1 freeze/thaw | 5074484 | 11671313 | 5836 |
| 4ug Lysyl 4hour digest Microwave 1--1 freeze/thaw | 6200526 | 14261209 | 7131 |

| C4 Column--50uL injection | Peak Area | Peak Area for 230uL Injection | Peak Area at 0.1ng/mL |
|---|---|---|---|
| 2ug Lysyl 4hour digest Microwave | 5869870 | 27001402 | 13501 |
| 4ug Lysyl 4hour digest Microwave | 6433642 | 29594753 | 14797 |
| 2ug Lysyl 4hour digest Microwave 1--1 freeze/thaw | 4917759 | 22621691 | 11311 |
| 4ug Lysyl 4hour digest Microwave 1--1 freeze/thaw | 7585102 | 34891469 | 17446 |

SEQUENCE LISTING

```
<160> NUMBER OF SEQ ID NOS: 4

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 12
<212> TYPE: PRT
<213> ORGANISM: Homo sapiens

<400> SEQUENCE: 2

Gly Ala Ile Ile Gly Leu Met Val Gly Gly Val Val
1               5                   10

<210> SEQ ID NO 3
<211> LENGTH: 42
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 4
<211> LENGTH: 14
<212> TYPE: PRT
<213> ORGANISM: Homo sapiens

<400> SEQUENCE: 4

Gly Ala Ile Ile Gly Leu Met Val Gly Gly Val Val Ile Ala
1               5                   10
```

AMYLOID BETA DETECTION BY MASS SPECTROMETRY

CROSS-REFERENCE TO RELATED PATENT APPLICATIONS

This application in a continuation application of U.S. patent application Ser. No. 15/277,879, filed Sep. 27, 2016, now U.S. Pat. No. 11,360,098, which claims benefit of U.S. Provisional Application No. 62/234,027, filed Sep. 28, 2015, and U.S. Provisional Application No. 62/277,772, filed Jan. 12, 2016, each of which is incorporated by reference herein in its entirety.

FIELD OF THE INVENTION

The invention relates to the detection or quantitation of amyloid beta. In a particular aspect, the invention relates to methods for detecting amyloid beta or fragments thereof by mass spectrometry.

BACKGROUND OF THE INVENTION

Alzheimer's disease is the most common form of dementia affecting the elderly population. Alzheimer's disease is characterized by a progressive decay of cognitive abilities, in particular, memory and learning. One of the hallmarks of the disease is neuritic plaques composed of amyloid beta (Aβ or Abeta) peptides.

The accuracy and sensitivity of current clinical diagnostic methods to predict or diagnose Alzheimer's disease is low Immunoassays are currently offered to detect amyloid beta, which is a biomarker predictive of progression to Alzheimer's disease. However, inter-laboratory variations in the results observed with currently available immunoassays are of concern.

An accurate and sensitive assay for detecting amyloid beta is needed.

SUMMARY OF THE INVENTION

Provided herein are methods for detecting or determining the amount of amyloid beta (Aβ) in a sample by mass spectrometry, including tandem mass spectrometry.

In certain embodiments, the methods provided herein for determining the amount of amyloid beta comprises (a) purifying amyloid beta in the sample; (b) ionizing amyloid beta in the sample; and (c) determining the amount of the amyloid beta ion(s) by mass spectrometry; wherein the amount of the amyloid beta ion(s) is related to the amount of amyloid beta in the sample.

In certain embodiments, the methods provided herein for determining the amount of amyloid beta comprises (a) purifying amyloid beta in the sample; (b) ionizing amyloid beta in the sample to produce a precursor ion of amyloid beta; (c) generating one or more fragment ions of amyloid beta; and (d) determining the amount of the ion(s) from step (c) or (d) or both by mass spectrometry; wherein the amount of the amyloid beta ion(s) is related to the amount of amyloid beta in the sample.

In certain embodiments, the methods provided herein for determining the amount of amyloid beta comprises (a) digesting amyloid beta in the sample to generate one or more fragments of amyloid beta; (b) purifying the one or more amyloid beta fragments; (c) ionizing the one or more amyloid beta fragments to produce a precursor ion; (d) generating one or more fragment ions; and (e) determining the amount of the ion(s) from step (c) or (d) or both by mass spectrometry; wherein the amount of the ion(s) is related to the amount of amyloid beta fragment(s) in the sample.

In certain embodiments, provided herein are methods for determining the amount of amyloid beta 42 (Aβ42). In some embodiments, the Aβ42 fragment comprises the sequence GAIIGLMVGGVVIA (SEQ ID NO:4). In some embodiments, the methods comprise (a) digesting amyloid beta in the sample to generate amyloid beta 42 (Aβ42); (b) purifying Aβ42; (c) ionizing Aβ42 to produce a precursor ion; (d) generating one or more fragment ions of Aβ42; and (e) determining the amount of the ion(s) from step (c) or (d) or both by mass spectrometry; wherein the amount of the ion(s) is related to the amount of Aβ42 in the sample.

In certain embodiments, provided herein are methods for determining the amount of amyloid beta 40 (Aβ40). In some embodiments, the Aβ40 fragment comprises the sequence GAIIGLMVGGVV (SEQ ID NO:2). In some embodiments, the methods comprise (a) digesting amyloid beta in the sample to generate amyloid beta 40 (Aβ40); (b) purifying Aβ40; (c) ionizing Aβ40 to produce a precursor ion; (d) generating one or more fragment ions of Aβ40; and (e) determining the amount of the ion(s) from step (c) or (d) or both by mass spectrometry; wherein the amount of the ion(s) is related to the amount of Aβ40 in the sample.

In certain embodiments, provided herein are methods for determining the amount of amyloid beta 42 (Aβ42) and amyloid beta 40 (Aβ40). In some embodiments, the methods comprise (a) digesting amyloid beta in the sample to generate amyloid beta 42 (Aβ42) and amyloid beta 40 (Aβ40); (b) purifying Aβ42 and Aβ40; (c) ionizing Aβ42 and Aβ40 to produce precursor ions; (d) generating one or more fragment ions of Aβ42 and Aβ40; and (e) determining the amount of the ion(s) from step (c) or (d) or both by mass spectrometry; wherein the amount of the ion(s) is related to the amount of Aβ42 and Aβ40 in the sample.

In certain embodiments, provided herein are methods for determining the ratio of amyloid beta 42 (Aβ42) to amyloid beta 40 (Aβ40). In some embodiments, the methods comprise (a) digesting amyloid beta in the sample to generate amyloid beta 42 (Aβ42) and amyloid beta 40 (Aβ40); (b) purifying Aβ42 and Aβ40; (c) ionizing Aβ42 and Aβ40 to produce precursor ions; (d) generating one or more fragment ions of Aβ42 and Aβ40; and (e) determining the amount of the ion(s) from step (c) or (d) or both by mass spectrometry; and (f) determining the ratio of Aβ42 to Aβ40. In some embodiments, the methods comprise determining the ratio of Aβ40 to Aβ42.

In certain embodiments, provided herein are methods for diagnosis or prognosis of Alzheimer's disease or dementia, the method comprising determining the amount of amyloid beta in a test sample by mass spectrometry; wherein an abnormal levels of amyloid beta is predictive or diagnostic of Alzheimer's disease. In some embodiments, the methods may include: (a) purifying amyloid beta in the sample; (b) ionizing amyloid beta in the sample; and (c) determining the amount of the amyloid beta ion(s) by mass spectrometry; and (d) the amount of the amyloid beta ion(s) is related to the amount of amyloid beta in the sample; wherein the abnormal levels of amyloid beta is predictive or diagnostic of Alzheimer's disease. In some embodiments, the methods comprise determining the ratio of amyloid beta fragments. In some embodiments, the methods comprise determining the ratio of amyloid beta 42 (Aβ42) to amyloid beta 40 (Aβ40). In some embodiments, the methods comprise determining the ratio of amyloid beta 42 (Aβ40) to amyloid beta 40 (Aβ42).

In certain embodiments, the methods provided herein comprise pretreating surfaces of equipment that come in contact with the sample. In some embodiments, the pretreatment comprises pre-coating the surfaces of equipment with an agent that prevents amyloid beta or fragments thereof from sticking to the surfaces. In some embodiments, the pretreatment comprises bacterial lysate pretreatment. In some embodiments, the pretreatment comprises *E. coli* lysate pretreatment. In some embodiments, the *E. coli* lysate comprises a trypsin-digested *E. coli* lysate. In some embodiments, the pretreated equipment includes, but not limited to, test tubes or plates, pipette tips, sample preparation apparatus, liquid chromatography apparatus, and mass spectrometry apparatus.

In certain embodiments, the methods provided herein comprise treating or incubating the sample with an agent that stabilizes amyloid beta or fragments thereof. In some embodiments, the methods provided herein comprise treating or incubating the sample with an amyloid beta antibody. In some embodiments, the methods provided herein comprise treating or incubating the sample with at least two distinct amyloid beta antibodies. In some embodiments, the amyloid beta antibody comprises an antibody that binds to the C-terminus of amyloid beta. In some embodiments, the amyloid beta antibody comprises an antibody that binds to the N-terminus of amyloid beta. In some embodiments, the agent that stabilizes amyloid beta comprises an apolipoprotein. In some embodiments, the agent that stabilizes amyloid beta comprises apolipoprotein E2. In some embodiments, the agent that stabilizes amyloid beta comprises apolipoprotein E4. In some embodiments, the agent that stabilizes amyloid beta comprises an antibody that binds to the C-terminus of amyloid beta, an antibody that binds to the N-terminus of amyloid beta, apolipoprotein E2, apolipoprotein E4, or a combination thereof. In some embodiments, the agent that stabilizes amyloid beta provided herein confers stability for at least 1 month at −70° C. In some embodiments, the agent that stabilizes amyloid beta provided herein confers stability for at least 2 months at −70° C. In some embodiments, the agent that stabilizes amyloid beta provided herein confers stability for at least 3 months at −70° C. In some embodiments, the agent that stabilizes amyloid beta provided herein confers stability through a freeze-thaw cycle. In some embodiments, the agent that stabilizes amyloid beta provided herein confers stability through at least two freeze-thaw cycles. In some embodiments, the agent that stabilizes amyloid beta provided herein confers stability through at least three freeze-thaw cycles. In some embodiments, the agent that stabilizes amyloid beta provided herein confers stability through at least four freeze-thaw cycles.

In certain embodiments, the methods provided herein comprise digesting amyloid beta in the sample. In some embodiments, the methods provided herein comprise digesting amyloid beta with an enzyme. In some embodiments, the enzyme is Lys-C. In some embodiments, the methods provided herein comprise digesting amyloid beta with urea. In some embodiments, the urea is in a concentration suitable for protein digestion. In some embodiments, the urea is 6M urea. In some embodiments, the methods provided herein comprise digesting amyloid beta with urea and Lys-C. In some embodiments, the digestion comprises digesting in conditions that reduce digestion time or increase digestion efficiency. In some embodiments, the digestion comprises digesting in microwave. In some embodiments, the methods provided herein comprise determining the amount of digested amyloid beta.

In certain embodiments, the methods provided herein comprise an extraction. In some embodiments, the methods provided herein comprise a mixed mode anion exchange extraction. In some embodiments, the methods provided herein comprise a solid phase extraction.

In certain embodiments, the methods provided herein comprise eluting and drying the sample using heated nitrogen. In some embodiments, the sample is resuspended in a reconstitution buffer.

In certain embodiments, the purifying the sample comprises a liquid chromatography. In some embodiments, liquid chromatography includes, but not limited to, reverse phase liquid chromatography (RPLC), high performance liquid chromatography (HPLC), and high turbulence liquid chromatography (HTLC). In a preferred embodiment, liquid chromatography comprises HPLC. In some embodiments, HPLC column typically includes a medium (i.e., a packing material) to facilitate separation of chemical moieties (i.e., fractionation). Suitable columns may include C-4, C-8, C-12, or C-18 columns. In a preferred embodiment, a suitable HPLC column is C-4 column.

In certain embodiments, the methods provided herein comprise using equipment that reduces sticking of amyloid beta to the surfaces of equipment. In some embodiments, the equipment comprises PEEK (poly ether ether ketone) tubing or apparatus. In some embodiments, the equipment comprises metal tubing or apparatus.

In certain embodiments, the methods provided herein comprise tandem mass spectrometry. In some embodiments, the methods provided herein comprise ionizing in positive mode. In some embodiments, the methods provided herein comprise ionizing in negative mode. In some embodiments, the methods provided herein comprise ionizing using heated electrospray ionization (HESI). In some embodiments, the methods provided herein comprise ionizing using electrospray ionization (ESI). In some embodiments, the methods provided herein comprise ionizing using atmospheric pressure chemical ionization (APCI). In a preferred embodiment, the methods provided herein comprise ionizing using heated electrospray ionization (HESI) in positive mode. In some embodiments, the collision energy is between 5V to 60V. In some embodiments, the collision energy is between 10V to 50V. In some embodiments, the collision energy is between 20V to 50V. In some embodiments, the collision energy is between 20V to 45V.

In certain embodiments, the methods provided herein comprise detecting or determining the amount of amyloid beta 40 (Aβ40). In some embodiments, Aβ40 comprises the sequence DAEFRHDSGYEVHHQKLVFFAEDVGSNK-GAIIGLMVGGVV (SEQ ID NO:1). In some embodiments, the methods provided herein comprise detecting or determining the amount of a fragment of Aβ40. In some embodiments, the Aβ40 fragment comprises the sequence GAIIGLMVGGVV (SEQ ID NO:2). In some embodiments, the Aβ40 fragment comprises a sequence containing an N-terminal or C-terminal winged peptide. In some embodiments, the Aβ40 fragment comprises SEQ ID NO:2 and an N-terminal or C-terminal winged peptide. In some embodiments, the winged peptide is hydrophilic. In some embodiments, the winged peptide comprises at least one amino acid. In some embodiments, the winged peptide comprises at least two amino acids. In some embodiments, the winged peptide comprises at least three amino acids. In some embodiments, the winged peptide comprises at least four amino acids. In some embodiments, the winged peptide comprises at least five amino acids. In some embodiments, the winged peptide comprises at least six amino acids. In some embodiments, the amount of the Aβ40 fragment correlates to the amount of Aβ40 in the sample.

In certain embodiments, the methods provided herein comprise detecting or determining the amount of amyloid beta 42 (Aβ42). In some embodiments, Aβ42 comprises the sequence DAEFRHDSGYEVHHQKLVFFAEDVGSNK-GAIIGLMVGGVVIA (SEQ ID NO:3). In some embodiments, the methods provided herein comprise detecting or determining the amount of a fragment of Aβ42. In some embodiments, the Aβ42 fragment comprises the sequence GAIIGLMVGGVVIA (SEQ ID NO:4). In some embodiments, the Aβ42 fragment comprises a sequence containing an N-terminal or C-terminal winged peptide. In some embodiments, the Aβ42 fragment comprises SEQ ID NO:4 and an N-terminal or C-terminal winged peptide. In some embodiments, the winged peptide is hydrophilic. In some embodiments, the winged peptide comprises at least one amino acid. In some embodiments, the winged peptide comprises at least two amino acids. In some embodiments, the winged peptide comprises at least three amino acids. In some embodiments, the winged peptide comprises at least four amino acids. In some embodiments, the winged peptide comprises at least five amino acids. In some embodiments, the winged peptide comprises at least six amino acids. In some embodiments, the amount of the Aβ42 fragment correlates to the amount of Aβ42 in the sample.

In certain embodiments, the methods provided herein comprise detecting or determining the ratio of Aβ40 to Aβ42 (Aβ40:Aβ42). In some embodiments, the methods provided herein comprise detecting or determining the ratio of the Aβ40 fragment to the Aβ42 fragment (Aβ40 fragment:Aβ42 fragment). In some embodiments, the methods provided herein comprise detecting or determining the ratio of Aβ42 to Aβ40 (Aβ42:Aβ40). In some embodiments, the methods provided herein comprise detecting or determining the ratio of the Aβ42 fragment to the Aβ40 fragment (Aβ42 fragment: Aβ40 fragment).

In certain embodiments, the ratio of Aβ42 to Aβ40, or the ratio of the Aβ42 fragment to the Aβ40 fragment, of 0.6 or less is predictive or diagnostic of Alzheimer's disease. In some embodiments, the ratio of Aβ42 to Aβ40, or the ratio of the Aβ42 fragment to the Aβ40 fragment, of 0.5 or less is predictive or diagnostic of Alzheimer's disease. In some embodiments, the ratio of Aβ42 to Aβ40, or the ratio of the Aβ42 fragment to the Aβ40 fragment, of 0.45 or less is predictive or diagnostic of Alzheimer's disease. In some embodiments, the ratio of Aβ42 to Aβ40, or the ratio of the Aβ42 fragment to the Aβ40 fragment, of 0.4 or less is predictive or diagnostic of Alzheimer's disease. In some embodiments, the ratio of Aβ42 to Aβ40, or the ratio of the Aβ42 fragment to the Aβ40 fragment, of 0.35 or less is predictive or diagnostic of Alzheimer's disease. In some embodiments, the ratio of Aβ42 to Aβ40, or the ratio of the Aβ42 fragment to the Aβ40 fragment, of 0.3 or less is predictive or diagnostic of Alzheimer's disease. In some embodiments, the ratio of Aβ42 to Aβ40, or the ratio of the Aβ42 fragment to the Aβ40 fragment, of 0.25 or less is predictive or diagnostic of Alzheimer's disease. In some embodiments, the ratio of Aβ42 to Aβ40, or the ratio of the Aβ42 fragment to the Aβ40 fragment, of 0.2 or less is predictive or diagnostic of Alzheimer's disease. In some embodiments, the ratio of Aβ42 to Aβ40, or the ratio of the Aβ42 fragment to the Aβ40 fragment, of 0.15 or less is predictive or diagnostic of Alzheimer's disease.

In certain embodiments, the methods include generating one or more precursor ions of Aβ or a fragment thereof. In some embodiments, at least one of the precursor ions has a mass/charge ratio of 1085.6±0.5 or 1269.7±0.5. In some embodiments, the methods may include generating one or more fragment ions of Aβ or a fragment thereof. In some embodiments, at least one of the fragment ions has a mass/charge ratio of 812.37±0.5, 869.4+0.5, 968.43±0.5, 869.39±0.5, 968.44±0.5, 1067.5±0.5, or 1180.57±0.5.

In certain embodiments, the methods provided herein comprise adding an internal standard. In some embodiments, the internal standard comprises an isotopically labeled internal standard. In some embodiments, the internal standard comprises $^{13}C^{15}N$ labeling. In some embodiments, the internal standard comprises at least one Phe, Leu, or Met labeled with $^{13}C^{15}N$. In some embodiments, at least one of the precursor ions of the internal standard has a mass/charge ratio of 1110.7±0.5. In some embodiments, the methods may include generating one or more fragment ions of the internal standard. In some embodiments, at least one of the fragment ions has a mass/charge ratio of 768.48±0.5, 825.5±0.5, or 882.52±0.5.

In certain embodiments, the limit of quantitation of the methods is less than or equal to 10 ng/mL. In some embodiments, the limit of quantitation of the methods is less than or equal to 5 ng/mL. In some embodiments, the limit of quantitation of the methods is less than or equal to 4 ng/mL. In some embodiments, the limit of quantitation of the methods is less than or equal to 3 ng/mL. In some embodiments, the limit of quantitation of the methods is less than or equal to 2 ng/mL. In some embodiments, the limit of quantitation of the methods is less than or equal to 1 ng/mL. In some embodiments, the limit of quantitation of the methods is less than or equal to 0.5 ng/mL. In some embodiments, the limit of quantitation of the methods is less than or equal to 0.2 ng/mL. In some embodiments, the limit of quantitation of the methods is less than or equal to 0.1 ng/mL.

In some embodiments, the limit of detection of the methods is less than or equal to 5 ng/mL. In some embodiments, the limit of detection of the methods is less than or equal to 1 ng/mL. In some embodiments, the limit of detection of the methods is less than or equal to 0.5 ng/mL. In some embodiments, the limit of detection of the methods is less than or equal to 0.1 ng/mL. In some embodiments, the limit of detection of the methods is less than or equal to 0.05 ng/mL. In some embodiments, the limit of detection of the methods is less than or equal to 0.01 ng/mL.

In some embodiments, amyloid beta is not derivatized prior to mass spectrometry. In some embodiments, amyloid beta is derivatized prior to mass spectrometry.

In certain embodiments, the sample is a body fluid. In some embodiments, the sample is cerebrospinal fluid (CSF). In some embodiments, the sample is plasma or serum. In some embodiments, the sample is whole blood. In some embodiments, the sample is saliva or urine.

In some embodiments, the methods may include adding an agent to the sample in an amount sufficient to deproteinate the sample.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Samples are purified herein by various means to allow removal of one or more interfering substances, e.g., one or more substances that would interfere with the detection of selected amyloid beta parent and daughter ions by mass spectrometry.

As used herein, the term "test sample" refers to any sample that may contain amyloid beta. As used herein, the term "body fluid" means any fluid that can be isolated from the body of an individual. For example, "body fluid" may include blood, plasma, serum, bile, saliva, urine, tears, perspiration, and the like.

As used herein, the term "derivatizing" means reacting two molecules to form a new molecule. Derivatizing agents may include isothiocyanate groups, dinitro-fluorophenyl groups, nitrophenoxycarbonyl groups, and/or phthalaldehyde groups, and the like.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and high turbulence liquid chromatography (HTLC).

As used herein, the term "high performance liquid chromatography" or "HPLC" refers to liquid chromatography in which the degree of separation is increased by forcing the mobile phase under pressure through a stationary phase, typically a densely packed column As used herein, the term "high turbulence liquid chromatography" or "HTLC" refers to a form of chromatography that utilizes turbulent flow of the material being assayed through the column packing as the basis for performing the separation. HTLC has been applied in the preparation of samples containing two unnamed drugs prior to analysis by mass spectrometry. See, e.g., Zimmer et al., *J. Chromatogr. A* 854: 23-35 (1999); see also, U.S. Pat. Nos. 5,968,367, 5,919,368, 5,795,469, and 5,772,874, which further explain HTLC. Persons of ordinary skill in the art understand "turbulent flow". When fluid flows slowly and smoothly, the flow is called "laminar flow". For example, fluid moving through an HPLC column at low flow rates is laminar In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 35 μm. As used in this context, the term "about" means±10%. In a preferred embodiment the column contains particles of about 60 μm in diameter.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%. In a preferred embodiment the analytical column contains particles of about 4 μm in diameter.

As used herein, the term "on-line" or "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autos ampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g.ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectroscopy methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" or "APPI" as used herein refers to the form of mass spectroscopy where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. Robb, D. B., Covey, T. R. and Bruins, A. P. (2000): See, e.g., Robb et al., Atmospheric pressure photoionization: An ionization method for liquid chromatography-mass spectrometry. Anal. Chem. 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

As used herein, the term "limit of quantification", "limit of quantitation" or "LOQ" refers to the point where measurements become quantitatively meaningful. The analyte response at this LOQ is identifiable, discrete and reproducible with a precision of 20% and an accuracy of 80% to 120%.

As used herein, the term "limit of detection" or "LOD" is the point at which the measured value is larger than the uncertainty associated with it. The LOD is defined arbitrarily as 2 standard deviations (SD) from the zero concentration.

As used herein, an "amount" of amyloid beta in a body fluid sample refers generally to an absolute value reflecting the mass of amyloid beta detectable in volume of body fluid. However, an amount also contemplates a relative amount in comparison to another amyloid beta amount. For example, an amount of amyloid beta in a body fluid can be an amount which is greater than or less than a control or normal level of amyloid beta normally present.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.5 atomic mass unit.

The summary of the invention described above is non-limiting and other features and advantages of the invention will be apparent from the following detailed description of the invention, and from the claims.

BRIEF DESCRIPTION OF THE DRAWINGS

FIG. 1 shows the sequences of Aβ40 (SEQ ID NO:1), Aβ40 fragment (SEQ ID NO:2), Aβ42 (SEQ ID NO:3), and Aβ42 fragment (SEQ ID NO:4).

FIG. 11 shows the sensitivity comparison between C8 versus C4 analytical columns

DETAILED DESCRIPTION OF THE INVENTION

Figure 2:
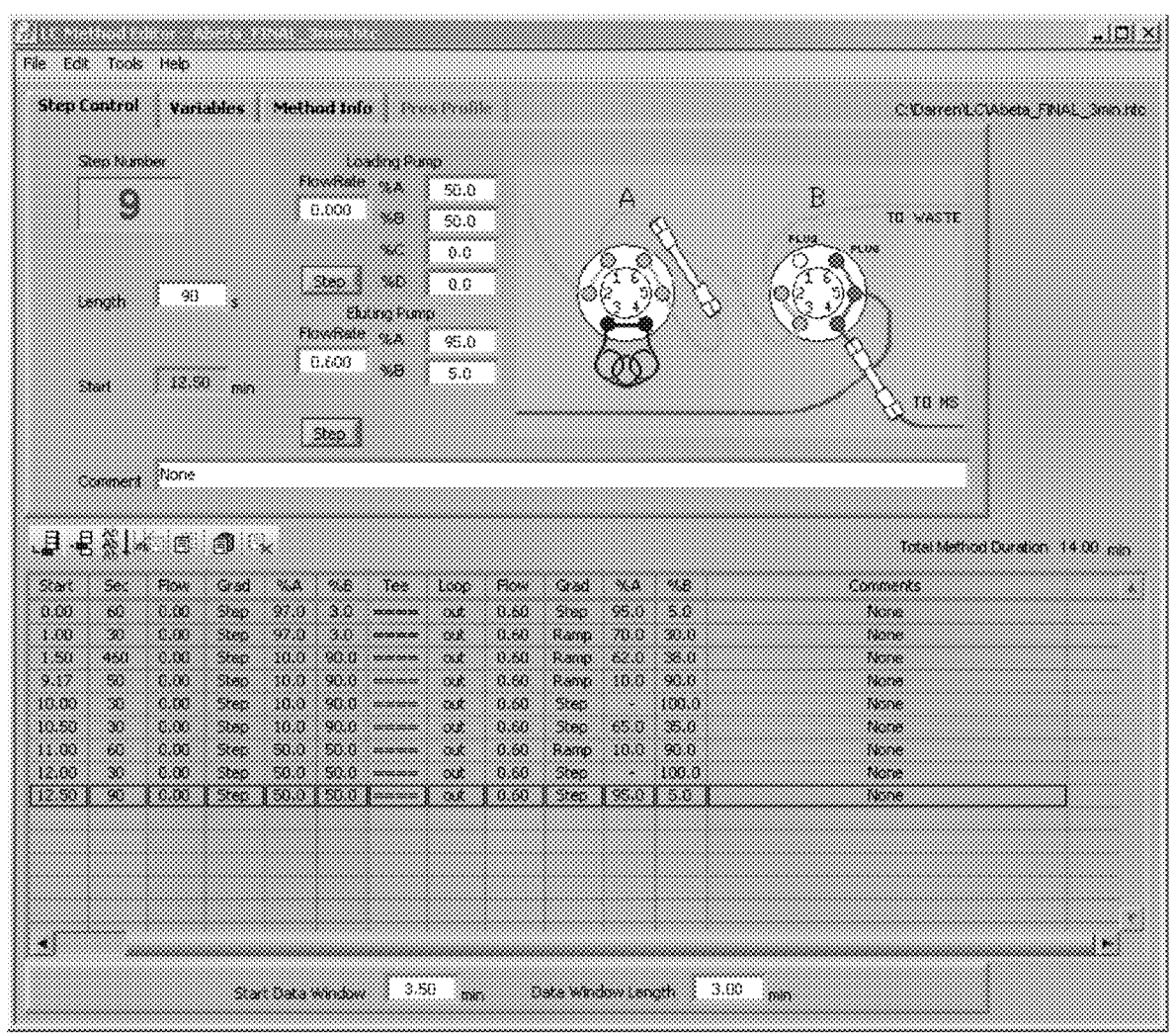
FIG. 2 shows the liquid chromatography method information. Mobile phase A of 0.1% FA in water and mobile phase B of 0.1% FA in ACN were used.
Figure 3:
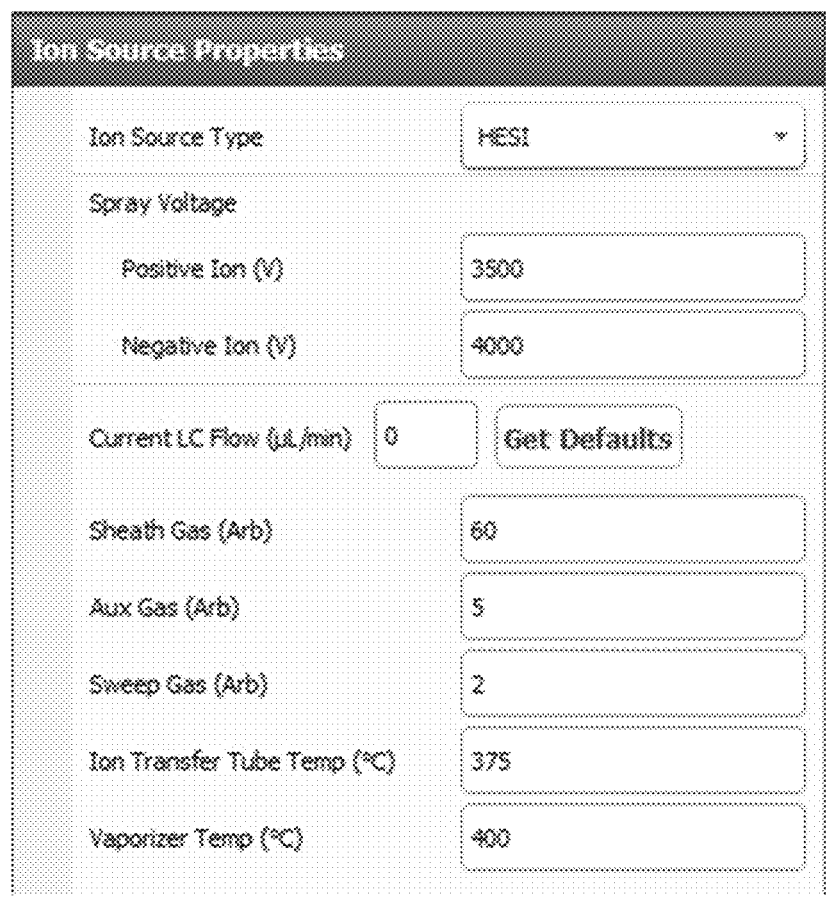
FIG. 3 shows the heated electrospray ionization (HESI) ion source conditions.

Provided herein are methods for detecting or determining the amount of amyloid beta (Aβ) in a sample by mass spectrometry, including tandem mass spectrometry. In certain embodiments, the methods provided herein for determining the amount of amyloid beta comprises (a) purifying amyloid beta in the sample; (b) ionizing amyloid beta in the sample; and (c) determining the amount of the amyloid beta ion(s) by mass spectrometry; wherein the amount of the amyloid beta ion(s) is related to the amount of amyloid beta in the sample.

In certain embodiments, the methods provided herein for determining the amount of amyloid beta comprises (a) purifying amyloid beta in the sample; (b) ionizing amyloid beta in the sample to produce a precursor ion of amyloid beta; (c) generating one or more fragment ions of amyloid beta; and (d) determining the amount of the ion(s) from step (c) or (d) or both by mass spectrometry; wherein the amount of the amyloid beta ion(s) is related to the amount of amyloid beta in the sample.

In certain embodiments, the methods provided herein for determining the amount of amyloid beta comprises (a) digesting amyloid beta in the sample to generate one or more fragments of amyloid beta; (b) purifying the one or more amyloid beta fragments; (c) ionizing amyloid beta in the sample to produce a precursor ion of amyloid beta; (d) generating one or more fragment ions of amyloid beta; and (e) determining the amount of the ion(s) from step (c) or (d) or both by mass spectrometry; wherein the amount of the amyloid beta ion(s) is related to the amount of amyloid beta in the sample.

In certain embodiments, provided herein are methods for determining the amount of amyloid beta 42 (Aβ42). In some embodiments, the Aβ42 fragment comprises the sequence GAIIGLMVGGVVIA (SEQ ID NO:4). In some embodiments, the methods comprise (a) digesting amyloid beta in the sample to generate amyloid beta 42 (Aβ42); (b) purifying Aβ42; (c) ionizing Aβ42 to produce a precursor ion; (d) generating one or more fragment ions of Aβ42; and (e) determining the amount of the ion(s) from step (c) or (d) or both by mass spectrometry; wherein the amount of the ion(s) is related to the amount of Aβ42 in the sample.

In certain embodiments, provided herein are methods for determining the amount of amyloid beta 40 (Aβ40). In some embodiments, the Aβ40 fragment comprises the sequence GAIIGLMVGGVV (SEQ ID NO:2). In some embodiments, the methods comprise (a) digesting amyloid beta in the sample to generate amyloid beta 40 (Aβ40); (b) purifying Aβ40; (c) ionizing Aβ40 to produce a precursor ion; (d) generating one or more fragment ions of Aβ40; and (e) determining the amount of the ion(s) from step (c) or (d) or both by mass spectrometry; wherein the amount of the ion(s) is related to the amount of Aβ40 in the sample.

In certain embodiments, provided herein are methods for determining the amount of amyloid beta 42 (Aβ42) and amyloid beta 40 (Aβ40). In some embodiments, the methods comprise (a) digesting amyloid beta in the sample to generate amyloid beta 42 (Aβ42) and amyloid beta 40 (Aβ40); (b) purifying Aβ42 and Aβ40; (c) ionizing Aβ42 and Aβ40 to produce precursor ions; (d) generating one or more fragment ions of Aβ42 and Aβ40; and (e) determining the amount of the ion(s) from step (c) or (d) or both by mass spectrometry; wherein the amount of the ion(s) is related to the amount of Aβ42 and Aβ40 in the sample.

In certain embodiments, provided herein are methods for determining the ratio of amyloid beta 42 (Aβ42) to amyloid beta 40 (Aβ40). In some embodiments, the methods comprise (a) digesting amyloid beta in the sample to generate amyloid beta 42 (Aβ42) and amyloid beta 40 (Aβ40); (b) purifying Aβ42 and Aβ40; (c) ionizing Aβ42 and Aβ40 to produce precursor ions; (d) generating one or more fragment ions of Aβ42 and Aβ40; and (e) determining the amount of the ion(s) from step (c) or (d) or both by mass spectrometry; and (f) determining the ratio of Aβ42 to Aβ40. In some embodiments, the methods comprise determining the ratio of Aβ40 to Aβ42.

In certain embodiments, provided herein are methods for diagnosis or prognosis of Alzheimer's disease or dementia, the method comprising determining the amount of amyloid beta in a test sample by mass spectrometry; wherein an abnormal levels of amyloid beta is predictive or diagnostic of Alzheimer's disease. In some embodiments, the methods may include: (a) purifying amyloid beta in the sample; (b) ionizing amyloid beta in the sample; and (c) determining the amount of the amyloid beta ion(s) by mass spectrometry; and (d) the amount of the amyloid beta ion(s) is related to the amount of amyloid beta in the sample; wherein the abnormal levels of amyloid beta is predictive or diagnostic of Alzheimer's disease. In some embodiments, the methods comprise determining the ratio of amyloid beta fragments. In some embodiments, the methods comprise determining the ratio of amyloid beta 42 (Aβ42) to amyloid beta 40 (Aβ40). In some embodiments, the methods comprise determining the ratio of amyloid beta 42 (Aβ40) to amyloid beta 40 (Aβ42).

In certain embodiments, the methods provided herein comprise pretreating surfaces of equipment that come in contact with the sample. In some embodiments, the pretreatment comprises pre-coating the surfaces of equipment with an agent that prevents amyloid beta or fragments thereof from sticking to the surfaces. In some embodiments, the pretreatment comprises bacterial lysate pretreatment. In some embodiments, the pretreatment comprises *E. coli* lysate pretreatment. In some embodiments, the *E. coli* lysate comprises a trypsin-digested *E. coli* lysate. In some embodiments, the pretreated equipment includes, but not limited to, test tubes or plates, pipette tips, sample preparation apparatus, liquid chromatography apparatus, and mass spectrometry apparatus.

In certain embodiments, the methods provided herein comprise treating or incubating the sample with an agent that stabilizes amyloid beta or fragments thereof. In some embodiments, the methods provided herein comprise treating or incubating the sample with an amyloid beta antibody. In some embodiments, the methods provided herein comprise treating or incubating the sample with at least two distinct amyloid beta antibodies. In some embodiments, the amyloid beta antibody comprises an antibody that binds to the C-terminus of amyloid beta. In some embodiments, the amyloid beta antibody comprises an antibody that binds to the N-terminus of amyloid beta. In some embodiments, the agent that stabilizes amyloid beta comprises an apolipoprotein. In some embodiments, the agent that stabilizes amyloid beta comprises apolipoprotein E2. In some embodiments, the agent that stabilizes amyloid beta comprises apolipoprotein E4. In some embodiments, the agent that stabilizes amyloid beta comprises an antibody that binds to the C-terminus of amyloid beta, an antibody that binds to the N-terminus of amyloid beta, apolipoprotein E2, apolipoprotein E4, or a combination thereof. In some embodiments, the agent that stabilizes amyloid beta provided herein confers stability for at least 1 month at −70° C. In some embodiments, the agent that stabilizes amyloid beta provided herein confers stability for at least 2 months at −70° C. In some embodiments, the agent that stabilizes amyloid beta provided herein confers stability for at least 3 months at −70° C. In some embodiments, the agent that stabilizes amyloid beta provided herein confers stability through a freeze-thaw cycle. In some embodiments, the agent that stabilizes amyloid beta provided herein confers stability through at least two freeze-thaw cycles. In some embodiments, the agent that stabilizes amyloid beta provided herein confers stability through at least three freeze-thaw cycles. In some embodiments, the agent that stabilizes amyloid beta provided herein confers stability through at least four freeze-thaw cycles.

In certain embodiments, the methods provided herein comprise digesting amyloid beta in the sample. In some embodiments, the methods provided herein comprise digesting amyloid beta with an enzyme. In some embodiments, the enzyme is Lys-C. In some embodiments, the methods provided herein comprise digesting amyloid beta with urea. In some embodiments, the urea is in a concentration suitable for protein digestion. In some embodiments, the urea is 6M urea. In some embodiments, the methods provided herein comprise digesting amyloid beta with urea and Lys-C. In some embodiments, the digestion comprises digesting in conditions that reduce digestion time or increase digestion efficiency. In some embodiments, the digestion comprises digesting in microwave.

In certain embodiments, the methods provided herein comprise an extraction. In some embodiments, the methods provided herein comprise a mixed mode anion exchange extraction. In some embodiments, the methods provided herein comprise a solid phase extraction.

In certain embodiments, the methods provided herein comprise eluting and drying the sample using heated nitrogen. In some embodiments, the sample is resuspended in a reconstitution buffer.

In certain embodiments, the purifying the sample comprises a liquid chromatography. In some embodiments, liquid chromatography includes, but not limited to, reverse phase liquid chromatography (RPLC), high performance liquid chromatography (HPLC), and high turbulence liquid chromatography (HTLC). In a preferred embodiment, liquid chromatography comprises HPLC. In some embodiments, HPLC column typically includes a medium (i.e., a packing material) to facilitate separation of chemical moieties (i.e., fractionation). Suitable columns may include C-4, C-8, C-12, or C-18 columns. In a preferred embodiment, a suitable HPLC column is C-4 column.

In certain embodiments, the methods provided herein comprise using equipment that reduces sticking of amyloid beta to the surfaces of equipment. In some embodiments, the equipment comprises PEEK (poly ether ether ketone) tubing or apparatus. In some embodiments, the equipment comprises metal tubing or apparatus.

In certain embodiments, the methods provided herein comprise tandem mass spectrometry. In some embodiments, the methods provided herein comprise ionizing in positive mode. In some embodiments, the methods provided herein comprise ionizing in negative mode. In some embodiments, the methods provided herein comprise ionizing using heated electrospray ionization (HESI). In some embodiments, the methods provided herein comprise ionizing using electrospray ionization (ESI). In some embodiments, the methods provided herein comprise ionizing using atmospheric pressure chemical ionization (APCI). In a preferred embodiment, the methods provided herein comprise ionizing using heated electrospray ionization (HESI) in positive mode. In some embodiments, the collision energy is between 5V to 60V. In some embodiments, the collision energy is between 10V to 50V. In some embodiments, the collision energy is between 20V to 50V. In some embodiments, the collision energy is between 20V to 45V.

In certain embodiments, the methods provided herein comprise detecting or determining the amount of amyloid beta 40 (Aβ40). In some embodiments, Aβ40 comprises the sequence DAEFRHDSGYEVHHQKLVFFAEDVGSNK-GAIIGLMVGGVV (SEQ ID NO:1). In some embodiments, the methods provided herein comprise detecting or determining the amount of a fragment of Aβ40. In some embodiments, the Aβ40 fragment comprises the sequence GAIIGLMVGGVV (SEQ ID NO:2). In some embodiments, the Aβ40 fragment comprises a sequence containing an N-terminal or C-terminal winged peptide. In some embodiments, the Aβ40 fragment comprises SEQ ID NO:2 and an N-terminal or C-terminal winged peptide. In some embodiments, the winged peptide is hydrophilic. In some embodiments, the winged peptide comprises at least one amino acid. In some embodiments, the winged peptide comprises at least two amino acids. In some embodiments, the winged peptide comprises at least three amino acids. In some embodiments, the winged peptide comprises at least four amino acids. In some embodiments, the winged peptide comprises at least five amino acids. In some embodiments, the winged peptide comprises at least six amino acids. In some embodiments, the amount of the Aβ40 fragment correlates to the amount of Aβ40 in the sample.

In certain embodiments, the methods provided herein comprise detecting or determining the amount of amyloid beta 42 (Aβ42). In some embodiments, Aβ42 comprises the sequence DAEFRHDSGYEVHHQKLVFFAEDVGSNK-GAIIGLMVGGVVIA (SEQ ID NO:3). In some embodiments, the methods provided herein comprise detecting or determining the amount of a fragment of Aβ42. In some embodiments, the Aβ42 fragment comprises the sequence GAIIGLMVGGVVIA (SEQ ID NO:4). In some embodiments, the Aβ42 fragment comprises a sequence containing an N-terminal or C-terminal winged peptide. In some embodiments, the Aβ42 fragment comprises SEQ ID NO:4 and an N-terminal or C-terminal winged peptide. In some embodiments, the winged peptide is hydrophilic. In some embodiments, the winged peptide comprises at least one amino acid. In some embodiments, the winged peptide comprises at least two amino acids. In some embodiments, the winged peptide comprises at least three amino acids. In some embodiments, the winged peptide comprises at least four amino acids. In some embodiments, the winged peptide comprises at least five amino acids. In some embodiments, the winged peptide comprises at least six amino acids. In some embodiments, the amount of the Aβ42 fragment correlates to the amount of Aβ42 in the sample.

In certain embodiments, the methods provided herein comprise detecting or determining the ratio of Aβ40 to Aβ42 (Aβ40:Aβ42). In some embodiments, the methods provided herein comprise detecting or determining the ratio of the Aβ40 fragment to the Aβ42 fragment (Aβ40 fragment:Aβ42 fragment). In some embodiments, the methods provided herein comprise detecting or determining the ratio of Aβ42 to Aβ40 (Aβ42:Aβ40). In some embodiments, the methods provided herein comprise detecting or determining the ratio of the Aβ42 fragment to the Aβ40 fragment (Aβ42 fragment: Aβ40 fragment).

In certain embodiments, the ratio of Aβ42 to Aβ40, or the ratio of the Aβ42 fragment to the Aβ40 fragment, of 0.6 or less is predictive or diagnostic of Alzheimer's disease. In some embodiments, the ratio of Aβ42 to Aβ40, or the ratio of the Aβ42 fragment to the Aβ40 fragment, of 0.5 or less is predictive or diagnostic of Alzheimer's disease. In some embodiments, the ratio of Aβ42 to Aβ40, or the ratio of the Aβ42 fragment to the Aβ40 fragment, of 0.45 or less is predictive or diagnostic of Alzheimer's disease. In some embodiments, the ratio of Aβ42 to Aβ40, or the ratio of the Aβ42 fragment to the Aβ40 fragment, of 0.4 or less is predictive or diagnostic of Alzheimer's disease. In some embodiments, the ratio of Aβ42 to Aβ40, or the ratio of the Aβ42 fragment to the Aβ40 fragment, of 0.35 or less is predictive or diagnostic of Alzheimer's disease. In some embodiments, the ratio of Aβ42 to Aβ40, or the ratio of the Aβ42 fragment to the Aβ40 fragment, of 0.3 or less is predictive or diagnostic of Alzheimer's disease. In some embodiments, the ratio of Aβ42 to Aβ40, or the ratio of the Aβ42 fragment to the Aβ40 fragment, of 0.25 or less is predictive or diagnostic of Alzheimer's disease. In some embodiments, the ratio of Aβ42 to Aβ40, or the ratio of the Aβ42 fragment to the Aβ40 fragment, of 0.2 or less is predictive or diagnostic of Alzheimer's disease. In some embodiments, the ratio of Aβ42 to Aβ40, or the ratio of the Aβ42 fragment to the Aβ40 fragment, of 0.19 or less is predictive or diagnostic of Alzheimer's disease. In some embodiments, the ratio of Aβ42 to Aβ40, or the ratio of the Aβ42 fragment to the Aβ40 fragment, of 0.18 or less is predictive or diagnostic of Alzheimer's disease. In some embodiments, the ratio of Aβ42 to Aβ40, or the ratio of the Aβ42 fragment to the Aβ40 fragment, of 0.17 or less is predictive or diagnostic of Alzheimer's disease. In some embodiments, the ratio of Aβ42 to Aβ40, or the ratio of the Aβ42 fragment to the Aβ40 fragment, of 0.16 or less is predictive or diagnostic of Alzheimer's disease. In some embodiments, the ratio of Aβ42 to Aβ40, or the ratio of the Aβ42 fragment to the Aβ40 fragment, of 0.15 or less is predictive or diagnostic of Alzheimer's disease. In some embodiments, the ratio of Aβ42 to Aβ40, or the ratio of the Aβ42 fragment to the Aβ40 fragment, of 0.1 or less is predictive or diagnostic of Alzheimer's disease.

In certain embodiments, the methods include generating one or more precursor ions of AP or a fragment thereof. In some embodiments, at least one of the precursor ions has a mass/charge ratio of 1085.6±0.5 or 1269.7±0.5. In some embodiments, the methods may include generating one or more fragment ions of Aβ or a fragment thereof. In some embodiments, at least one of the fragment ions has a mass/charge ratio of 812.37±0.5, 869.4±0.5, 968.43±0.5, 869.39±0.5, 968.44±0.5, 1067.5±0.5, or 1180.57±0.5.

In certain embodiments, the methods provided herein comprise adding an internal standard. In some embodiments, the internal standard comprises an isotopically labeled internal standard. In some embodiments, the internal standard comprises $^{13}C^{15}N$ labeling. In some embodiments, the internal standard comprises at least one Phe, Leu, or Met labeled with $^{13}C^{15}N$. In some embodiments, at least one of the precursor ions of the internal standard has a mass/charge ratio of 1110.7±0.5. In some embodiments, the methods may include generating one or more fragment ions of the internal standard. In some embodiments, at least one of the fragment ions has a mass/charge ratio of 768.48±0.5, 825.5±0.5, or 882.52±0.5.

In certain embodiments, the limit of quantitation of the methods is less than or equal to 10 ng/mL. In some embodiments, the limit of quantitation of the methods is less than or equal to 5 ng/mL. In some embodiments, the limit of quantitation of the methods is less than or equal to 4 ng/mL. In some embodiments, the limit of quantitation of the methods is less than or equal to 3 ng/mL. In some embodiments, the limit of quantitation of the methods is less than or equal to 2 ng/mL. In some embodiments, the limit of quantitation of the methods is less than or equal to 1 ng/mL. In some embodiments, the limit of quantitation of the methods is less than or equal to 0.5 ng/mL. In some embodiments, the limit of quantitation of the methods is less than or equal to 0.2 ng/mL. In some embodiments, the limit of quantitation of the methods is less than or equal to 0.1 ng/mL.

In some embodiments, the limit of detection of the methods is less than or equal to 5 ng/mL. In some embodiments, the limit of detection of the methods is less than or equal to 1 ng/mL. In some embodiments, the limit of detection of the methods is less than or equal to 0.5 ng/mL. In some embodiments, the limit of detection of the methods is less than or equal to 0.1 ng/mL. In some embodiments, the limit of detection of the methods is less than or equal to 0.05 ng/mL. In some embodiments, the limit of detection of the methods is less than or equal to 0.01 ng/mL.

In some embodiments, amyloid beta is not derivatized prior to mass spectrometry. In some embodiments, amyloid beta is derivatized prior to mass spectrometry.

In certain embodiments, the sample is a body fluid. In some embodiments, the sample is cerebrospinal fluid (CSF). In some embodiments, the sample is plasma or serum. In some embodiments, the sample is whole blood. In some embodiments, the sample is saliva or urine.

Suitable test samples include any test sample that may contain the analyte of interest. In some preferred embodiments, a sample is a biological sample; that is, a sample obtained from any biological source, such as an animal, a cell culture, an organ culture, etc. In certain preferred embodiments samples are obtained from a mammalian animal, such as a dog, cat, horse, etc. Particularly preferred mammalian animals are primates, most preferably male or female humans. Particularly preferred samples include blood, plasma, serum, hair, muscle, urine, saliva, tear, cerebrospinal fluid, or other tissue sample. Such samples may be obtained, for example, from a patient; that is, a living person, male or female, presenting oneself in a clinical setting for diagnosis, prognosis, or treatment of a disease or condition. The test sample is preferably obtained from a patient, for example, blood serum.

Sample Preparation for Mass Spectrometry

Methods that may be used to enrich in amyloid beta relative to other components in the sample (e.g. protein) include for example, filtration, centrifugation, thin layer chromatography (TLC), electrophoresis including capillary electrophoresis, affinity separations including immunoaffinity separations, extraction methods including ethyl acetate extraction and methanol extraction, and the use of chaotropic agents or any combination of the above or the like.

Protein precipitation is one preferred method of preparing a test sample. Such protein purification methods are well known in the art, for example, Polson et al., *Journal of Chromatography B* 785:263-275 (2003), describes protein precipitation techniques suitable for use in the methods. Protein precipitation may be used to remove most of the protein from the sample leaving amyloid beta in the supernatant. The samples may be centrifuged to separate the liquid supernatant from the precipitated proteins. The resultant supernatant may then be applied to liquid chromatography and subsequent mass spectrometry analysis. In certain embodiments, the use of protein precipitation such as for example, acetonitrile protein precipitation, obviates the need for high turbulence liquid chromatography (HTLC) or other on-line extraction prior to HPLC and mass spectrometry. Accordingly in such embodiments, the method involves (1) performing a protein precipitation of the sample of interest; and (2) loading the supernatant directly onto the HPLC-mass spectrometer without using on-line extraction or high turbulence liquid chromatography (HTLC).

In some preferred embodiments, HPLC, alone or in combination with one or more purification methods, may be used to purify amyloid beta prior to mass spectrometry. In such embodiments samples may be extracted using an HPLC extraction cartridge which captures the analyte, then eluted and chromatographed on a second HPLC column or onto an analytical HPLC column prior to ionization. Because the steps involved in these chromatography procedures can be linked in an automated fashion, the requirement for operator involvement during the purification of the analyte can be minimized This feature can result in savings of time and costs, and eliminate the opportunity for operator error.

It is believed that turbulent flow, such as that provided by HTLC columns and methods, may enhance the rate of mass transfer, improving separation characteristics. HTLC columns separate components by means of high chromatographic flow rates through a packed column containing rigid particles. By employing high flow rates (e.g., 3-5 mL/min), turbulent flow occurs in the column that causes nearly complete interaction between the stationary phase and the analyte(s) of interest. An advantage of using HTLC columns is that the macromolecular build-up associated with biological fluid matrices is avoided since the high molecular weight species are not retained under the turbulent flow conditions. HTLC methods that combine multiple separations in one procedure lessen the need for lengthy sample preparation and operate at a significantly greater speed. Such methods also achieve a separation performance superior to laminar flow (HPLC) chromatography. HTLC allows for direct injection of biological samples (plasma, urine, etc.). Direct injection is difficult to achieve in traditional forms of chromatography because denatured proteins and other biological debris quickly block the separation columns. HTLC also allows for very low sample volume of less than 1 mL, preferably less than 0.5 mL, preferably less than 0.2 mL, preferably 0.1 mL.

Examples of HTLC applied to sample preparation prior to analysis by mass spectrometry have been described elsewhere. See, e.g., Zimmer et al., *J. Chromatogr.* A 854:23-35 (1999); see also, U.S. Pat. Nos. 5,968,367; 5,919,368; 5,795,469; and 5,772,874. In certain embodiments of the method, samples are subjected to protein precipitation as described above prior to loading on the HTLC column; in alternative preferred embodiments, the samples may be loaded directly onto the HTLC without being subjected to protein precipitation. The HTLC extraction column is preferably a large particle column. In various embodiments, one of more steps of the methods may be performed in an on-line, automated fashion. For example, in one embodiment, steps (i)-(v) are performed in an on-line, automated fashion. In another, the steps of ionization and detection are performed on-line following steps (i)-(v).

Liquid chromatography (LC) including high-performance liquid chromatography (HPLC) relies on relatively slow, laminar flow technology. Traditional HPLC analysis relies on column packings in which laminar flow of the sample through the column is the basis for separation of the analyte of interest from the sample. The skilled artisan will understand that separation in such columns is a diffusional process. HPLC has been successfully applied to the separation of compounds in biological samples but a significant amount of sample preparation is required prior to the separation and subsequent analysis with a mass spectrometer (MS), making this technique labor intensive. In addition, most HPLC systems do not utilize the mass spectrometer to its fullest potential, allowing only one HPLC system to be connected to a single MS instrument, resulting in lengthy time requirements for performing a large number of assays.

Various methods have been described for using HPLC for sample clean-up prior to mass spectrometry analysis. See, e.g., Taylor et al., *Therapeutic Drug Monitoring* 22:608-12 (2000); and Salm et al., *Clin. Therapeutics* 22 Supl. B:B71-B85 (2000).

One of skill in the art may select HPLC instruments and columns that are suitable for use with amyloid beta. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, C-12, or C-18 bonded alkyl groups, preferably C-18 bonded groups. The chromatographic column includes an inlet port for receiving a sample and an outlet port for discharging an effluent that includes the fractionated sample. In one embodiment, the sample (or pre-purified sample) is applied to the column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, the HTLC may be followed by HPLC on a hydrophobic column chromatographic system. In certain preferred embodiments, a TurboFlow Cyclone P® polymer-based column from Cohesive Technologies (60 μm particle size, 50×1.0 mm column dimensions, 100 Å pore size) is used. In related preferred embodiments, a Synergi Polar-RP® ether-linked phenyl, analytical column from Phenomenex Inc (4 μm particle size, 150×2.0 mm column dimensions, 80 Å pore size) with hydrophilic endcapping is used. In certain preferred embodiments, HTLC and HPLC are performed using HPLC Grade Ultra Pure Water and 100% methanol as the mobile phases.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In certain preferred embodiments, amyloid beta or fragments thereof in a sample may be purified prior to ionization. In particularly preferred embodiments the chromatography is not gas chromatography.

Detection and Quantitation by Mass Spectrometry

In various embodiments, amyloid beta or fragments thereof may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

In preferred embodiments, amyloid beta or a fragment thereof is ionized by heated electrospray ionization (HESI) in positive or negative mode. In alternative embodiments, amyloid beta or a fragment thereof is ionized by electrospray ionization (ESI) or atmospheric pressure chemical ionization (APCI) in positive or negative mode.

After the sample has been ionized, the positively charged or negatively charged ions thereby created may be analyzed to determine a mass-to-charge ratio. Suitable analyzers for determining mass-to-charge ratios include quadrupole analyzers, ion traps analyzers, and time-of-flight analyzers. The ions may be detected using several detection modes. For example, selected ions may be detected i.e., using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 100 to 1000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of amyloid beta. Methods of generating and using such standard curves are well known in the art and one of ordinary skill is capable of selecting an appropriate internal standard. For example, an isotope of amyloid beta may be used as an internal standard. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activation dissociation is often used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy.

In particularly preferred embodiments, amyloid beta is detected and/or quantified using MS/MS as follows. The samples are subjected to liquid chromatography, preferably HPLC, the flow of liquid solvent from the chromatographic column enters the heated nebulizer interface of an MS/MS analyzer and the solvent/analyte mixture is converted to vapor in the heated tubing of the interface. The analyte is ionized by the selected ionizer. The ions, e.g. precursor ions, pass through the orifice of the instrument and enter the first quadrupole. Quadrupoles 1 and 3 (Q1 and Q3) are mass filters, allowing selection of ions (i.e., "precursor" and "fragment" ions) based on their mass to charge ratio (m/z). Quadrupole 2 (Q2) is the collision cell, where ions are fragmented. The first quadrupole of the mass spectrometer (Q1) selects for molecules with the mass to charge ratios of amyloid beta. Precursor ions with the correct mass/charge ratios of amyloid beta are allowed to pass into the collision chamber (Q2), while unwanted ions with any other mass/charge ratio collide with the sides of the quadrupole and are eliminated. Precursor ions entering Q2 collide with neutral argon gas molecules and fragment. This process is called collision activated dissociation (CAD). The fragment ions generated are passed into quadrupole 3 (Q3), where the fragment ions of amyloid beta are selected while other ions are eliminated.

The methods may involve MS/MS performed in either positive or negative ion mode. Using standard methods well known in the art, one of ordinary skill is capable of identifying one or more fragment ions of a particular precursor ion of amyloid beta that may be used for selection in quadrupole 3 (Q3).

If the precursor ion of amyloid beta includes an alcohol or amine group, fragment ions are commonly formed that represent dehydration or deamination of the precursor ion, respectfully. In the case of precursor ions that include an alcohol group, such fragment ions formed by dehydration are caused by a loss of one or more water molecules from the precursor ion (i.e., where the difference in mass to charge ratio between the precursor ion and fragment ion is about 18 for the loss of one water molecule, or about 36 for the loss of two water molecules, etc.). In the case of precursor ions that include an amine group, such fragment ions formed by deamination are caused by a loss of one or more ammonia molecules (i.e. where the difference in mass to charge ratio between the precursor ion and fragment ion is about 17 for the loss of one ammonia molecule, or about 34 for the loss of two ammonia molecules, etc.). Likewise, precursor ions that include one or more alcohol and amine groups commonly form fragment ions that represent the loss of one or more water molecules and/or one or more ammonia molecules (i.e., where the difference in mass to charge ratio between the precursor ion and fragment ion is about 35 for the loss of one water molecule and the loss of one ammonia molecule). Generally, the fragment ions that represent dehydrations or deaminations of the precursor ion are not specific fragment ions for a particular analyte. Accordingly, in preferred embodiments of the invention, MS/MS is performed such that at least one fragment ion of amyloid beta is detected that does not represent only a loss of one or more water molecules and/or a loss of one or more ammonia molecules from the precursor ion.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte of interest. In certain embodiments, the area under the curves, or amplitude of the peaks, for fragment ion(s) and/or precursor ions are measured to determine the amount of amyloid beta. As described above, the relative abundance of a given ion may be converted into an absolute amount of the original analyte, using calibration standard curves based on peaks of one or more ions of an internal molecular standard.

The following examples serve to illustrate the invention. These examples are in no way intended to limit the scope of the methods.

EXAMPLES

Example 1: Equipment Pretreatment and Amyloid Beta Stabilization

96 Well Polypropylene Plate and Microcentrifuge Test Tube Pretreatment

E. coli was lysed and precipitated using methanol in a 96 well plate.

Methanol was then discarded while the pellet is resuspended in ammonium bicarbonate pH 8.

Sigma bovine trypsin was added, and the samples were incubated at 60° C. for 2 days.

All digest was then discarded to waste or pooled to pretreat pipette tips.

Empty plates and test tubes were completely dried.
Pipette Tip Pre-Treatment

Pipette tips were used to pipette up and down E. coli digest at least 3 times and then incubated at 60° C. for 2 days or until completely dried.
Amyloid Beta Peptide Stabilization AB40, AB42, and internal standards were synthesized in pretreated test tubes and were resuspended in 6M urea with 4 mg BSA.

The standards were then individually diluted 1:10 in 0.1M PBS with N-terminal and C-terminal antibodies and apolipoprotein E2 and E4.

Each mixture was incubated at room temp on a shaker for 1 hour.

AB40 and AB42 was then combined and diluted down in 0.1M PBS and 0.4 mg/mL BSA to make high calibrator standards before being frozen.

The table below shows a side-by-side comparison of the same sample prepped in a treated and non-treated vial.

| AB42 | Treated-Calc. value | Non-treated-Calc. value | % Recovery |
|---|---|---|---|
| AB212 | 2.52 | 0.33 | 13.10 |
| AB213 | 2.14 | 0.81 | 37.85 |
| AB214 | 5.73 | 1.45 | 25.31 |
| AB215 | 0.92 | 0.21 | 22.83 |

-continued

| AB216 | 1.85 | 0.99 | 53.51 |

| AB40 | Treated-Calc. value | Non-treated-Calc. value | |
| --- | --- | --- | --- |
| AB212 | 15.01 | 2.73 | 18.19 |
| AB213 | 13.11 | 4.93 | 37.60 |
| AB214 | 19.18 | 5.62 | 29.30 |
| AB215 | 6.02 | 2.23 | 37.04 |
| AB216 | 7.08 | 4.76 | 67.23 |

Example 2: Sample Preparation 0.5 mL of sample or standard was pipetted using pre-treated pipette tips into a pre-treated 96 well plates.

5 ng of internal standard was added.

250 uL of 18M urea was added.

2 ug of Lys-C was added to each sample for digestion of amyloid beta.

Plate was sealed with an adhesive lid before being digested in a enzymatic microwave at 450 w, 4° C. for 4 hours.

Samples were then extracted using Waters mixed mode strong anion exchange.

Sample eluates were then dried down completely using heated nitrogen.

Samples were then resuspended in a reconstitution buffer for LC-MS/MS analysis.

Example 3: Detection and Quantitation of Amyloid Beta Fragments by MS/MS

Ions passed to the first quadrupole (Q1), which selected ions with a mass to charge ratio of either 1085.6±0.5 m/z or 1269.7±.5 m/z for the Aβ40 fragment and the Aβ42 fragment, respectively. Ions entering Quadrupole 2 (Q2) collided with argon gas to generate ion fragments, which were passed to quadrupole 3 (Q3) for further selection. Simultaneously, the same process using isotope dilution mass spectrometry was carried out with an internal standard. The following mass transitions were used for detection and quantitation during validation on positive polarity.

TABLE 1

Mass Transitions for Amyloid Beta fragments (Positive Polarity)

| Compound | Start Time (min) | End Time (min) | Polarity | Precursor (m/z) | Product (m/z) | Collision Energy (V) |
| --- | --- | --- | --- | --- | --- | --- |
| GAIIGLMVGGVV | 0 | 10 | Positive | 1085.60 | 812.37 | 31 |
| GAIIGLMVGGVV | 0 | 10 | Positive | 1085.60 | 869.40 | 33 |
| GAIIGLMVGGVV | 0 | 10 | Positive | 1085.60 | 968.43 | 23 |
| GAIIGLMVGGVVIA | 0 | 10 | Positive | 1269.70 | 869.39 | 43 |
| GAIIGLMVGGVVIA | 0 | 10 | Positive | 1269.70 | 968.44 | 34 |
| GAIIGLMVGGVVIA | 0 | 10 | Positive | 1269.70 | 1067.50 | 32 |
| GAIIGLMVGGVVIA | 0 | 10 | Positive | 1269.70 | 1180.57 | 23.8 |
| IS | 0 | 10 | Positive | 1110.70 | 768.48 | 35.5 |
| IS | 0 | 10 | Positive | 1110.70 | 825.50 | 35.5 |
| IS | 0 | 10 | Positive | 1110.70 | 882.52 | 35.5 |

Figure 6:
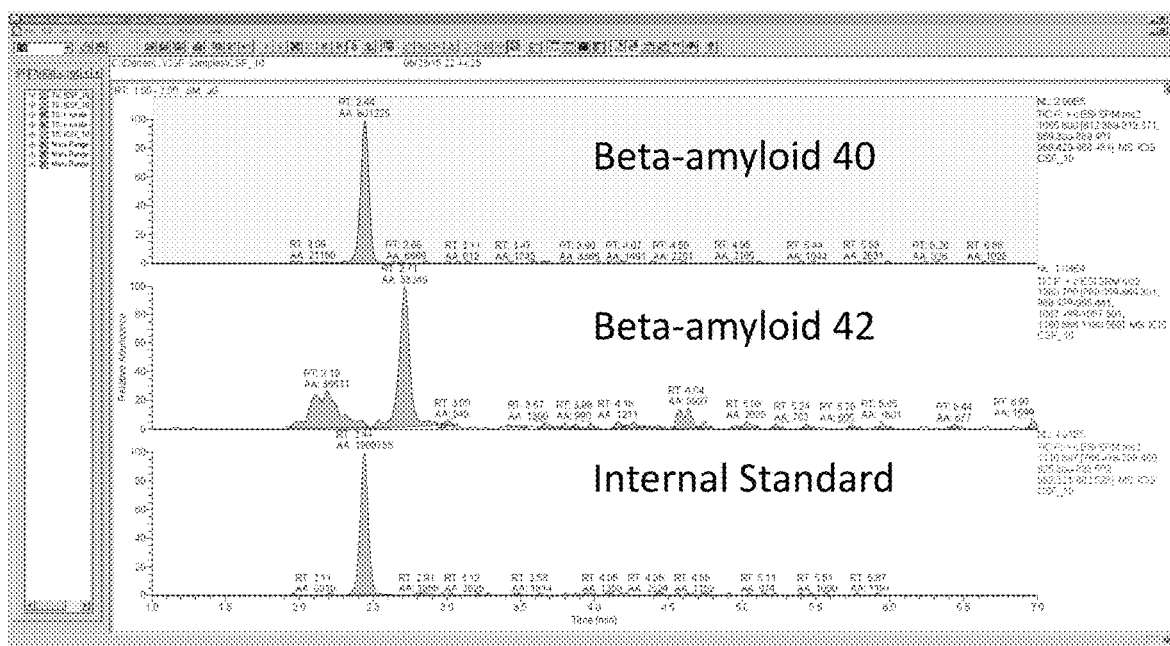
FIGS. 6 and 7 show example patient chromatograms of Aβ40, Aβ42, and internal standard.
Figure 7:
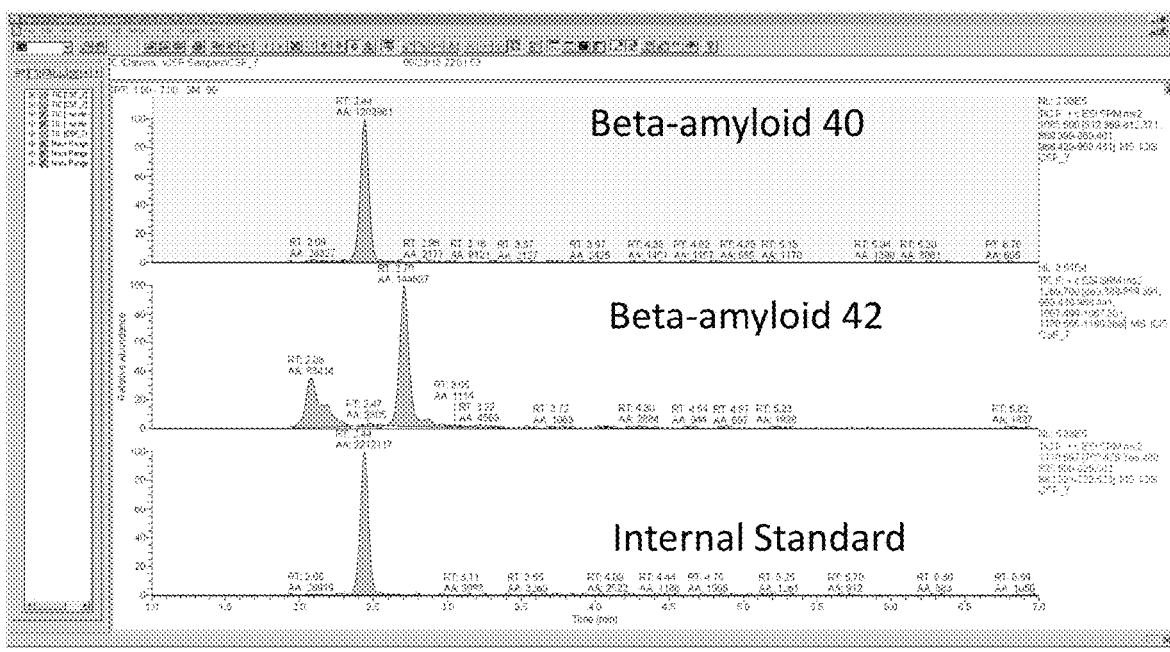

Example patient chromatograms are shown in FIGS. 6 and 7.

Various extractions were compared to optimize recovery of amyloid beta fragments.

TABLE 2

Solid phase extraction recovery comparison

| | Waters MAX | Waters MCX | Waters HLB | Agilent C18 | Phenomenex CX | Thermo SAX |
| --- | --- | --- | --- | --- | --- | --- |
| | | | Abeta 42 SPE Recovery | | | |
| 1 | 181000 | 140244 | 125237 | 3869 | 86088 | 0 |
| 2 | 208763 | 153644 | 113481 | 4629 | 71027 | 0 |
| 3 | 217163 | 153549 | 94726 | 2897 | 111434 | 0 |
| 4 | 238817 | 172517 | 131500 | 1662 | 92846 | 0 |
| MEAN | 211435.75 | 154988.50 | 116236.00 | 3264.25 | 90348.75 | 0 |
| SD | 23916.61 | 13273.14 | 16168.67 | 1281.97 | 16756.17 | |
| % CV | 11.31% | 8.56% | 13.91% | 39.27% | 18.55% | |
| | | | Abeta 40 SPE Recovery | | | |
| 1 | 700570 | 517202 | 305741 | 18287 | 260704 | 0 |
| 2 | 745439 | 534943 | 286890 | 27946 | 218579 | 0 |
| 3 | 824487 | 536441 | 244919 | 2660 | 365956 | 0 |
| 4 | 872219 | 637160 | 305132 | 16695 | 304490 | 0 |
| MEAN | 785678.75 | 556436.50 | 285670.50 | 16397.00 | 287432.25 | 0 |
| SD | 77153.60 | 54520.39 | 28540.89 | 10420.26 | 63013.53 | |
| % CV | 9.82% | 9.80% | 9.99% | 63.55% | 21.92% | |

Waters MAX: mixed mode strong anion exchange → using for final assay validation
Waters MXC: mixed mode strong cation exchange
Waters HLB: silica made for hydrophobic compounds
Agilent C18: typical C18 packing
Phenomenex CX: mixed mode strong cation exchange
Thermo SAX: strong anion exchange Mixed mode strong anion exchange provided the best recovery of amyloid beta fragments.

Urea in the digestion increases recovery of analytes. The following values were determined:

TABLE 3

Recovery comparison for urea vs. no urea

| Runs | No Urea | With Urea |
|---|---|---|
|  | AB42 | Recovery |
| 1 | 15180 | 33397 |
| 2 | 14048 | 29445 |
| 3 | 17908 | 40026 |
| 4 | 14876 | 38011 |
| 5 | 16280 | 37141 |
| MEAN | 15778.00 | 36155.75 |
| SD | 1692.67 | 4634.14 |
| % CV | 10.73% | 12.82% |
|  | AB40 | Recovery |
| 1 | 95675 | 138525 |
| 2 | 97893 | 135433 |
| 3 | 121828 | 186864 |
| 4 | 99755 | 157218 |
| 5 | 128836 | 167420 |
| MEAN | 112078.00 | 161733.75 |
| SD | 15588.07 | 21416.38 |
| % CV | 13.91% | 13.24% |

C4 analytical column was compared with C8 analytical column with respect to sensitivity. C4 column provided superior sensitivity, which is unexpected because C8 and C18 columns are generally preferred in the art. FIG. 11.

Example 4: Assay Reportable Range and Linearity

Figure 4:
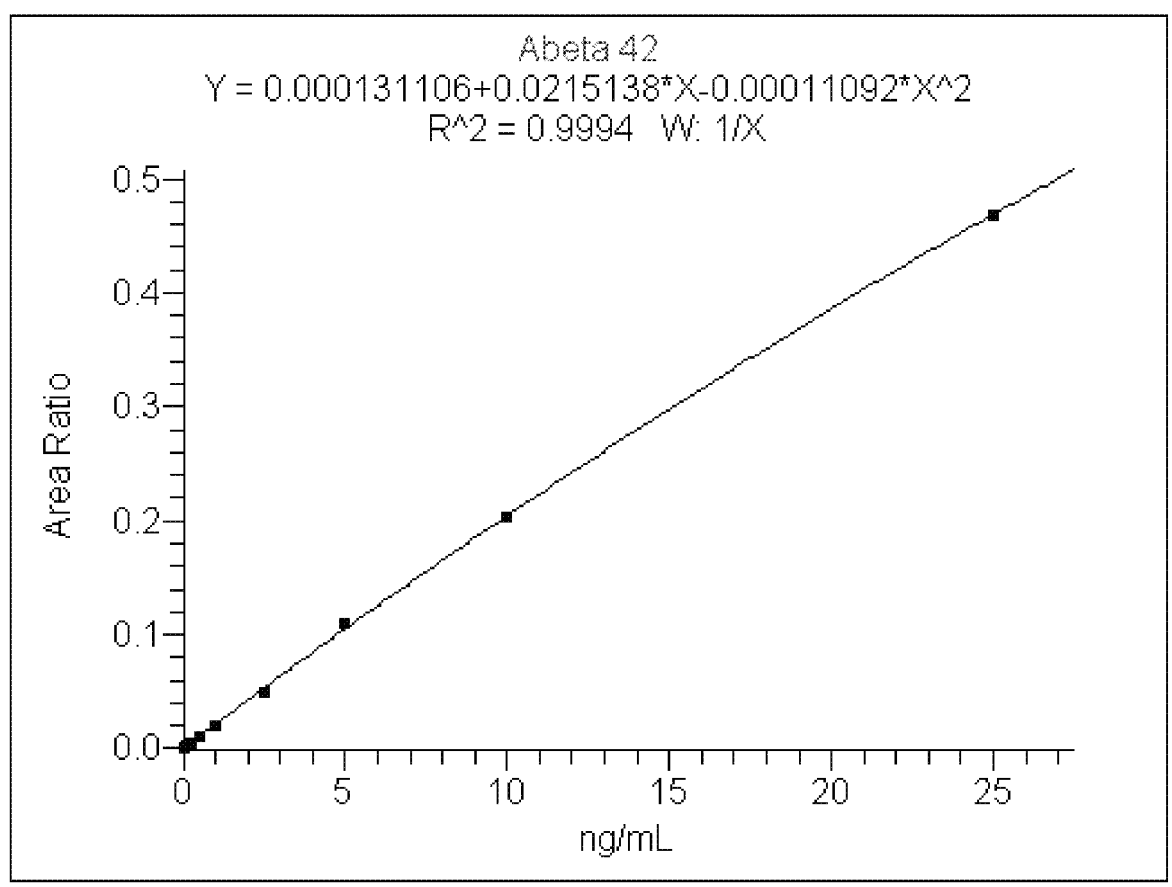
FIG. 4 shows the linear range of Aβ42 analysis.
Figure 5:
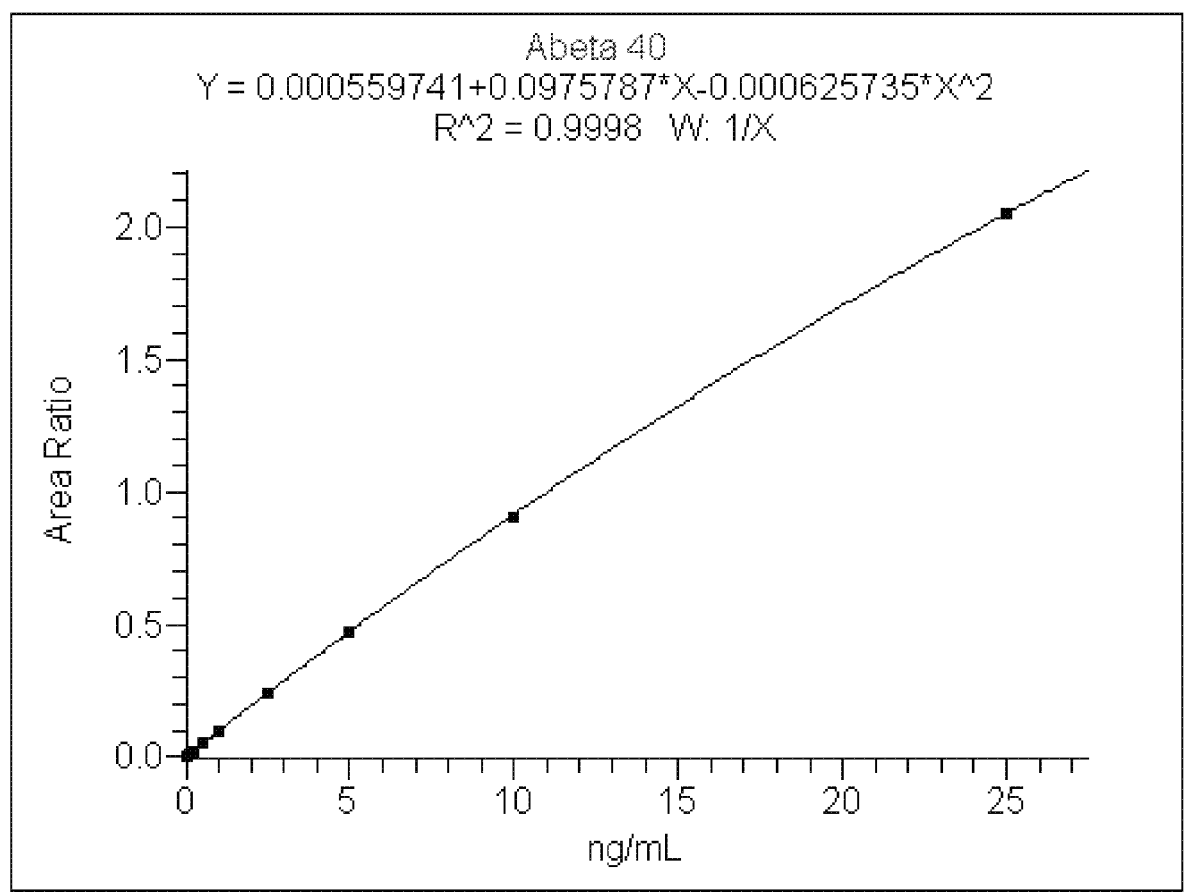
FIG. 5 shows the linear range of Aβ40 analysis.

To establish the linearity of amyloid beta detection in the assay, one blank assigned as zero standard and spiked standards were prepared and analyzed. A quadratic regression from five consecutive runs yielded coefficient correlations of 0.995 or greater, with an accuracy of ±20% revealing a quantifiable linear range of 0.1 to 25 ng/mL. FIGS. 4 and 5.

Example 5: Assay Precision

Reproducibility of a sample within an assay was tested for the following quality control levels:

| Quality Control Level | Beta Amyloid 40 (pg/mL) | Beta Amyloid 42 (pg/mL) |
|---|---|---|
| Low | 750 | 750 |
| Medium | 7500 | 7500 |
| High | 15000 | 15000 |

Within Run Precision: Ten replicates of each quality control were analyzed within a single assay in the following order; low, medium and high.

Acceptability criteria: The % CV should be less than allowable ≤TEa/2. The TEa for this assay is determined to be 30%.

The % CV for Beta Amyloid 40 ranged from 14.31% to 6.55% across all three quality control levels.

The % CV for Beta Amyloid 42 ranged from 14.93% to 7.51% across all three quality control levels.

Total Precision: Data for inter-assay validation was analyzed.

Acceptability criteria: unacceptable if Total SD≥½ TEa or Total SD must be less than a defined maximum SD or CV.

The % CV should be less than allowable ≤TEa/2. The TEa for this assay is determined to be 30%.

The % CV for Beta Amyloid 40 ranged from 10.21% to 4.28% across all three quality control levels.

The % CV for Beta Amyloid 42 ranged from 14.63% to 8.17% across all three quality control levels.

Example 6: Analytical Sensitivity (Detection Limits)

Limit of Blank (LOB): Calculation: LOB=mean of blank+2SD.

Twenty-one matrix blanks were analyzed within a single assay, the back calculated values are then used to calculate the LOB below.

LOB of AB40: 31.32 pg/mL.
LOB of AB42: 32.11 pg/mL.

|  | AB 40 | AB42 |
|---|---|---|
| Run 1 | 22.85 | 3.20 |
| Run 2 | 16.97 | 0.05 |
| Run 3 | 14.62 | 15.31 |
| Run 4 | 37.13 | 19.34 |
| Run 5 | −1.10 | 11.10 |
| Run 6 | 50.10 | 5.28 |
| Run 7 | 9.81 | 15.80 |
| Run 8 | 14.64 | 14.56 |
| Run 9 | 10.31 | 12.74 |
| Run 10 | 5.05 | 19.97 |
| Run 11 | 1.96 | 25.07 |
| Run 12 | 30.81 | 18.98 |
| Run 13 | 16.03 | 28.52 |
| Run 14 | 8.93 | 22.49 |
| Run 15 | 15.77 | 17.91 |
| Run 16 | 4.54 | 43.51 |
| Run 17 | −0.42 | 16.12 |
| Run 18 | 28.03 | 48.73 |
| Run 19 | 48.36 | 36.87 |
| Run 20 | −4.17 | 17.58 |
| Run 21 | 2.30 | −13.54 |
| MEAN | 15.83 | 18.08 |
| SD | 15.49 | 14.03 |
| 2D | 30.97 | 28.07 |
| LOB (Mean + 2D) | 46.81 | 46.14 |

Limit of Detection (LOD): Calculation: LOD=mean of blank+4SD.

Twenty-one matrix blanks were analyzed within a single assay, the back calculated values are then used to calculate the LOD below.

LOD of AB40: 77.78 pg/mL.
LOD of AB42: 74.21 pg/mL.

|  | AB 40 | AB42 |
|---|---|---|
| Run 1 | 22.85 | 3.2 |
| Run 2 | 16.97 | 0.05 |
| Run 3 | 14.62 | 15.31 |
| Run 4 | 37.13 | 19.34 |
| Run 5 | −1.1 | 11.1 |
| Run 6 | 50.1 | 5.28 |
| Run 7 | 9.81 | 15.8 |
| Run 8 | 14.64 | 14.56 |
| Run 9 | 10.31 | 12.74 |
| Run 10 | 5.05 | 19.97 |
| Run 11 | 1.96 | 25.07 |
| Run 12 | 30.81 | 18.98 |
| Run 13 | 16.03 | 28.52 |
| Run 14 | 8.93 | 22.49 |

-continued

|  | AB 40 | AB42 |
|---|---|---|
| Run 15 | 15.77 | 17.91 |
| Run 16 | 4.54 | 43.51 |
| Run 17 | −0.42 | 16.12 |
| Run 18 | 28.03 | 48.73 |
| Run 19 | 48.36 | 36.87 |
| Run 20 | −4.17 | 17.58 |
| Run 21 | 2.3 | −13.54 |
| MEAN | 15.83 | 18.08 |
| SD | 15.49 | 14.03 |
| 4D | 61.95 | 56.14 |
| LOD(Mean + 4D) | 77.78 | 74.21 |

Limit of Quantitation (LOQ): Acceptability criteria: The lowest concentration at which % CV is less than or equal to 2SD when TEa is 30%.

The limit of quantitation for both Beta Amyloid 40 and 42 is determined to be 100 pg/mL.

Example 7: Analyte Measurement Range (AMR)

Acceptability criteria: the average of the observed values should deviate from the expected range by no more than 2SD or 20% CV when TEa is 30%.

The % CV for Beta Amyloid 40 ranges from 6.52 to 12.01% which is deemed acceptable.

The % CV for Beta Amyloid 42 ranges from 6.27 to 14.24% which is deemed acceptable.

| Beta Amyloid 40 Linearity pg/mL | | | | | | | | |
|---|---|---|---|---|---|---|---|---|
|  | 100.00 | 250.00 | 500.00 | 1000.00 | 2500.00 | 5000.00 | 10000.00 | 25000.00 |
| Oct. 30, 2015 | 85.05 | 283.27 | 535.17 | 937.01 | 2491.3 | 5123.81 | 9865.53 | 25029.13 |
| Nov. 17, 2015 | 87.13 | 219.26 | 494 | 866.66 | 2025.84 | 4013.98 | 9356.08 | 23129.34 |
| Nov. 18, 2015 | 89.26 | 265.71 | 408.57 | 788.87 | 2162.14 | 3912.39 | 8316.37 | 19805.85 |
| Nov. 19, 2015 | 108.91 | 268.39 | 440.37 | 910.62 | 2052.88 | 4507.98 | 8741.97 | 20321.97 |
| Nov. 20, 2015 | 106.77 | 237.43 | 470.65 | 813.77 | 2077.58 | 4675.98 | 9212.27 | 21754.94 |
| Nov. 21, 2015 | 85.59 | 237.05 | 423.71 | 790.07 | 1990.27 | 4854.98 | 9211.46 | 22913.33 |
| MEAN | 95.42 | 254.81 | 469.75 | 863.39 | 2161.95 | 4446.83 | 9098.44 | 22008.25 |
| STDev | 11.46 | 25.88 | 48.67 | 62.60 | 191.06 | 496.87 | 592.97 | 2129.60 |
| % CV | 12.01% | 10.16% | 10.36% | 7.25% | 8.84% | 11.17% | 6.52% | 9.68% |
| % Accuracy | 95.42% | 101.92% | 93.95% | 86.34% | 86.48% | 88.94% | 90.98% | 88.03% |

| Beta Amyloid 42 Linearity pg/mL | | | | | | | | |
|---|---|---|---|---|---|---|---|---|
|  | 100.00 | 250.00 | 500.00 | 1000.00 | 2500.00 | 5000.00 | 10000.00 | 25000.00 |
| Oct. 30, 2015 | 92.43 | 264.26 | 496.06 | 1057.47 | 2574.61 | 4444.67 | 10573.78 | 24839.8 |
| Nov. 17, 2015 | 85.02 | 303.85 | 530.61 | 943.81 | 2171.93 | 4542.56 | 10053.91 | 29125.77 |
| Nov. 18, 2015 | 103.46 | 238.3 | 440.25 | 1049.49 | 2484.67 | 5407.8 | 11219.31 | 26659.7 |
| Nov. 19, 2015 | 110.12 | 265.96 | 423.32 | 1069.96 | 2649.92 | 5431.65 | 11713.86 | 26435.43 |
| Nov. 20, 2015 | 120.9 | 299.3 | 417.11 | 1218.6 | 2873.72 | 6253.28 | 12913.34 | 28399.67 |
| Nov. 21, 2015 | 96.04 | 305.84 | 579.06 | 1129.86 | 2459.7 | 6134.47 | 14436.49 | 29514.72 |
| MEAN | 102.39 | 274.33 | 461.47 | 1067.87 | 2550.97 | 5215.99 | 11294.84 | 27092.07 |
| STDev | 14.18 | 27.22 | 49.62 | 98.18 | 256.22 | 742.92 | 1102.35 | 1698.28 |
| % CV | 13.85% | 9.92% | 10.75% | 9.19% | 10.04% | 14.24% | 9.76% | 6.27% |
| % Accuracy | 102.39% | 109.73% | 92.29% | 106.79% | 102.04% | 104.32% | 112.95% | 108.37% |

Example 8: Accuracy

Recovery of known standards.

Acceptability criteria: the error due to lack of perfect recovery (amount recovered MINUS amount added) should be ≤2SD or 15% CV when TEa is 30%.

Six stripped bovine cerebrospinal fluid samples were spiked at the following concentrations: 1000, 2000, 3000, 4000, 8000, and 9000 pg/mL, each spike level was assayed in triplicate.

The six different spike levels were then diluted in 1 to 3 and 1 to 5 ratios using stripped bovine cerebrospinal fluid as the diluent and also assayed in triplicate.

| Pool 1 | | | |
|---|---|---|---|
|  | Baseline | Beta Amyloid 40 Spike Target | pg/mL Observed Concentration |
| Run 1 | 0.00 | 1000.00 | 838.66 |
| Run 2 | 0.00 | 1000.00 | 962.28 |
| Run 3 | 0.00 | 1000.00 | 809.68 |
| MEAN | 0.00 |  | 870.21 |
| STDEV | 0.00 |  | 81.04 |
| % CV | 0.00% |  | 9.31% |
| % Recovery | 0.00% |  | 87.02% |

| Pool 2 | | | |
|---|---|---|---|
|  | Baseline | Beta Amyloid 40 Spike Target | pg/mL Observed Concentration |
| Run 1 | 8.83 | 2000.00 | 1915.62 |
| Run 2 | 0.00 | 2000.00 | 1914.06 |
| Run 3 | 9.04 | 2000.00 | 2053.31 |
| MEAN | 5.96 |  | 1961.00 |
| STDEV | 5.16 |  | 79.95 |
| % CV | 0.00% |  | 4.08% |
| % Recovery | 0.60% |  | 98.05% |

-continued

| Pool 3 | | | |
|---|---|---|---|
|  | Baseline | Beta Amyloid 40 Spike Target | pg/mL Observed Concentration |
| Run 1 | 0 | 3000 | 3170.69 |
| Run 2 | 0 | 3000 | 3285.56 |
| Run 3 | 0 | 3000 | 3565.91 |
| MEAN | 0.00 |  | 3340.72 |
| STDEV | 0.00 |  | 203.30 |

-continued

|  | | |
|---|---|---|
| % CV | 0.00% | 6.09% |
| % Recovery | 0.00% | 111.36% |

Pool 4

|  | Baseline | Beta Amyloid 40 Spike Target | pg/mL Observed Concentration |
|---|---|---|---|
| Run 1 | 46.6 | 4000 | 4605.06 |
| Run 2 | 0 | 4000 | 4686.31 |
| Run 3 | 10.18 | 4000 | 4740.77 |
| MEAN | 18.93 |  | 4677.38 |
| STDEV | 24.50 |  | 68.29 |
| % CV | 0.00% |  | 1.46% |
| % Recovery | 1.89% |  | 116.93% |

Pool 5

|  | Baseline | Beta Amyloid 40 Spike Target | pg/mL Observed Concentration |
|---|---|---|---|
| Run 1 | 14.11 | 7000 | 8051.86 |
| Run 2 | 0 | 7000 | 8013.25 |
| Run 3 | 4.41 | 7000 | 7968.89 |
| MEAN | 6.17 |  | 8011.33 |
| STDEV | 7.22 |  | 41.52 |
| % CV | 0.00% |  | 0.52% |
| % Recovery | 0.62% |  | 100.14% |

Pool 6

|  | Baseline | Beta Amyloid 40 Spike Target | pg/mL Observed Concentration |
|---|---|---|---|
| Run 1 | 0 | 9000 | 9801.28 |
| Run 2 | 6.5 | 9000 | 9152.91 |
| Run 3 | 22.91 | 9000 | 9985.59 |
| MEAN | 9.80 |  | 9646.59 |
| STDEV | 11.81 |  | 437.36 |
| % CV | 0.00% |  | 4.53% |
| % Recovery | 0.98% |  | 107.18% |

Pool 1

|  | Spiked Concentration | Beta Amyloid 40 1:3 dilution target | pg/mL Observed 1:3 Concentration |
|---|---|---|---|
| Run 1 | 838.66 | 279.553 | 254.25 |
| Run 2 | 962.28 | 320.760 | 262.19 |
| Run 3 | 809.68 | 269.893 | 278.28 |
| MEAN | 870.21 | 290.07 | 264.91 |
| STDEV | 81.04 |  | 12.24 |
| % CV | 0.00% |  | 4.62% |
| % Recovery | 87.02% |  | 91.33% |

Pool 2

|  | Spiked Concentration | Beta Amyloid 40 1:3 dilution target | pg/mL Observed 1:3 Concentration |
|---|---|---|---|
| Run 1 | 1915.62 | 638.54 | 814.53 |
| Run 2 | 1914.06 | 638.02 | 668.74 |
| Run 3 | 2053.31 | 684.44 | 740.84 |
| MEAN | 1961.00 | 653.67 | 741.37 |
| STDEV | 79.95 |  | 72.90 |
| % CV | 0.00% |  | 9.83% |
| % Recovery | 98.05% |  | 113.42% |

-continued

Pool 3

|  | Spiked Concentration | Beta Amyloid 40 1:3 dilution target | pg/mL Observed 1:3 Concentration |
|---|---|---|---|
| Run 1 | 3170.69 | 1056.90 | 1063.84 |
| Run 2 | 3285.56 | 1095.19 | 1196.26 |
| Run 3 | 3565.91 | 1188.64 | 1171.08 |
| MEAN | 3340.72 | 1113.57 | 1143.73 |
| STDEV | 203.30 |  | 70.32 |
| % CV | 0.00% |  | 6.15% |
| % Recovery | 111.36% |  | 102.71% |

Pool 4

|  | Spiked Concentration | Beta Amyloid 40 1:3 dilution target | pg/mL Observed 1:3 Concentration |
|---|---|---|---|
| Run 1 | 4605.06 | 1535.02 | 1660.34 |
| Run 2 | 4686.31 | 1562.10 | 1601.44 |
| Run 3 | 4740.77 | 1580.26 | 1761.25 |
| MEAN | 4677.38 | 1559.13 | 1674.34 |
| STDEV | 68.29 |  | 80.82 |
| % CV | 0.00% |  | 4.83% |
| % Recovery | 116.93% |  | 107.39% |

Pool 5

|  | Spiked Concentration | Beta Amyloid 40 1:3 dilution target | pg/mL Observed 1:3 Concentration |
|---|---|---|---|
| Run 1 | 8051.86 | 2683.95 | 2434.11 |
| Run 2 | 8013.25 | 2671.08 | 2554.46 |
| Run 3 | 7968.89 | 2656.30 | 2719.08 |
| MEAN | 8011.33 | 2670.44 | 2569.22 |
| STDEV | 41.52 |  | 143.06 |
| % CV | 0.00% |  | 5.57% |
| % Recovery | 100.14% |  | 96.21% |

Pool 6

|  | Spiked Concentration | Beta Amyloid 40 1:3 dilution target | pg/mL Observed 1:3 Concentration |
|---|---|---|---|
| Run 1 | 9801.28 | 3267.09 | 3594.42 |
| Run 2 | 9152.91 | 3050.97 | 3230.93 |
| Run 3 | 9985.59 | 3328.53 | 3183.79 |
| MEAN | 9646.59 | 3215.53 | 3336.38 |
| STDEV | 437.36 |  | 224.71 |
| % CV | 0.00% |  | 6.74% |
| % Recovery | 107.18% |  | 103.76% |

Pool 1

|  | Spiked Concentration | Beta Amyloid 40 1:5 dilution target | pg/mL Observed 1:5 Concentration |
|---|---|---|---|
| Run 1 | 838.66 | 167.732 | 131.33 |
| Run 2 | 962.28 | 192.456 | 159.46 |
| Run 3 | 809.68 | 161.936 | 153.29 |
| MEAN | 870.21 | 174.04 | 148.03 |
| STDEV | 81.04 |  | 14.79 |
| % CV | 0.00% |  | 9.99% |
| % Recovery | 87.02% |  | 85.05% |

-continued

Pool 2

| | Spiked Concentration | Beta Amyloid 40 1:5 dilution target | pg/mL Observed 1:5 Concentration |
|---|---|---|---|
| Run 1 | 1915.62 | 383.124 | 438.63 |
| Run 2 | 1914.06 | 382.812 | 463.6 |
| Run 3 | 2053.31 | 410.662 | 365.06 |
| MEAN | 1961.00 | 392.20 | 422.43 |
| STDEV | 79.95 | | 51.23 |
| % CV | 0.00% | | 12.13% |
| % Recovery | 98.05% | | 107.71% |

Pool 3

| | Spiked Concentration | Beta Amyloid 40 1:5 dilution target | pg/mL Observed 1:5 Concentration |
|---|---|---|---|
| Run 1 | 3170.69 | 634.138 | 652.44 |
| Run 2 | 3285.56 | 657.112 | 729.65 |
| Run 3 | 3565.91 | 713.182 | 719.26 |
| MEAN | 3340.72 | 668.14 | 700.45 |
| STDEV | 203.30 | | 41.90 |
| % CV | 0.00% | | 5.98% |
| % Recovery | 111.36% | | 104.84% |

Pool 4

| | Spiked Concentration | Beta Amyloid 40 1:5 dilution target | pg/mL Observed 1:5 Concentration |
|---|---|---|---|
| Run 1 | 4605.06 | 921.01 | 974.17 |
| Run 2 | 4686.31 | 937.26 | 1007.06 |
| Run 3 | 4740.77 | 948.15 | 851.34 |
| MEAN | 4677.38 | 935.48 | 944.19 |
| STDEV | 68.29 | | 82.07 |
| % CV | 0.00% | | 8.69% |
| % Recovery | 116.93% | | 100.93% |

Pool 5

| | Spiked Concentration | Beta Amyloid 40 1:5 dilution target | pg/mL Observed 1:5 Concentration |
|---|---|---|---|
| Run 1 | 8051.86 | 1610.37 | 1505.31 |
| Run 2 | 8013.25 | 1602.65 | 1457.53 |
| Run 3 | 7968.89 | 1593.78 | 1579.88 |
| MEAN | 8011.33 | 1602.27 | 1514.24 |
| STDEV | 41.52 | | 61.66 |
| % CV | 0.00% | | 4.07% |
| % Recovery | 100.14% | | 94.51% |

Pool 6

| | Spiked Concentration | Beta Amyloid 40 1:5 dilution target | pg/mL Observed 1:5 Concentration |
|---|---|---|---|
| Run 1 | 9801.28 | 1960.26 | 1709.29 |
| Run 2 | 9152.91 | 1830.58 | 1892.94 |
| Run 3 | 9985.59 | 1997.12 | 1937.85 |
| MEAN | 9646.59 | 1929.32 | 1846.69 |
| STDEV | 437.36 | | 121.09 |
| % CV | 0.00% | | 6.56% |
| % Recovery | 107.18% | | 95.72% |

Pool 1

| | Baseline | Beta Amyloid 42 Spike Target | pg/mL Observed Concentration |
|---|---|---|---|
| Run 1 | 90.26 | 1000.00 | 950.81 |
| Run 2 | 108.39 | 1000.00 | 817.14 |
| Run 3 | 147.57 | 1000.00 | 1017.72 |
| MEAN | 115.41 | | 928.56 |
| STDEV | 29.29 | | 102.12 |
| % CV | 0.00% | | 11.00% |
| % Recovery | 11.54% | | 92.86% |

Pool 2

| | Baseline | Beta Amyloid 42 Spike Target | pg/mL Observed Concentration |
|---|---|---|---|
| Run 1 | 25.38 | 2000.00 | 1638.08 |
| Run 2 | 93.33 | 2000.00 | 1670.63 |
| Run 3 | 39.62 | 2000.00 | 2228.58 |
| MEAN | 52.78 | | 1845.76 |
| STDEV | 35.83 | | 331.93 |
| % CV | 67.90% | | 17.98% |
| % Recovery | 5.28% | | 92.29% |

Pool 3

| | Baseline | Beta Amyloid 42 Spike Target | pg/mL Observed Concentration |
|---|---|---|---|
| Run 1 | 71.92 | 3000 | 3487.59 |
| Run 2 | 47.51 | 3000 | 3425.22 |
| Run 3 | 45.29 | 3000 | 3393.22 |
| MEAN | 54.91 | | 3435.34 |
| STDEV | 14.78 | | 47.99 |
| % CV | 26.91% | | 1.40% |
| % Recovery | 5.49% | | 114.51% |

Pool 4

| | Baseline | Beta Amyloid 42 Spike Target | pg/mL Observed Concentration |
|---|---|---|---|
| Run 1 | 71.04 | 4000 | 4391.79 |
| Run 2 | 151.45 | 4000 | 4753.15 |
| Run 3 | 92.7 | 4000 | 4293.59 |
| MEAN | 105.06 | | 4479.51 |
| STDEV | 41.61 | | 242.01 |
| % CV | 39.60% | | 5.40% |
| % Recovery | 10.51% | | 111.99% |

Pool 5

| | Baseline | Beta Amyloid 42 Spike Target | pg/mL Observed Concentration |
|---|---|---|---|
| Run 1 | 56.28 | 7000 | 7709.11 |
| Run 2 | 165.35 | 7000 | 7167.68 |
| Run 3 | 85.57 | 7000 | 7688.12 |
| MEAN | 102.40 | | 7521.64 |
| STDEV | 56.45 | | 306.72 |
| % CV | 55.13% | | 4.08% |
| % Recovery | 10.24% | | 107.45% |

Pool 6

| | Baseline | Beta Amyloid 42 Spike Target | pg/mL Observed Concentration |
|---|---|---|---|
| Run 1 | 103.51 | 9000 | 8046.03 |
| Run 2 | 103.28 | 9000 | 7652.79 |
| Run 3 | 67.54 | 9000 | 7382.95 |
| MEAN | 91.44 | | 7693.92 |
| STDEV | 20.70 | | 333.45 |

|  |  |  |
|---|---|---|
| % CV | 22.64% | 4.33% |
| % Recovery | 9.14% | 85.49% |

Pool 1

|  | Spiked Concentration | Beta Amyloid 42 1:3 dilution target | pg/mL Observed 1:3 Concentration |
|---|---|---|---|
| Run 1 | 950.81 | 316.937 | 286.23 |
| Run 2 | 817.14 | 272.380 | 290.73 |
| Run 3 | 1017.72 | 339.240 | 306.73 |
| MEAN | 928.56 | 309.52 | 294.56 |
| STDEV | 102.12 |  | 10.77 |
| % CV | 0.00% |  | 3.66% |
| % Recovery | 92.86% |  | 95.17% |

Pool 2

|  | Spiked Concentration | Beta Amyloid 42 1:3 dilution target | pg/mL Observed 1:3 Concentration |
|---|---|---|---|
| Run 1 | 1638.08 | 546.03 | 747.89 |
| Run 2 | 1670.63 | 556.88 | 748.99 |
| Run 3 | 2228.58 | 742.86 | 688.05 |
| MEAN | 1845.76 | 615.25 | 728.31 |
| STDEV | 331.93 |  | 34.87 |
| % CV | 0.00% |  | 4.79% |
| % Recovery | 184.58% |  | 118.38% |

Pool 3

|  | Spiked Concentration | Beta Amyloid 42 1:3 dilution target | pg/mL Observed 1:3 Concentration |
|---|---|---|---|
| Run 1 | 3487.59 | 1162.53 | 1092.18 |
| Run 2 | 3425.22 | 1141.74 | 1287.53 |
| Run 3 | 3393.22 | 1131.07 | 1005.49 |
| MEAN | 3435.34 | 1145.11 | 1128.40 |
| STDEV | 47.99 |  | 144.47 |
| % CV | 0.00% |  | 12.80% |
| % Recovery | 343.53% |  | 98.54% |

Pool 4

|  | Spiked Concentration | Beta Amyloid 42 1:3 dilution target | pg/mL Observed 1:3 Concentration |
|---|---|---|---|
| Run 1 | 4391.79 | 1463.93 | 1715.75 |
| Run 2 | 4753.15 | 1584.38 | 1652.65 |
| Run 3 | 4293.59 | 1431.20 | 1664.18 |
| MEAN | 4479.51 | 1493.17 | 1677.53 |
| STDEV | 242.01 |  | 33.60 |
| % CV | 0.00% |  | 2.00% |
| % Recovery | 447.95% |  | 112.35% |

Pool 5

|  | Spiked Concentration | Beta Amyloid 42 1:3 dilution target | pg/mL Observed 1:3 Concentration |
|---|---|---|---|
| Run 1 | 7709.11 | 2569.70 | 2112.71 |
| Run 2 | 7167.68 | 2389.23 | 2256.35 |
| Run 3 | 7688.12 | 2562.71 | 2377.18 |
| MEAN | 7521.64 | 2507.21 | 2248.75 |
| STDEV | 306.72 |  | 132.40 |
| % CV | 0.00% |  | 5.89% |
| % Recovery | 752.16% |  | 89.69% |

Pool 6

|  | Spiked Concentration | Beta Amyloid 42 1:3 dilution target | pg/mL Observed 1:3 Concentration |
|---|---|---|---|
| Run 1 | 8046.03 | 2682.01 | 3205.47 |
| Run 2 | 7652.79 | 2550.93 | 3178.28 |
| Run 3 | 7382.95 | 2460.98 | 2754.6 |
| MEAN | 7693.92 | 2564.64 | 3046.12 |
| STDEV | 333.45 |  | 252.83 |
| % CV | 0.00% |  | 8.30% |
| % Recovery | 769.39% |  | 118.77% |

Pool 1

|  | Spiked Concentration | Beta Amyloid 42 1:5 dilution target | pg/mL Observed 1:5 Concentration |
|---|---|---|---|
| Run 1 | 950.81 | 190.162 | 185.77 |
| Run 2 | 817.14 | 163.428 | 210.57 |
| Run 3 | 1017.72 | 203.544 | 150.73 |
| MEAN | 928.56 | 185.71 | 182.36 |
| STDEV | 102.12 |  | 30.07 |
| % CV | 0.00% |  | 16.49% |
| % Recovery | 92.86% |  | 98.19% |

Pool 2

|  | Spiked Concentration | Beta Amyloid 42 1:5 dilution target | pg/mL Observed 1:5 Concentration |
|---|---|---|---|
| Run 1 | 1638.08 | 327.616 | 482.86 |
| Run 2 | 1670.63 | 334.126 | 415.91 |
| Run 3 | 2228.58 | 445.716 | 407.04 |
| MEAN | 1845.76 | 369.15 | 435.27 |
| STDEV | 331.93 |  | 41.45 |
| % CV | 0.00% |  | 9.52% |
| % Recovery | 184.58% |  | 117.91% |

Pool 3

|  | Spiked Concentration | Beta Amyloid 42 1:5 dilution target | pg/mL Observed 1:5 Concentration |
|---|---|---|---|
| Run 1 | 3487.59 | 697.518 | 832.7 |
| Run 2 | 3425.22 | 685.044 | 686.42 |
| Run 3 | 3393.22 | 678.644 | 731.34 |
| MEAN | 3435.34 | 687.07 | 750.15 |
| STDEV | 47.99 |  | 74.93 |
| % CV | 0.00% |  | 9.99% |
| % Recovery | 343.53% |  | 109.18% |

Pool 4

|  | Spiked Concentration | Beta Amyloid 42 1:5 dilution target | pg/mL Observed 1:5 Concentration |
|---|---|---|---|
| Run 1 | 4391.79 | 878.36 | 875.68 |
| Run 2 | 4753.15 | 950.63 | 1049.24 |
| Run 3 | 4293.59 | 858.72 | 936.27 |
| MEAN | 4479.51 | 895.90 | 953.73 |
| STDEV | 242.01 |  | 88.09 |
| % CV | 0.00% |  | 9.24% |
| % Recovery | 447.95% |  | 106.45% |

| Pool 5 | | |
|---|---|---|
| | Beta Amyloid 42 | pg/mL |
| Spiked Concentration | 1:5 dilution target | Observed 1:5 Concentration |
| Run 1 | 7709.11 | 1541.82 | 1323.74 |
| Run 2 | 7167.68 | 1433.54 | 1343.62 |
| Run 3 | 7688.12 | 1537.62 | 1520.6 |
| MEAN | 7521.64 | 1504.33 | 1395.99 |
| STDEV | 306.72 | | 108.38 |
| % CV | 0.00% | | 7.76% |
| % Recovery | 752.16% | | 92.80% |

| Pool 6 | | |
|---|---|---|
| | Beta Amyloid 42 | pg/mL |
| Spiked Concentration | 1:5 dilution target | Observed 1:5 Concentration |
| Run 1 | 8046.03 | 1609.21 | 1496.34 |
| Run 2 | 7652.79 | 1530.56 | 1637.96 |
| Run 3 | 7382.95 | 1476.59 | 1439.48 |
| MEAN | 7693.92 | 1538.78 | 1524.59 |
| STDEV | 333.45 | | 102.21 |
| % CV | 0.00% | | 6.70% |
| % Recovery | 769.39% | | 99.08% |

Example 9: Specimen Stability

Acceptability criteria: A sample is considered stable as long as the average difference between the baseline value and the time/temperature sample value is ≤TEa/2 for that analyte when TEa equals 30%.

Freeze/Thaw Stability: Freeze thaw analysis was conducted by analyzed six patient pools which were divided into four even aliquots. All four aliquots of each patient pool were frozen at −60 to −80° C. Aliquots two through four were thawed to ambient temperature of 18-26° C. and frozen. Aliquots three and four were thawed to ambient temperature of 18-26° C. and frozen. Aliquot four was then thawed to ambient temperature 18-26° C. and frozen.

All aliquots were thawed a final time to ambient temperature 18-26° C. and analyzed in technical triplicate. Freeze thaw analysis contains data across three freeze thaw cycles.

Beta Amyloid 40 and Beta Amyloid 42 have acceptable stability up to two freeze thaw cycles.

| | Beta Amyloid 40 pg/mL Patient Pool 1 | | | | | Beta Amyloid 40 pg/mL Patient Pool 2 | | | |
|---|---|---|---|---|---|---|---|---|---|
| | Baseline | 1 FT | 2 FT | 3 FT | | Baseline | 1 FT | 2 FT | 3 FT |
| Run 1 | 9373.43 | 9530.94 | 10628.69 | 11600.31 | Run 1 | 11223.67 | 12887.34 | 13027.4 | 14939.98 |
| Run 2 | 8513.86 | 9019.69 | 9464.10 | 11372.90 | Run 2 | 11846.93 | 12478.66 | 12160.87 | 13997.01 |
| Run 3 | 9761.12 | 9962.20 | 10505.74 | 9878.65 | Run 3 | 12335.26 | 12993.07 | 13471.64 | 13398.56 |
| MEAN | 9216.14 | 9504.28 | 10199.51 | 10950.62 | MEAN | 11801.95 | 12786.36 | 12886.64 | 14111.85 |
| STDEV | 638.33 | 471.82 | 639.84 | 935.29 | STDEV | 557.16 | 271.67 | 666.63 | 777.10 |
| % CV | 6.93% | 4.96% | 6.27% | 8.54% | % CV | 4.72% | 2.12% | 5.17% | 5.51% |
| % Recovery | | 103.13% | 110.67% | 118.82% | % Recovery | | 108.34% | 109.19% | 119.57% |
| Total Mean | 9967.64 | | | | Total Mean | 12896.70 | | | |
| Total RSD | 192.84 | | | | Total RSD | 217.09 | | | |
| Total % CV | 6.68% | | | | Total % CV | 4.38% | | | |
| Total % Recovery | 110.87% | | | | Total % Recovery | 112.37% | | | |

| | Beta Amyloid 40 pg/mL Patient Pool 1 | | | | | Beta Amyloid 42 pg/mL Patient Pool 2 | | | |
|---|---|---|---|---|---|---|---|---|---|
| | Baseline | 1 FT | 2 FT | 3 FT | | Baseline | 1 FT | 2 FT | 3 FT |
| Run 1 | 1757.99 | 1957.06 | 1853.56 | 1368.85 | Run 1 | 2091.28 | 2404.1 | 2882.04 | 2752.87 |
| Run 2 | 1847.99 | 1999.14 | 1698.65 | 1802.71 | Run 2 | 2838.46 | 3106.10 | 3110.09 | 2816.83 |
| Run 3 | 1943.11 | 2227.49 | 1954.92 | 1741.27 | Run 3 | 2826.06 | 3196.47 | 2911.49 | 2719.64 |
| MEAN | 1849.70 | 2061.23 | 1835.71 | 1637.61 | MEAN | 2585.27 | 2902.22 | 2967.87 | 2763.11 |
| STDEV | 92.57 | 145.51 | 129.06 | 234.77 | STDEV | 427.85 | 433.75 | 124.04 | 49.40 |
| % CV | 5.00% | 7.06% | 7.03% | 14.34% | % CV | 16.55% | 14.95% | 4.18% | 1.79% |
| % Recovery | | 111.44% | 99.24% | 88.53% | % Recovery | | 112.26% | 114.80% | 106.88% |
| Total Mean | 1846.06 | | | | Total Mean | 2804.62 | | | |
| Total RSD | 60.39 | | | | Total RSD | 200.99 | | | |
| Total % CV | 8.36% | | | | Total % CV | 9.37% | | | |
| Total % Recovery | 99.74% | | | | Total % Recovery | 111.31% | | | |

| | Beta Amyloid 40 pg/mL Patient Pool 3 | | | | | Beta Amyloid 40 pg/mL Patient Pool 4 | | | |
|---|---|---|---|---|---|---|---|---|---|
| | Baseline | 1 FT | 2 FT | 3 FT | | Baseline | 1 FT | 2 FT | 3 FT |
| Run 1 | 13810.48 | 14226.23 | 16054.51 | 18419.42 | Run 1 | 10459.48 | 11019.24 | 12030.76 | 14514 |
| Run 2 | 13737.02 | 14534.24 | 14958.05 | 17319.53 | Run 2 | 10458.44 | 10590.22 | 11132.77 | 13398.93 |
| Run 3 | 13395.15 | 14799.34 | 16085.07 | 17381.51 | Run 3 | 9700.34 | 10566.41 | 13475.75 | 11460.96 |
| MEAN | 13647.55 | 14519.94 | 15699.21 | 17706.82 | MEAN | 10206.09 | 10725.29 | 12213.09 | 13124.63 |
| STDEV | 221.65 | 286.82 | 642.05 | 617.91 | STDEV | 437.99 | 254.85 | 1182.08 | 1544.89 |
| % CV | 1.62% | 1.98% | 4.09% | 3.49% | % CV | 4.29% | 2.38% | 9.68% | 11.77% |
| % Recovery | | 106.39% | 115.03% | 124.74% | % Recovery | | 105.09% | 119.66% | 128.60% |
| Total Mean | 15393.38 | | | | Total Mean | 11567.28 | | | |
| Total RSD | 218.78 | | | | Total RSD | 610.20 | | | |

| | | | | | | | | |
|---|---|---|---|---|---|---|---|---|
| Total % CV | 2.79% | | | | Total % CV | 7.03% | | |
| Total % Recovery | 117.06% | | | | Total % Recovery | 117.78% | | |

| | Beta Amyloid 42 pg/mL Patient Pool 3 | | | | | Beta Amyloid 42 pg/mL Patient Pool 4 | | |
|---|---|---|---|---|---|---|---|---|
| | Baseline | 1 FT | 2 FT | 3 FT | | Baseline | 1 FT | 2 FT |
| Run 1 | 2211.66 | 2283.84 | 2641.04 | 1982.94 | Run 1 | 1931.24 | 2499.50 | 2308.20 |
| Run 2 | 2521.34 | 2687.66 | 2485.89 | 2457.18 | Run 2 | 2771.11 | 2183.09 | 2418.84 |
| Run 3 | 1849.56 | 2217.48 | 2504.98 | 2390.17 | Run 3 | 2320.90 | 2260.08 | 1772.90 |
| MEAN | 2194.19 | 2396.33 | 2543.97 | 2276.76 | MEAN | 2341.08 | 2314.22 | 2166.65 |
| STDEV | 336.23 | 254.47 | 84.61 | 256.65 | STDEV | 420.30 | 165.01 | 345.45 |
| % CV | 15.32% | 10.62% | 3.33% | 11.27% | % CV | 17.95% | 7.13% | 15.94% |
| % Recovery | | 109.21% | 115.94% | 103.76% | % Recovery | | 98.85% | 92.55% |
| Total Mean | 2352.81 | | | | Total Mean | 2273.98 | | |
| Total RSD | 105.98 | | | | Total RSD | 131.24 | | |
| Total % CV | 10.14% | | | | Total % CV | 13.68% | | |
| Total % Recovery | 109.64% | | | | Total % Recovery | 95.70% | | |

| | Beta Amyloid 40 pg/mL Patient Pool 5 | | | | | Beta Amyloid 40 pg/mL Patient Pool 6 | | | |
|---|---|---|---|---|---|---|---|---|---|
| | Baseline | 1 FT | 2 FT | 3 FT | | Baseline | 1 FT | 2 FT | 3 FT |
| Run 1 | 10636.38 | 11289.21 | 12568.68 | 14488.23 | Run 1 | 10743.46 | 11195.73 | 12151.77 | 12151.77 |
| Run 2 | 10219.63 | 10610.52 | 11752.49 | 14421 | Run 2 | 9924.85 | 10721.24 | 12368.51 | 12368.51 |
| Run 3 | 10973.86 | 10517.58 | 13479.79 | 12081.94 | Run 3 | 11094.19 | 10635.12 | 12526.26 | 13027.58 |
| MEAN | 10609.96 | 10805.77 | 12600.32 | 13663.72 | MEAN | 10587.50 | 10850.70 | 12348.85 | 12515.95 |
| STDEV | 377.81 | 421.24 | 864.08 | 1370.28 | STDEV | 600.07 | 301.89 | 188.02 | 456.14 |
| % CV | 3.56% | 3.90% | 6.86% | 10.03% | % CV | 5.67% | 2.78% | 1.52% | 3.64% |
| % Recovery | | 101.85% | 118.76% | 128.78% | % Recovery | | 102.49% | 116.64% | 118.21% |
| Total Mean | 11919.94 | | | | Total Mean | 11575.75 | | | |
| Total RSD | 463.35 | | | | Total RSD | 179.83 | | | |
| Total % CV | 6.09% | | | | Total % CV | 3.40% | | | |
| Total % Recovery | 116.46% | | | | Total % Recovery | 112.45% | | | |

| | Beta Amyloid 42 pg/mL Patient Pool 5 | | | | | Beta Amyloid 42 pg/mL Patient Pool 6 | | | |
|---|---|---|---|---|---|---|---|---|---|
| | Baseline | 1 FT | 2 FT | 3 FT | | Baseline | 1 FT | 2 FT | 3 FT |
| Run 1 | 2126.51 | 2246.83 | 2749.21 | 2501.28 | Run 1 | 2027.03 | 1966.27 | 2348.20 | 2236.04 |
| Run 2 | 2423.15 | 2325.82 | 2979.89 | 2698.43 | Run 2 | 2179.57 | 2086.16 | 2302.52 | 2256.19 |
| Run 3 | 2937.29 | 2138.08 | 2621.43 | 2671.59 | Run 3 | 2579.21 | 2128.10 | 2094.63 | 1809.31 |
| MEAN | 2495.65 | 2236.91 | 2783.51 | 2623.77 | MEAN | 2261.94 | 2060.18 | 2248.45 | 2100.51 |
| STDEV | 410.22 | 94.26 | 181.67 | 106.92 | STDEV | 285.16 | 83.99 | 135.16 | 252.39 |
| % CV | 16.44% | 4.21% | 6.53% | 4.08% | % CV | 12.61% | 4.08% | 6.01% | 12.02% |
| % Recovery | | 89.63% | 111.53% | 105.13% | % Recovery | | 91.08% | 99.40% | 92.86% |
| Total Mean | 2534.96 | | | | Total Mean | 2167.77 | | | |
| Total RSD | 146.47 | | | | Total RSD | 95.20 | | | |
| Total % CV | 7.81% | | | | Total % CV | 8.68% | | | |
| Total % Recovery | 102.10% | | | | Total % Recovery | 94.45% | | | |

Extracted Sample Stability: Ten samples were analyzed the same day as sample extraction for a baseline value. The next day, the same samples were re-injected for analysis against the baseline values.

Beta Amyloid 40 and 42 shows extracted sample stability up to 1 day at 4° C. in the C-stack of the CTC Autosampler.

| | Beta Amyloid 40 pg/mL | | | | | |
|---|---|---|---|---|---|---|
| | Baseline | 1 day | MEAN | SD | % CV | % Recovery |
| Sample 1 | 0.10 | 0.11 | 0.11 | 0.01 | 6.73% | 110.00% |
| Sample 2 | 0.21 | 0.22 | 0.22 | 0.01 | 3.29% | 104.76% |
| Sample 3 | 0.49 | 0.52 | 0.51 | 0.02 | 4.20% | 106.12% |

-continued

| | Beta Amyloid 40 pg/mL | | | | | |
|---|---|---|---|---|---|---|
| | Baseline | 1 day | MEAN | SD | % CV | % Recovery |
| Sample 4 | 1.17 | 1.07 | 1.12 | 0.07 | 6.31% | 91.45% |
| Sample 5 | 2.90 | 2.86 | 2.88 | 0.03 | 0.98% | 98.62% |
| Sample 6 | 4.62 | 5.20 | 4.91 | 0.41 | 8.35% | 112.55% |
| Sample 7 | 25.07 | 25.37 | 25.22 | 0.21 | 0.84% | 101.20% |
| Sample 8 | 0.80 | 0.76 | 0.78 | 0.03 | 3.63% | 95.00% |
| Sample 9 | 8.17 | 8.02 | 8.10 | 0.11 | 1.31% | 98.16% |
| Sample 10 | 16.24 | 14.33 | 15.29 | 1.35 | 8.84% | 88.24% |

Refrigerated Stability (2.0 to 8.0° C.): Samples have shown to be stable refrigerated for up to 5 days.

| POOL 1 Beta Amyloid 40 600 pg/mL | | | | | | | |
|---|---|---|---|---|---|---|---|
| | Replicate 1 | Replicate 2 | Replicate 2 | MEAN | SD | % CV | % Recovery |
| Baseline | 779.29 | 738.39 | 583.39 | 700.36 | 103.34 | 14.76% | 116.73% |
| Day 1 | 658.23 | 659.68 | 776.3 | 698.07 | 67.75 | 9.71% | 116.35% |
| Day 3 | 767.06 | 713.26 | 658.66 | 712.99 | 54.20 | 7.60% | 118.83% |
| Day 5 | 678.63 | 749.03 | 649.66 | 692.44 | 51.10 | 7.38% | 115.41% |
| Day 7 | 693.77 | 703.42 | 733.24 | 710.14 | 20.58 | 2.90% | 118.36% |
| Day 14 | 946.19 | 831.81 | 730.22 | 836.07 | 108.05 | 12.92% | 139.35% |
| Day 21 | 599.04 | 608.87 | 678.33 | 628.75 | 43.22 | 6.87% | 104.79% |
| Day 31 | 640.92 | 745.31 | 741.69 | 709.31 | 59.25 | 8.35% | 118.22% |

| POOL 2 Beta Amyloid 40 3000 pg/mL | | | | | | | |
|---|---|---|---|---|---|---|---|
| | Replicate 1 | Replicate 2 | Replicate 2 | MEAN | SD | % CV | % Recovery |
| Baseline | 3095.88 | 2786.21 | 2749.96 | 2877.35 | 190.12 | 6.61% | 95.91% |
| Day 1 | 3088.14 | 3270.74 | 2975.15 | 3111.34 | 149.15 | 4.79% | 103.71% |
| Day 3 | 2673.9 | 3470.73 | 3293.98 | 3146.20 | 418.47 | 13.30% | 104.87% |
| Day 5 | 2965.85 | 2791.08 | 3209.31 | 2988.75 | 210.05 | 7.03% | 99.62% |
| Day 7 | 3019.89 | 3405.5 | 3197.44 | 3207.61 | 193.01 | 6.02% | 106.92% |
| Day 14 | 3112.61 | 2942.44 | 2878.28 | 2977.78 | 121.10 | 4.07% | 99.26% |
| Day 21 | 3339.29 | 3159.82 | 2795.68 | 3098.26 | 276.98 | 8.94% | 103.28% |
| Day 31 | 3063.34 | 3238.69 | 2775.26 | 3025.76 | 233.99 | 7.73% | 100.86% |

| POOL 3 Beta Amyloid 40 pg/mL 9000 pg/mL | | | | | | | |
|---|---|---|---|---|---|---|---|
| | Replicate 1 | Replicate 2 | Replicate 2 | MEAN | SD | % CV | % Recovery |
| Baseline | 8599.60 | 9082.10 | 9287.20 | 8989.63 | 353.00 | 3.93% | 99.88% |
| Day 1 | 8136.03 | 8785.38 | 7959.96 | 8293.79 | 434.74 | 5.24% | 92.15% |
| Day 3 | 8802.53 | 10914.81 | 8954.65 | 9557.33 | 1178.07 | 12.33% | 106.19% |
| Day 5 | 8703.29 | 9246.50 | 8335.09 | 8761.63 | 458.50 | 5.23% | 97.35% |
| Day 7 | 7697.84 | 9428.17 | 8620.20 | 8582.07 | 865.79 | 10.09% | 95.36% |
| Day 14 | 8247.15 | 8505.88 | 8240.75 | 8331.26 | 151.26 | 1.82% | 92.57% |
| Day 21 | 8162.27 | 8182.13 | 7900.43 | 8081.61 | 157.22 | 1.95% | 89.80% |
| Day 31 | 7765.88 | 8581.78 | 8139.16 | 8162.27 | 408.44 | 5.00% | 90.69% |

| POOL 4 Beta Amyloid 40 pg/mL 1200 pg/mL | | | | | | | |
|---|---|---|---|---|---|---|---|
| | Replicate 1 | Replicate 2 | Replicate 2 | MEAN | SD | % CV | % Recovery |
| Baseline | 1083.17 | 1007.45 | 1237.13 | 1109.25 | 117.04 | 10.55% | 92.44% |
| Day 1 | 1019.62 | 1283.73 | 1116.96 | 1140.10 | 133.57 | 11.72% | 95.01% |
| Day 3 | 1216.89 | 1249.03 | 1062.99 | 1176.30 | 99.44 | 8.45% | 98.03% |
| Day 5 | 1129.71 | 1132.32 | 1084.54 | 1115.52 | 26.86 | 2.41% | 92.96% |
| Day 7 | 1071.05 | 1096.81 | 1101.76 | 1089.87 | 16.49 | 1.51% | 90.82% |
| Day 14 | 993.74 | 1148.19 | 1065.45 | 1069.13 | 77.29 | 7.23% | 89.09% |
| Day 21 | 1153.51 | 1150.47 | 1201.11 | 1168.36 | 28.40 | 2.43% | 97.36% |
| Day 31 | 1146.57 | 1141.36 | 999.53 | 1095.82 | 83.43 | 7.61% | 91.32% |

| POOL 5 Beta Amyloid 40 pg/mL 6000 pg/mL | | | | | | | |
|---|---|---|---|---|---|---|---|
| | Replicate 1 | Replicate 2 | Replicate 2 | MEAN | SD | % CV | % Recovery |
| Baseline | 6677.96 | 6380.35 | 6933.19 | 6663.83 | 276.69 | 4.15% | 111.06% |
| Day 1 | 5355.05 | 5489.45 | 6317.58 | 5720.69 | 521.27 | 9.11% | 95.34% |
| Day 3 | 5620.59 | 6561.63 | 6009.07 | 6063.76 | 472.90 | 7.80% | 101.06% |
| Day 5 | 5395.23 | 5481.01 | 5842.92 | 5573.05 | 237.61 | 4.26% | 92.88% |
| Day 7 | 5555.9 | 5810.19 | 5689.14 | 5685.08 | 127.19 | 2.24% | 94.75% |
| Day 14 | 6075.72 | 5873.62 | 5753.26 | 5900.87 | 162.95 | 2.76% | 98.35% |

| | | | | | | | |
|---|---|---|---|---|---|---|---|
| Day 21 | 5702.75 | 6152.04 | 5739.07 | 5864.62 | 249.57 | 4.26% | 97.74% |
| Day 31 | 5495.09 | 6234.34 | 5814.4 | 5847.94 | 370.76 | 6.34% | 97.47% |

POOL 6 Beta Amyloid 40 20000 pg/mL

| | Replicate 1 | Replicate 2 | Replicate 2 | MEAN | SD | % CV | % Recovery |
|---|---|---|---|---|---|---|---|
| Baseline | 20310.45 | 20876.37 | 21447.84 | 20878.22 | 568.70 | 2.72% | 104.39% |
| Day 1 | 17537.07 | 19362.34 | 19307.88 | 18735.76 | 1038.46 | 5.54% | 93.68% |
| Day 3 | 18592.96 | 19095.83 | 20956.09 | 19548.29 | 1244.84 | 6.37% | 97.74% |
| Day 5 | 17915.26 | 17751.53 | 18930.57 | 18199.12 | 638.72 | 3.51% | 91.00% |
| Day 7 | 19548.87 | 18232.47 | 18022.25 | 18601.20 | 827.41 | 4.45% | 93.01% |
| Day 14 | 16869.19 | 18533.17 | 18083.45 | 17828.60 | 860.77 | 4.83% | 89.14% |
| Day 21 | 18377.09 | 18761.43 | 19195.86 | 18778.13 | 409.64 | 2.18% | 93.89% |
| Day 31 | 18050.69 | 18667.82 | 18603.41 | 18440.64 | 339.24 | 1.84% | 92.20% |

POOL 1 Beta Amyloid 42 600 pg/mL

| | Replicate 1 | Replicate 2 | Replicate 2 | MEAN | SD | % CV | % Recovery |
|---|---|---|---|---|---|---|---|
| Baseline | 715.19 | 711.63 | 597.55 | 674.79 | 66.92 | 9.92% | 112.47% |
| Day 1 | 637.32 | 664.25 | 592.10 | 631.22 | 36.46 | 5.78% | 105.20% |
| Day 3 | 637.32 | 681.03 | 640.01 | 652.79 | 24.50 | 3.75% | 108.80% |
| Day 5 | 521.06 | 655.35 | 641.83 | 606.08 | 73.94 | 12.20% | 101.01% |
| Day 7 | 548.16 | 688.76 | 694.50 | 643.81 | 82.88 | 12.87% | 107.30% |
| Day 14 | 793.24 | 708.37 | 745.63 | 749.08 | 42.54 | 5.68% | 124.85% |
| Day 21 | 456.42 | 530.45 | 520.18 | 502.35 | 40.11 | 7.98% | 83.73% |
| Day 31 | 596.89 | 729.56 | 636.46 | 654.30 | 68.11 | 10.41% | 109.05% |

POOL 2 Beta Amyloid 42 3000 pg/mL

| | Replicate 1 | Replicate 2 | Replicate 2 | MEAN | SD | % CV | % Recovery |
|---|---|---|---|---|---|---|---|
| Baseline | 2948.02 | 2894.12 | 3253.65 | 3031.93 | 193.90 | 6.40% | 101.06% |
| Day 1 | 2362.8 | 2918.64 | 2765.25 | 2682.23 | 287.07 | 10.70% | 89.41% |
| Day 3 | 2511.77 | 2628.37 | 2544.33 | 2561.49 | 60.16 | 2.35% | 85.38% |
| Day 5 | 2815.34 | 2710.19 | 2739.48 | 2755.00 | 54.27 | 1.97% | 91.83% |
| Day 7 | 2214.73 | 2551.56 | 2602.08 | 2456.12 | 210.57 | 8.57% | 81.87% |
| Day 14 | 2005.43 | 1967.07 | 2122.07 | 2031.52 | 80.73 | 3.97% | 67.72% |
| Day 21 | 2925.33 | 2407.52 | 2575.49 | 2636.11 | 264.17 | 10.02% | 87.87% |
| Day 31 | 1887.95 | 2061.06 | 2050.62 | 1999.88 | 97.07 | 4.85% | 66.66% |

POOL 3 Beta Amyloid 42 pg/mL 9000 pg/mL

| | Replicate 1 | Replicate 2 | Replicate 2 | MEAN | SD | % CV | % Recovery |
|---|---|---|---|---|---|---|---|
| Baseline | 7683.62 | 7786.05 | 7986.82 | 7818.83 | 154.24 | 1.97% | 86.88% |
| Day 1 | 7746.48 | 6971.53 | 9102.61 | 7940.21 | 1078.67 | 13.58% | 88.22% |
| Day 3 | 7416.17 | 8997.58 | 7465.98 | 7959.91 | 898.99 | 11.29% | 88.44% |
| Day 5 | 7505.89 | 7789.58 | 7599.32 | 7631.60 | 144.57 | 1.89% | 84.80% |
| Day 7 | 5685.59 | 6813.6 | 5857.2 | 6118.80 | 607.80 | 9.93% | 67.99% |
| Day 14 | 4331.85 | 4542.49 | 4939.12 | 4604.49 | 308.35 | 6.70% | 51.16% |
| Day 21 | 4221.04 | 4897.48 | 4225.05 | 4447.86 | 389.39 | 8.75% | 49.42% |
| Day 31 | 3865.69 | 5027.86 | 4997.76 | 4630.44 | 662.46 | 14.31% | 51.45% |

POOL 4 Beta Amyloid 42 pg/mL 1200 pg/mL

| | Replicate 1 | Replicate 2 | Replicate 2 | MEAN | SD | % CV | % Recovery |
|---|---|---|---|---|---|---|---|
| Baseline | 1083.17 | 1007.45 | 1237.13 | 1109.25 | 117.04 | 10.55% | 92.44% |
| Day 1 | 1046.48 | 1215.49 | 1074.39 | 1112.12 | 90.60 | 8.15% | 92.68% |
| Day 3 | 1045.3 | 1119.79 | 1318.35 | 1161.15 | 141.14 | 12.16% | 96.76% |
| Day 5 | 1032.69 | 1172.59 | 1374.1 | 1193.13 | 171.63 | 14.38% | 99.43% |
| Day 7 | 968.59 | 1192.34 | 1327.84 | 1162.92 | 181.42 | 15.60% | 96.91% |
| Day 14 | 1102.62 | 1156.67 | 1243.97 | 1167.75 | 71.32 | 6.11% | 97.31% |
| Day 21 | 1380.18 | 1179.06 | 1165.8 | 1241.68 | 120.13 | 9.67% | 103.47% |
| Day 31 | 1341.91 | 1445.29 | 1491.16 | 1426.12 | 76.45 | 5.36% | 118.84% |

POOL 5 Beta Amyloid 42 pg/mL 6000 pg/mL

| | Replicate 1 | Replicate 2 | Replicate 2 | MEAN | SD | % CV | % Recovery |
|---|---|---|---|---|---|---|---|
| Baseline | 6677.96 | 6380.35 | 6933.19 | 6663.83 | 276.69 | 4.15% | 111.06% |
| Day 1 | 5571.06 | 6471.21 | 6952.26 | 6331.51 | 701.12 | 11.07% | 105.53% |
| Day 3 | 5474.18 | 6588.7 | 6046.94 | 6036.61 | 557.33 | 9.23% | 100.61% |
| Day 5 | 6496.2 | 6827.73 | 7163.7 | 6829.21 | 333.75 | 4.89% | 113.82% |

-continued

|        | Replicate 1 | Replicate 2 | Replicate 2 | MEAN    | SD      | % CV   | % Recovery |
|--------|-------------|-------------|-------------|---------|---------|--------|------------|
| Day 7  | 5616.75     | 6227.28     | 6454.22     | 6099.42 | 433.13  | 7.10%  | 101.66%    |
| Day 14 | 5145.26     | 6335.6      | 7603.78     | 6361.55 | 1229.47 | 19.33% | 106.03%    |
| Day 21 | 5272.62     | 5451.41     | 5770.77     | 5498.27 | 252.36  | 4.59%  | 91.64%     |
| Day 31 | 4507.56     | 5739.15     | 6495.96     | 5580.89 | 1003.60 | 17.98% | 93.01%     |

POOL 6 Beta Amyloid 42 20000 pg/mL

|          | Replicate 1 | Replicate 2 | Replicate 2 | MEAN     | SD      | % CV   | % Recovery |
|----------|-------------|-------------|-------------|----------|---------|--------|------------|
| Baseline | 21756.95    | 21339.04    | 20496.05    | 21197.35 | 642.28  | 3.03%  | 105.99%    |
| Day 1    | 18082.02    | 17251.16    | 19283.78    | 18205.65 | 1021.93 | 5.61%  | 91.03%     |
| Day 3    | 17597.95    | 16670.16    | 19199.17    | 17822.43 | 1279.36 | 7.18%  | 89.11%     |
| Day 5    | 19385.22    | 18263.81    | 15284.42    | 17644.48 | 2119.39 | 12.01% | 88.22%     |
| Day 7    | 14779.5     | 16218.56    | 16987.23    | 15995.10 | 1120.70 | 7.01%  | 79.98%     |
| Day 14   | 15267.66    | 15004.07    | 16492.44    | 15588.06 | 794.23  | 5.10%  | 77.94%     |
| Day 21   | 14152.8     | 16347.63    | 18450.29    | 16316.91 | 2148.91 | 13.17% | 81.58%     |
| Day 31   | 15242.65    | 15307.45    | 16358.04    | 15636.05 | 626.10  | 4.00%  | 78.18%     |

Room Temperature Stability (18.0 to 26.0° C.): Samples are stable up to 3 days at 18-26° C.

POOL 1 Beta Amyloid 40 600 pg/mL

|          | Replicate 1 | Replicate 2 | Replicate 2 | MEAN   | SD     | % CV   | % Recovery |
|----------|-------------|-------------|-------------|--------|--------|--------|------------|
| Baseline | 779.29      | 738.39      | 583.39      | 700.36 | 103.34 | 14.76% | 116.73%    |
| Day 1    | 597.97      | 555.18      | 651.41      | 601.52 | 48.21  | 8.02%  | 100.25%    |
| Day 3    | 677.29      | 639.59      | 627.46      | 648.11 | 25.99  | 4.01%  | 108.02%    |
| Day 5    | 483.68      | 489.69      | 435.26      | 469.54 | 29.84  | 6.36%  | 78.26%     |
| Day 7    | 20.19       | 7.97        | 22.45       | 16.87  | 7.79   | 46.18% | 2.81%      |
| Day 14   | 41.15       | 6.67        | 46.31       | 31.38  | 21.55  | 68.69% | 5.23%      |
| Day 21   | 4.64        | 28.6        | 36.02       | 23.09  | 16.40  | 71.04% | 3.85%      |
| Day 31   | 19.96       | 0.88        | 40.91       | 20.58  | 20.02  | 97.27% | 3.43%      |

POOL 2 Beta Amyloid 40 3000 pg/mL

|          | Replicate 1 | Replicate 2 | Replicate 2 | MEAN    | SD     | % CV   | % Recovery |
|----------|-------------|-------------|-------------|---------|--------|--------|------------|
| Baseline | 3073.58     | 1501.46     | 3340.37     | 2638.47 | 993.67 | 37.66% | 87.95%     |
| Day 1    | 2648.58     | 3019.2      | 2365.83     | 2677.87 | 327.67 | 12.24% | 89.26%     |
| Day 3    | 3170.96     | 3122.42     | 2934.33     | 3075.90 | 124.99 | 4.06%  | 102.53%    |
| Day 5    | 2780.11     | 2791.29     | 3224.36     | 2931.92 | 253.32 | 8.64%  | 97.73%     |
| Day 7    | 2623.02     | 2768.02     | 3080.48     | 2823.84 | 233.78 | 8.28%  | 94.13%     |
| Day 14   | 256.08      | 308.73      | 267.08      | 277.30  | 27.77  | 10.02% | 9.24%      |
| Day 21   | 14.05       | 25.17       | 22.32       | 20.51   | 5.78   | 28.16% | 0.68%      |
| Day 31   | 43.41       | 39.32       | 29.48       | 37.40   | 7.16   | 19.14% | 1.25%      |

POOL 3 Beta Amyloid 40 pg/mL 9000 pg/mL

|          | Replicate 1 | Replicate 2 | Replicate 2 | MEAN    | SD      | % CV   | % Recovery |
|----------|-------------|-------------|-------------|---------|---------|--------|------------|
| Baseline | 8599.60     | 9082.10     | 9287.20     | 8989.63 | 353.00  | 3.93%  | 99.88%     |
| Day 1    | 8064.65     | 10059.63    | 9271.61     | 9131.96 | 1004.79 | 11.00% | 101.47%    |
| Day 3    | 7135.90     | 7190.06     | 7525.27     | 7283.74 | 210.91  | 2.90%  | 80.93%     |
| Day 5    | 370.90      | 287.98      | 337.43      | 332.10  | 41.72   | 12.56% | 3.69%      |
| Day 7    | 2691.50     | 2768.60     | 2806.56     | 2755.55 | 58.63   | 2.13%  | 30.62%     |
| Day 14   | 346.01      | 367.40      | 466.41      | 393.27  | 64.23   | 16.33% | 4.37%      |
| Day 21   | 625.28      | 824.15      | 719.24      | 722.89  | 99.49   | 13.76% | 8.03%      |
| Day 31   | 1638.52     | 520.62      | 1844.42     | 1334.52 | 712.34  | 53.38% | 14.83%     |

POOL 4 Beta Amyloid 40 pg/mL 1200 pg/mL

|          | Replicate 1 | Replicate 2 | Replicate 2 | MEAN    | SD    | % CV    | % Recovery |
|----------|-------------|-------------|-------------|---------|-------|---------|------------|
| Baseline | 1147.09     | 1303.82     | 1184.02     | 1211.64 | 81.94 | 6.76%   | 100.97%    |
| Day 1    | 1195.71     | 1252.52     | 1293        | 1247.08 | 48.87 | 3.92%   | 103.92%    |
| Day 3    | 1133.27     | 1280.53     | 1194.55     | 1202.78 | 73.97 | 6.15%   | 100.23%    |
| Day 5    | 1148.79     | 1287.75     | 1100.57     | 1179.04 | 97.19 | 8.24%   | 98.25%     |
| Day 7    | 1069.39     | 968.4       | 1104.36     | 1047.38 | 70.60 | 6.74%   | 87.28%     |
| Day 14   | 0           | 120.26      | 0           | 40.09   | 69.43 | 173.21% | 3.34%      |
| Day 21   | 16.71       | 32.4        | 34.8        | 27.97   | 9.83  | 35.13%  | 2.33%      |
| Day 31   | 143.94      | −4.32       | 124.87      | 88.16   | 80.66 | 91.49%  | 7.35%      |

-continued

| POOL 5 Beta Amyloid 40 pg/mL 6000 pg/mL | | | | | | |
|---|---|---|---|---|---|---|
| | Replicate 1 | Replicate 2 | Replicate 2 | MEAN | SD | % CV | % Recovery |
| Baseline | 6542.39 | 6115.93 | 6015.49 | 6224.60 | 279.76 | 4.49% | 103.74% |
| Day 1 | 6245.93 | 6475.35 | 6066.35 | 6262.54 | 205.01 | 3.27% | 104.38% |
| Day 3 | 6639.61 | 6173.74 | 6044.22 | 6285.86 | 313.13 | 4.98% | 104.76% |
| Day 5 | 6285.39 | 6701.62 | 5615.48 | 6200.83 | 547.99 | 8.84% | 103.35% |
| Day 7 | 5047.34 | 4152.02 | 4746.15 | 4648.50 | 455.58 | 9.80% | 77.48% |
| Day 14 | 4196.56 | 4495.05 | 4094.12 | 4261.91 | 208.30 | 4.89% | 71.03% |
| Day 21 | 300.12 | 417.39 | 350.55 | 356.02 | 58.83 | 16.52% | 5.93% |
| Day 31 | 43.23 | 70.37 | 192.66 | 102.09 | 79.60 | 77.98% | 1.70% |

| POOL 6 Beta Amyloid 40 20000 pg/mL | | | | | | |
|---|---|---|---|---|---|---|
| | Replicate 1 | Replicate 2 | Replicate 2 | MEAN | SD | % CV | % Recovery |
| Baseline | 20310.45 | 20876.37 | 21447.84 | 20878.22 | 568.70 | 2.72% | 104.39% |
| Day 1 | 21141.19 | 22951.71 | 19538.39 | 21210.43 | 1707.71 | 8.05% | 106.05% |
| Day 3 | 19831.93 | 21044.04 | 20583.6 | 20486.52 | 611.86 | 2.99% | 102.43% |
| Day 5 | 19857.52 | 21786.11 | 19913.92 | 20519.18 | 1097.55 | 5.35% | 102.60% |
| Day 7 | 7033.67 | 7265.53 | 7245.05 | 7181.42 | 128.36 | 1.79% | 35.91% |
| Day 14 | 592.23 | 821.65 | 2138.35 | 1184.08 | 834.35 | 70.46% | 5.92% |
| Day 21 | 2417.51 | 2478.89 | 2553.32 | 2483.24 | 68.01 | 2.74% | 12.42% |
| Day 31 | 9604.6 | 10638.74 | 10448.29 | 10230.54 | 550.38 | 5.38% | 51.15% |

| POOL 1 Beta Amyloid 42 600 pg/mL | | | | | | |
|---|---|---|---|---|---|---|
| | Replicate 1 | Replicate 2 | Replicate 2 | MEAN | SD | % CV | % Recovery |
| Baseline | 715.19 | 711.63 | 597.55 | 674.79 | 66.92 | 9.92% | 112.47% |
| Day 1 | 707.17 | 691.20 | 635.20 | 677.86 | 37.79 | 5.58% | 112.98% |
| Day 3 | 713.79 | 601.45 | 724.24 | 679.83 | 68.08 | 10.01% | 113.30% |
| Day 5 | 623.04 | 722.61 | 535.83 | 627.16 | 93.46 | 14.90% | 104.53% |
| Day 7 | 86.65 | 67.82 | 98.02 | 84.16 | 15.25 | 18.12% | 14.03% |
| Day 14 | 148.17 | 147.30 | 198.27 | 164.58 | 29.18 | 17.73% | 27.43% |
| Day 21 | 1221.34 | 1287.15 | 1392.07 | 1300.19 | 86.11 | 6.62% | 216.70% |
| Day 31 | 21.71 | 100.48 | 82.78 | 68.32 | 41.33 | 60.49% | 11.39% |

| POOL 2 Beta Amyloid 42 3000 pg/mL | | | | | | |
|---|---|---|---|---|---|---|
| | Replicate 1 | Replicate 2 | Replicate 2 | MEAN | SD | % CV | % Recovery |
| Baseline | 2861.62 | 2890.83 | 3308.1 | 3020.18 | 249.77 | 8.27% | 100.67% |
| Day 1 | 2579.3 | 2366.57 | 3060.43 | 2668.77 | 355.48 | 13.32% | 88.96% |
| Day 3 | 3060.43 | 3106.46 | 3072.9 | 3079.93 | 23.81 | 0.77% | 102.66% |
| Day 5 | 2340.81 | 2751.9 | 2688.63 | 2593.78 | 221.35 | 8.53% | 86.46% |
| Day 7 | 2766.13 | 2542.61 | 2929.77 | 2746.17 | 194.35 | 7.08% | 91.54% |
| Day 14 | 505.01 | 593.27 | 685.43 | 594.57 | 90.22 | 15.17% | 19.82% |
| Day 21 | 321.55 | 375.87 | 334.76 | 344.06 | 28.33 | 8.23% | 11.47% |
| Day 31 | 172.5 | 205.61 | 308.62 | 228.91 | 70.99 | 31.01% | 7.63% |

| POOL 3 Beta Amyloid 42 pg/mL 9000 pg/mL | | | | | | |
|---|---|---|---|---|---|---|
| | Replicate 1 | Replicate 2 | Replicate 2 | MEAN | SD | % CV | % Recovery |
| Baseline | 7683.62 | 7786.05 | 7986.82 | 7818.83 | 154.24 | 1.97% | 86.88% |
| Day 1 | 7101.31 | 8620.92 | 7680.41 | 7800.88 | 766.93 | 9.83% | 86.68% |
| Day 3 | 6201.38 | 6152.6 | 7085.81 | 6479.93 | 525.27 | 8.11% | 72.00% |
| Day 5 | 1220.28 | 1539.99 | 1209.82 | 1323.36 | 187.68 | 14.18% | 14.70% |
| Day 7 | 2878.85 | 2559.36 | 2916.04 | 2784.75 | 196.08 | 7.04% | 30.94% |
| Day 14 | 1108.22 | 1249.35 | 988.14 | 1115.24 | 130.75 | 11.72% | 12.39% |
| Day 21 | 187.09 | 409.35 | 541.69 | 379.38 | 179.19 | 47.23% | 4.22% |
| Day 31 | 730.47 | 741.9 | 500.54 | 657.64 | 136.17 | 20.71% | 7.31% |

| POOL 4 Beta Amyloid 42 pg/mL 1200 pg/mL | | | | | | |
|---|---|---|---|---|---|---|
| | Replicate 1 | Replicate 2 | Replicate 2 | MEAN | SD | % CV | % Recovery |
| Baseline | 1334.21 | 1203.74 | 1451.67 | 1329.87 | 124.02 | 9.33% | 110.82% |
| Day 1 | 1022.2 | 1328.08 | 1184.74 | 1178.34 | 153.04 | 12.99% | 98.20% |
| Day 3 | 1186.53 | 1093.62 | 1293.39 | 1191.18 | 99.97 | 8.39% | 99.27% |
| Day 5 | 1021.25 | 1468.26 | 1030.04 | 1173.18 | 255.58 | 21.79% | 97.77% |
| Day 7 | 1046.77 | 1055.15 | 1071.49 | 1057.80 | 12.57 | 1.19% | 88.15% |

-continued

| | | | | | | | |
|---|---|---|---|---|---|---|---|
| Day 14 | 831.31 | 579.26 | 1369.95 | 926.84 | 403.91 | 43.58% | 77.24% |
| Day 21 | 152.52 | 397.68 | 233.18 | 261.13 | 124.95 | 47.85% | 21.76% |
| Day 31 | 760.66 | 151.54 | 258.9 | 390.37 | 325.15 | 83.29% | 32.53% |

| POOL 5 Beta Amyloid 42 pg/mL 6000 pg/mL | | | | | | | |
|---|---|---|---|---|---|---|---|
| | Replicate 1 | Replicate 2 | Replicate 2 | MEAN | SD | % CV | % Recovery |
| Baseline | 6821.3 | 6333.16 | 6095.21 | 6416.56 | 370.16 | 5.77% | 106.94% |
| Day 1 | 5607.25 | 7000.01 | 6326.05 | 6311.10 | 696.50 | 11.04% | 105.19% |
| Day 3 | 6966.14 | 5878.18 | 6083.74 | 6309.35 | 578.01 | 9.16% | 105.16% |
| Day 5 | 5571.6 | 6456.15 | 5511.17 | 5846.31 | 529.00 | 9.05% | 97.44% |
| Day 7 | 5713.91 | 4808.07 | 5766.28 | 5429.42 | 538.74 | 9.92% | 90.49% |
| Day 14 | 4462.05 | 4518.25 | 3740.19 | 4240.16 | 433.90 | 10.23% | 70.67% |
| Day 21 | 437.82 | 401.52 | 542.97 | 460.77 | 73.46 | 15.94% | 7.68% |
| Day 31 | 600.29 | 617.72 | 865.64 | 694.55 | 148.42 | 21.37% | 11.58% |

| POOL 6 Beta Amyloid 42 20000 pg/mL | | | | | | | |
|---|---|---|---|---|---|---|---|
| | Replicate 1 | Replicate 2 | Replicate 2 | MEAN | SD | % CV | % Recovery |
| Baseline | 21756.95 | 21339.04 | 20496.05 | 21197.35 | 642.28 | 3.03% | 105.99% |
| Day 1 | 22016.05 | 21569.11 | 19770.44 | 21118.53 | 1188.68 | 5.63% | 105.59% |
| Day 3 | 21983.38 | 23840.4 | 21233.98 | 22352.59 | 1341.86 | 6.00% | 111.76% |
| Day 5 | 20061.84 | 19555.29 | 20219.32 | 19945.48 | 346.97 | 1.74% | 99.73% |
| Day 7 | 8155.77 | 9523.15 | 9885.37 | 9188.10 | 912.18 | 9.93% | 45.94% |
| Day 14 | 3224.1 | 4504.06 | 6381.28 | 4703.15 | 1587.98 | 33.76% | 23.52% |
| Day 21 | 2571.06 | 2533.15 | 3191.43 | 2765.21 | 369.60 | 13.37% | 13.83% |
| Day 31 | 4629.03 | 4807.18 | 3974.24 | 4470.15 | 438.61 | 9.81% | 22.35% |

Frozen Stability (−10.0 to −30.0° C.): Samples are stable up to 31 days at −10 to −30° C.

| POOL 1 Beta Amyloid 40 600 pg/mL | | | | | | | |
|---|---|---|---|---|---|---|---|
| | Replicate 1 | Replicate 2 | Replicate 2 | MEAN | SD | % CV | % Recovery |
| Baseline | 646.34 | 630.12 | 623.37 | 633.28 | 11.81 | 1.86% | 105.55% |
| Day 1 | 553.74 | 649.95 | 737.08 | 646.92 | 91.71 | 14.18% | 107.82% |
| Day 3 | 679.57 | 717.08 | 645.37 | 680.67 | 35.87 | 5.27% | 113.45% |
| Day 5 | 572.02 | 681.43 | 629.8 | 627.75 | 54.73 | 8.72% | 104.63% |
| Day 7 | 543.13 | 642.62 | 649.39 | 611.71 | 59.49 | 9.73% | 101.95% |
| Day 14 | 596.61 | 636.47 | 561.51 | 598.20 | 37.51 | 6.27% | 99.70% |
| Day 21 | 612.82 | 585.02 | 586.71 | 594.85 | 15.59 | 2.62% | 99.14% |
| Day 31 | 586.31 | 596.06 | 677.97 | 620.11 | 50.34 | 8.12% | 103.35% |

| POOL 2 Beta Amyloid 40 3000 pg/mL | | | | | | | |
|---|---|---|---|---|---|---|---|
| | Replicate 1 | Replicate 2 | Replicate 2 | MEAN | SD | % CV | % Recovery |
| Baseline | 3095.88 | 2786.21 | 2749.96 | 2877.35 | 190.12 | 6.61% | 95.91% |
| Day 1 | 3212.21 | 3465.63 | 3022.97 | 3233.60 | 222.10 | 6.87% | 107.79% |
| Day 3 | 2895.18 | 2980.17 | 2984.49 | 2953.28 | 50.36 | 1.71% | 98.44% |
| Day 5 | 2825.26 | 3536.06 | 3441.65 | 3267.66 | 386.02 | 11.81% | 108.92% |
| Day 7 | 3166.74 | 2846.27 | 2954.38 | 2989.13 | 163.04 | 5.45% | 99.64% |
| Day 14 | 2511.23 | 2775.96 | 3020.4 | 2769.20 | 254.65 | 9.20% | 92.31% |
| Day 21 | 2511.23 | 2775.96 | 3020.4 | 2769.20 | 254.65 | 9.20% | 92.31% |
| Day 31 | 2893.27 | 3086.6 | 2854.03 | 2944.63 | 124.50 | 4.23% | 98.15% |

| POOL 3 Beta Amyloid 40 9000 pg/mL | | | | | | | |
|---|---|---|---|---|---|---|---|
| | Replicate 1 | Replicate 2 | Replicate 2 | MEAN | SD | % CV | % Recovery |
| Baseline | 9041.95 | 8204.27 | 9240.21 | 8828.81 | 549.88 | 6.23% | 98.10% |
| Day 1 | 8783.7 | 10827.22 | 8982.54 | 9531.15 | 1126.82 | 11.82% | 105.90% |
| Day 3 | 9211.93 | 9149.86 | 8867.29 | 9076.36 | 183.70 | 2.02% | 100.85% |
| Day 5 | 9182.12 | 9997.19 | 9886.45 | 9688.59 | 442.09 | 4.56% | 107.65% |
| Day 7 | 8569.08 | 8999.58 | 9511.47 | 9026.71 | 471.78 | 5.23% | 100.30% |
| Day 14 | 9220.4 | 9028.98 | 8064.85 | 8771.41 | 619.34 | 7.06% | 97.46% |
| Day 21 | 8424.04 | 9700.88 | 9775.48 | 9300.13 | 759.64 | 8.17% | 103.33% |
| Day 31 | 8912.04 | 7891.96 | 8515.74 | 8439.91 | 514.25 | 6.09% | 93.78% |

| POOL 4 Beta Amyloid 40 6000 pg/mL | | | | | | |
|---|---|---|---|---|---|---|
| | Replicate 1 | Replicate 2 | Replicate 2 | MEAN | SD | % CV | % Recovery |
| Baseline | 6453.76 | 5952.82 | 5980.68 | 6129.09 | 281.52 | 4.59% | 102.15% |
| Day 1 | 6614.06 | 6027.79 | 6375.06 | 6338.97 | 294.80 | 4.65% | 105.65% |
| Day 3 | 5756.91 | 6360.45 | 6702.4 | 6273.25 | 478.74 | 7.63% | 104.55% |
| Day 5 | 5726.32 | 5715.8 | 7001.74 | 6147.95 | 739.42 | 12.03% | 102.47% |
| Day 7 | 5126.17 | 6209.65 | 6422.83 | 5919.55 | 695.31 | 11.75% | 98.66% |
| Day 14 | 5598.62 | 5514.06 | 5780.43 | 5631.04 | 136.11 | 2.42% | 93.85% |
| Day 21 | 5780.43 | 7030.06 | 6223.43 | 6344.64 | 633.57 | 9.99% | 105.74% |
| Day 31 | 6861.57 | 6840.4 | 6010.14 | 6570.70 | 485.58 | 7.39% | 109.51% |

| POOL 5 Beta Amyloid 40 1200 pg/mL | | | | | | |
|---|---|---|---|---|---|---|
| | Replicate 1 | Replicate 2 | Replicate 2 | MEAN | SD | % CV | % Recovery |
| Baseline | 1310.92 | 1162.27 | 1209.75 | 1227.65 | 75.92 | 6.18% | 102.30% |
| Day 1 | 1241.58 | 1149.45 | 1391.02 | 1260.68 | 121.91 | 9.67% | 105.06% |
| Day 3 | 1076.87 | 1083.95 | 1027.59 | 1062.80 | 30.70 | 2.89% | 88.57% |
| Day 5 | 1132.64 | 1284.34 | 1234.74 | 1217.24 | 77.35 | 6.35% | 101.44% |
| Day 7 | 1291.93 | 1451.69 | 1315.11 | 1352.91 | 86.33 | 6.38% | 112.74% |
| Day 14 | 1172.05 | 1203.56 | 1232.12 | 1202.58 | 30.05 | 2.50% | 100.21% |
| Day 21 | 1241.21 | 1110.38 | 1168.52 | 1173.37 | 65.55 | 5.59% | 97.78% |
| Day 31 | 1083.95 | 1027.59 | 1156.08 | 1089.21 | 64.41 | 5.91% | 90.77% |

| POOL 1 Beta Amyloid 42 600 pg/mL | | | | | | |
|---|---|---|---|---|---|---|
| | Replicate 1 | Replicate 2 | Replicate 2 | MEAN | SD | % CV | % Recovery |
| Baseline | 551.44 | 624.68 | 669.50 | 615.21 | 59.60 | 9.69% | 102.53% |
| Day 1 | 564.89 | 622.57 | 633.74 | 607.07 | 36.95 | 6.09% | 101.18% |
| Day 3 | 525.73 | 459.44 | 576.28 | 520.48 | 58.60 | 11.26% | 86.75% |
| Day 5 | 648.20 | 753.93 | 567.60 | 656.58 | 93.45 | 14.23% | 109.43% |
| Day 7 | 509.36 | 559.91 | 615.35 | 561.54 | 53.01 | 9.44% | 93.59% |
| Day 14 | 466.70 | 632.30 | 618.20 | 572.40 | 91.81 | 16.04% | 95.40% |
| Day 21 | 574.67 | 447.54 | 556.89 | 526.37 | 68.84 | 13.08% | 87.73% |
| Day 31 | 466.33 | 493.23 | 583.68 | 514.41 | 61.48 | 11.95% | 85.74% |

| POOL 2 Beta Amyloid 42 3000 pg/mL | | | | | | |
|---|---|---|---|---|---|---|
| | Replicate 1 | Replicate 2 | Replicate 2 | MEAN | SD | % CV | % Recovery |
| Baseline | 2948.02 | 2894.12 | 3253.65 | 3031.93 | 193.90 | 6.40% | 101.06% |
| Day 1 | 3329.08 | 2842.89 | 3721.36 | 3297.78 | 440.07 | 13.34% | 109.93% |
| Day 3 | 3070.81 | 3338.41 | 3281.97 | 3230.40 | 141.06 | 4.37% | 107.68% |
| Day 5 | 3162.79 | 3783.34 | 3701.06 | 3549.06 | 337.04 | 9.50% | 118.30% |
| Day 7 | 3009.29 | 2966.92 | 3399.7 | 3125.30 | 238.58 | 7.63% | 104.18% |
| Day 14 | 2648.36 | 2957.23 | 3382 | 2995.86 | 368.34 | 12.30% | 99.86% |
| Day 21 | 2648.36 | 2957.23 | 3382 | 2995.86 | 368.34 | 12.30% | 99.86% |
| Day 31 | 3695.08 | 3249.83 | 3065.84 | 3336.92 | 323.53 | 9.70% | 111.23% |

| POOL 3 Beta Amyloid 42 9000 pg/mL | | | | | | |
|---|---|---|---|---|---|---|
| | Replicate 1 | Replicate 2 | Replicate 2 | MEAN | SD | % CV | % Recovery |
| Baseline | 9131.88 | 8396.59 | 8877.05 | 8801.84 | 373.37 | 4.24% | 97.80% |
| Day 1 | 10014.67 | 11304.49 | 9468.86 | 10262.67 | 942.61 | 9.18% | 114.03% |
| Day 3 | 8053.3 | 9772.46 | 9749.97 | 9191.91 | 986.13 | 10.73% | 102.13% |
| Day 5 | 8475.88 | 10403.45 | 10578.46 | 9819.26 | 1166.69 | 11.88% | 109.10% |
| Day 7 | 8441.49 | 9248.89 | 10118.42 | 9269.60 | 838.66 | 9.05% | 103.00% |
| Day 14 | 9507.55 | 9268.16 | 8255.54 | 9010.42 | 664.61 | 7.38% | 100.12% |
| Day 21 | 9372.95 | 10354.65 | 9516.11 | 9747.90 | 530.31 | 5.44% | 108.31% |
| Day 31 | 9454.97 | 9227.46 | 8902.68 | 9195.04 | 277.57 | 3.02% | 102.17% |

| POOL 4 Beta Amyloid 42 6000 pg/mL | | | | | | |
|---|---|---|---|---|---|---|
| | Replicate 1 | Replicate 2 | Replicate 2 | MEAN | SD | % CV | % Recovery |
| Baseline | 6677.96 | 6380.35 | 6933.19 | 6663.83 | 276.69 | 4.15% | 111.06% |
| Day 1 | 5985.48 | 5498.94 | 6791.57 | 6092.00 | 652.86 | 10.72% | 101.53% |
| Day 3 | 5446.16 | 6668.14 | 7105.19 | 6406.50 | 859.91 | 13.42% | 106.77% |
| Day 5 | 5870.58 | 5233.08 | 6853.32 | 5985.66 | 816.23 | 13.64% | 99.76% |
| Day 7 | 5703.01 | 5989.02 | 6362.57 | 6018.20 | 330.75 | 5.50% | 100.30% |

-continued

| | | | | | | | |
|---|---|---|---|---|---|---|---|
| Day 14 | 5834.97 | 6306.89 | 5534.01 | 5891.96 | 389.58 | 6.61% | 98.20% |
| Day 21 | 5534.01 | 7308.97 | 6528.39 | 6457.12 | 889.62 | 13.78% | 107.62% |
| Day 31 | 6305.84 | 7144.75 | 5356.93 | 6269.17 | 894.47 | 14.27% | 104.49% |

POOL 5 Beta Amyloid 42 1200 pg/mL

| | Replicate 1 | Replicate 2 | Replicate 2 | MEAN | SD | % CV | % Recovery |
|---|---|---|---|---|---|---|---|
| Baseline | 1083.17 | 1007.45 | 1237.13 | 1109.25 | 117.04 | 10.55% | 92.44% |
| Day 1 | 1322.22 | 1270.31 | 1082.88 | 1225.14 | 125.90 | 10.28% | 102.09% |
| Day 3 | 1024.85 | 949.35 | 907.3 | 960.50 | 59.56 | 6.20% | 80.04% |
| Day 5 | 1249.41 | 971.58 | 1231.45 | 1150.81 | 155.48 | 13.51% | 95.90% |
| Day 7 | 1053.04 | 1275.89 | 1263.91 | 1197.61 | 125.35 | 10.47% | 99.80% |
| Day 14 | 949.01 | 1167.07 | 1117.96 | 1078.01 | 114.39 | 10.61% | 89.83% |
| Day 21 | 1276.91 | 1348.99 | 1005.55 | 1210.48 | 181.10 | 14.96% | 100.87% |
| Day 31 | 1025.13 | 983.58 | 1238.35 | 1082.35 | 136.69 | 12.63% | 90.20% |

Example 10: Interference Study

Acceptability criteria: The difference due to a potential interfering substance should be ≤2SD or 20% CV to be considered acceptable.

Hemolysis Interference: Six spike pools were analyzed in triplicate for a baseline, slight, moderate and gross hemolysis interference.

Beta Amyloid 40 and Beta Amyloid 42 is only acceptable for non-hemolyzed and slightly hemolyzed cerebrospinal fluid samples.

| Hemolysis | Baseline | Beta Pool 1 Slight | Amyloid 40 Moderate | 2000 Gross | pg/mL Total |
|---|---|---|---|---|---|
| Replicate 1 | 1844.27 | 2218.98 | 1972.21 | 2509.92 | 2136.35 |
| Replicate 2 | 1676.71 | 2156.41 | 2121.93 | 2030.17 | 1996.31 |
| Replicate 3 | 1682.64 | 1930.54 | 1873.38 | 2301.92 | 1947.12 |
| MEAN | 1734.54 | 2101.98 | 1989.17 | 2280.67 | 2026.59 |
| STDEV | 95.08 | 151.73 | 125.14 | 240.58 | 153.13 |
| % CV | 5.48% | 7.22% | 6.29% | 10.55% | 7.38% |
| % Recovery | 86.73% | 105.10% | 99.46% | 114.03% | 101.33% |

| Hemolysis | Baseline | Beta Pool 1 Slight | Amyloid 42 Moderate | 2000 Gross | pg/mL Total |
|---|---|---|---|---|---|
| Replicate 1 | 1710.73 | 2213.31 | 2587.34 | 2803 | 2328.60 |
| Replicate 2 | 1608.45 | 1983.62 | 2322.18 | 2327.79 | 2060.51 |
| Replicate 3 | 1652.88 | 2092.85 | 1827.26 | 3203.29 | 2194.10 |
| MEAN | 1657.35 | 2096.63 | 2245.59 | 2778.03 | 2194.40 |
| STDEV | 51.29 | 114.89 | 385.78 | 438.28 | 247.56 |
| % CV | 3.09% | 5.48% | 17.18% | 15.78% | 10.38% |
| % Recovery | 82.87% | 104.83% | 112.28% | 138.90% | 109.72% |

| Hemolysis | Baseline | Beta Pool 3 Slight | Amyloid 40 Moderate | 6000 Gross | pg/mL Total |
|---|---|---|---|---|---|
| Replicate 1 | 5243.65 | 5724.38 | 5902.54 | 5860.26 | 5682.71 |
| Replicate 2 | 5677.02 | 5569.79 | 5947.92 | 5902.54 | 5774.32 |
| Replicate 3 | 6116.8 | 5952.4 | 6660.26 | 5677.02 | 6101.62 |
| MEAN | 5679.16 | 5748.86 | 6170.24 | 5813.27 | 5852.88 |
| STDEV | 436.58 | 192.48 | 424.98 | 119.88 | 293.48 |
| % CV | 7.69% | 3.35% | 6.89% | 2.06% | 5.00% |
| % Recovery | 94.65% | 95.81% | 102.84% | 96.89% | 97.55% |

| Hemolysis | Baseline | Beta Pool 3 Slight | Amyloid 42 Moderate | 6000 Gross | pg/mL Total |
|---|---|---|---|---|---|
| Replicate 1 | 4683.16 | 6010.68 | 7298 | 7298 | 6322.46 |
| Replicate 2 | 5857.22 | 6187.23 | 7357.24 | 5857.22 | 6314.73 |
| Replicate 3 | 6274.4 | 6725.44 | 5665.83 | 7858.76 | 6631.11 |
| MEAN | 5604.93 | 6307.78 | 6773.69 | 7004.66 | 6422.77 |
| STDEV | 825.08 | 372.32 | 959.89 | 1032.51 | 797.45 |
| % CV | 14.72% | 5.90% | 14.17% | 14.74% | 12.38% |
| % Recovery | 93.42% | 105.13% | 112.89% | 116.74% | 107.05% |

| Hemolysis | Baseline | Beta Pool 5 Slight | Amyloid 40 Moderate | 14000 Gross | pg/mL Total |
|---|---|---|---|---|---|
| Replicate 1 | 16318.69 | 16205.4 | 15909.32 | 17106.17 | 16384.90 |
| Replicate 2 | 15739.55 | 16847.72 | 16061.5 | 15891.29 | 16135.02 |
| Replicate 3 | 17159.51 | 16499.24 | 18690.45 | 15563.36 | 16978.14 |
| MEAN | 16405.92 | 16517.45 | 16887.09 | 16186.94 | 16499.35 |
| STDEV | 713.99 | 321.55 | 1563.61 | 812.79 | 852.98 |
| % CV | 4.35% | 1.95% | 9.26% | 5.02% | 5.14% |
| % Recovery | 117.19% | 117.98% | 120.62% | 115.62% | 117.85% |

| Hemolysis | Baseline | Beta Pool 5 Slight | Amyloid 42 Moderate | 14000 Gross | pg/mL Total |
|---|---|---|---|---|---|
| Replicate 1 | 16275.91 | 14772.68 | 17788.89 | 15214.59 | 16013.02 |
| Replicate 2 | 16777.1 | 13701.79 | 16693.63 | 17433.68 | 16151.55 |
| Replicate 3 | 15508.59 | 16548.81 | 16234.96 | 15868.04 | 16040.10 |
| MEAN | 16187.20 | 15007.76 | 16905.83 | 16172.10 | 16068.22 |
| STDEV | 638.89 | 1437.99 | 798.40 | 1140.36 | 1003.91 |
| % CV | 3.95% | 9.58% | 4.72% | 7.05% | 6.33% |
| % Recovery | 115.62% | 107.20% | 120.76% | 115.52% | 114.77% |

| Hemolysis | Baseline | Beta Pool 2 Slight | Amyloid 40 Moderate | 4000 Gross | pg/mL Total |
|---|---|---|---|---|---|
| Replicate 1 | 3762.71 | 3785.66 | 4510.79 | 4256.2 | 4078.84 |
| Replicate 2 | 4562.35 | 4864.24 | 4423.28 | 4808.1 | 4664.49 |
| Replicate 3 | 4679.51 | 4659.03 | 5073.88 | 3987.41 | 4599.96 |
| MEAN | 4334.86 | 4436.31 | 4669.32 | 4350.57 | 4447.76 |
| STDEV | 498.94 | 572.75 | 353.08 | 418.40 | 460.79 |
| % CV | 11.51% | 12.91% | 7.56% | 9.62% | 10.40% |
| % Recovery | 108.37% | 110.91% | 116.73% | 108.76% | 111.19% |

| | Baseline | Beta Pool 2 Slight | Amyloid 42 Moderate | 4000 Gross | pg/mL Total |
|---|---|---|---|---|---|
| Replicate 1 | 3589.03 | 3620.91 | 5005.48 | 4908.61 | 4281.01 |
| Replicate 2 | 4496.67 | 5052.12 | 5638.52 | 5571.62 | 5189.73 |
| Replicate 3 | 4112.79 | 4726.31 | 5032.28 | 5086.1 | 4739.37 |
| MEAN | 4066.16 | 4466.45 | 5225.43 | 5188.78 | 4736.70 |

|  | | | | | |
|---|---|---|---|---|---|
| STDEV | 455.61 | 750.16 | 358.00 | 343.22 | 476.75 |
| % CV | 11.20% | 16.80% | 6.85% | 6.61% | 10.37% |
| % Recovery | 101.65% | 111.66% | 130.64% | 129.72% | 118.42% |

| Hemolysis | Baseline | Beta Pool Slight | Amyloid 40 4 Moderate | 12000 Gross | pg/mL Total |
|---|---|---|---|---|---|
| Replicate 1 | 13548.97 | 11514.4 | 10243.99 | 12982.46 | 12072.46 |
| Replicate 2 | 10931.85 | 11070.63 | 12083.48 | 12024.58 | 11527.64 |
| Replicate 3 | 12232.13 | 11732.88 | 10797.77 | 11122.15 | 11471.23 |
| MEAN | 12237.65 | 11439.30 | 11041.75 | 12043.06 | 11690.44 |
| STDEV | 1308.57 | 337.45 | 943.70 | 930.29 | 880.00 |
| % CV | 10.69% | 2.95% | 8.55% | 7.72% | 7.48% |
| % Recovery | 101.98% | 95.33% | 92.01% | 100.36% | 97.42% |

| Hemolysis | Baseline | Beta Pool Slight | Amyloid 42 4 Moderate | 12000 Gross | pg/mL Total |
|---|---|---|---|---|---|
| Replicate 1 | 12895.5 | 10962.68 | 11010.98 | 12132.09 | 11750.31 |
| Replicate 2 | 13332.29 | 10058.52 | 12917.13 | 11115.89 | 11855.96 |
| Replicate 3 | 13337.19 | 13511.14 | 9223.21 | 13398.17 | 12367.43 |
| MEAN | 13188.33 | 11510.78 | 11050.44 | 12215.38 | 11991.23 |
| STDEV | 253.61 | 1790.38 | 1847.28 | 1143.42 | 1258.67 |
| % CV | 1.92% | 15.55% | 16.72% | 9.36% | 10.89% |
| % Recovery | 109.90% | 95.92% | 92.09% | 101.79% | 99.93% |

| Hemolysis | Baseline | Beta Pool Slight | Amyloid 40 6 Moderate | 16000 Gross | pg/mL Total |
|---|---|---|---|---|---|
| Replicate 1 | 16850.04 | 22436.41 | 19389.69 | 18606.33 | 19320.62 |
| Replicate 2 | 18143.58 | 20584.49 | 19475.64 | 18724.26 | 19231.99 |
| Replicate 3 | 18419.48 | 21353.42 | 19913.02 | 18236.68 | 19480.65 |
| MEAN | 17804.37 | 21458.11 | 19592.78 | 18522.42 | 19344.42 |
| STDEV | 837.90 | 930.39 | 280.64 | 254.39 | 575.83 |
| % CV | 4.71% | 4.34% | 1.43% | 1.37% | 2.96% |
| % Recovery | 111.28% | 134.11% | 122.45% | 115.77% | 120.90% |

| Hemolysis | Baseline | Beta Pool Slight | Amyloid 42 6 Moderate | 16000 Gross | pg/mL Total |
|---|---|---|---|---|---|
| Replicate 1 | 15090.2 | 17802.59 | 23536.65 | 16841.59 | 18317.76 |
| Replicate 2 | 16245.91 | 17194.89 | 19780.66 | 17529.35 | 17687.70 |
| Replicate 3 | 17331.23 | 16649.26 | 22671.94 | 17116.46 | 18442.22 |
| MEAN | 16222.45 | 17215.58 | 21996.42 | 17162.47 | 18149.23 |
| STDEV | 1120.70 | 576.94 | 1967.01 | 346.18 | 1002.71 |
| % CV | 6.91% | 3.35% | 8.94% | 2.02% | 5.30% |
| % Recovery | 101.39% | 107.60% | 137.48% | 107.27% | 113.43% |

Lipemia Interference: Six spike pools were analyzed in triplicate for a baseline, slight, moderate and gross lipemic interference.

Beta Amyloid 40 and Beta Amyloid 42 is acceptable for slightly and moderately lipemic cerebrospinal fluid samples.

| Lipemic | Baseline | Beta Pool Slight | Amyloid 40 1 Moderate | 2000 Gross | pg/mL Total |
|---|---|---|---|---|---|
| Replicate 1 | 2122.57 | 1867.23 | 1749.50 | 2130.24 | 1967.39 |
| Replicate 2 | 1840.46 | 1975.60 | 1860.85 | 2158.83 | 1958.94 |
| Replicate 3 | 1842.49 | 2105.69 | 1665.35 | 1960.04 | 1893.39 |
| MEAN | 1935.17 | 1982.84 | 1758.57 | 2083.04 | 1939.90 |
| STDEV | 162.29 | 119.39 | 98.06 | 107.47 | 121.81 |
| % CV | 8.39% | 6.02% | 5.58% | 5.16% | 6.29% |
| % Recovery | 96.76% | 99.14% | 87.93% | 104.15% | 97.00% |

| Lipemic | Baseline | Beta Pool Slight | Amyloid 40 2 Moderate | 4000 Gross | pg/mL Total |
|---|---|---|---|---|---|
| Replicate 1 | 3686.74 | 3982.2 | 3818.81 | 3567.06 | 3763.70 |
| Replicate 2 | 4309.05 | 4176.51 | 3668.16 | 3896.53 | 4012.56 |
| Replicate 3 | 3483.79 | 4223.27 | 3672.9 | 4053.58 | 3858.39 |
| MEAN | 3826.53 | 4127.33 | 3719.96 | 3839.06 | 3878.22 |
| STDEV | 430.02 | 127.84 | 85.64 | 248.30 | 222.95 |
| % CV | 11.24% | 3.10% | 2.30% | 6.47% | 5.78% |
| % Recovery | 95.66% | 103.18% | 93.00% | 95.98% | 96.96% |

| Lipemic | Baseline | Beta Pool Slight | Amyloid 40 3 Moderate | 6000 Gross | pg/mL Total |
|---|---|---|---|---|---|
| Replicate 1 | 6048.48 | 6028.48 | 5897.49 | 4912.21 | 5721.67 |
| Replicate 2 | 5483.52 | 6205.15 | 6136.62 | 5144.54 | 5742.46 |
| Replicate 3 | 5405.7 | 5779.68 | 5634.34 | 5051.26 | 5467.75 |
| MEAN | 5645.90 | 6004.44 | 5889.48 | 5036.00 | 5643.96 |
| STDEV | 350.81 | 213.75 | 251.24 | 116.91 | 233.18 |
| % CV | 6.21% | 3.56% | 4.27% | 2.32% | 4.09% |
| % Recovery | 94.10% | 100.07% | 98.16% | 83.93% | 94.07% |

| Lipemic | Baseline | Beta Pool Slight | Amyloid 40 4 Moderate | 12000 Gross | pg/mL Total |
|---|---|---|---|---|---|
| Replicate 1 | 11795.73 | 12524.54 | 10057.38 | 10551.66 | 11232.33 |
| Replicate 2 | 11815.14 | 11947.41 | 11263.66 | 11027.67 | 11513.47 |
| Replicate 3 | 12548.85 | 11322.75 | 10836.52 | 10965.53 | 11418.41 |
| MEAN | 12053.24 | 11931.57 | 10719.19 | 10848.29 | 11388.07 |
| STDEV | 429.32 | 601.05 | 611.64 | 258.76 | 475.19 |
| % CV | 3.56% | 5.04% | 5.71% | 2.39% | 4.17% |
| % Recovery | 100.44% | 99.43% | 89.33% | 90.40% | 94.90% |

| Lipemic | Baseline | Beta Pool Slight | Amyloid 40 5 Moderate | 14000 Gross | pg/mL Total |
|---|---|---|---|---|---|
| Replicate 1 | 13705.99 | 15174.54 | 15620.23 | 15814.3 | 15078.77 |
| Replicate 2 | 14636.59 | 16544.85 | 14053.01 | 14138.08 | 14843.13 |
| Replicate 3 | 13981.06 | 14130.05 | 15965.99 | 14285.88 | 14590.75 |
| MEAN | 14107.88 | 15283.15 | 15213.08 | 14746.09 | 14837.55 |
| STDEV | 478.09 | 1211.06 | 1019.41 | 928.05 | 909.15 |
| % CV | 3.39% | 7.92% | 6.70% | 6.29% | 6.08% |
| % Recovery | 100.77% | 109.17% | 108.66% | 105.33% | 105.98% |

| Lipemic | Baseline | Beta Pool Slight | Amyloid 40 6 Moderate | 16000 Gross | pg/mL Total |
|---|---|---|---|---|---|
| Replicate 1 | 13138.69 | 15864.69 | 16090.04 | 15407.11 | 15125.13 |
| Replicate 2 | 15532.57 | 14726.33 | 15822.47 | 15995.82 | 15519.30 |
| Replicate 3 | 14445.5 | 15980.5 | 15573.06 | 16628.44 | 15656.88 |
| MEAN | 14372.25 | 15523.84 | 15828.52 | 16010.46 | 15433.77 |
| STDEV | 1198.62 | 693.09 | 258.54 | 610.80 | 690.26 |
| % CV | 8.34% | 4.46% | 1.63% | 3.81% | 4.56% |
| % Recovery | 89.83% | 97.02% | 98.93% | 100.07% | 96.46% |

| Lipemic | Baseline | Beta Pool Slight | Amyloid 42 1 Moderate | 2000 Gross | pg/mL Total |
|---|---|---|---|---|---|
| Replicate 1 | 1770.53 | 2216.73 | 1645.46 | 2049.87 | 1920.65 |
| Replicate 2 | 1910.30 | 1882.26 | 1523.80 | 1956.37 | 1818.18 |
| Replicate 3 | 1702.76 | 1946.21 | 1753.75 | 1931.18 | 1833.48 |
| MEAN | 1794.53 | 2015.07 | 1641.00 | 1979.14 | 1857.44 |
| STDEV | 105.83 | 177.55 | 115.04 | 62.54 | 115.24 |
| % CV | 5.90% | 8.81% | 7.01% | 3.16% | 6.22% |
| % Recovery | 89.73% | 100.75% | 82.05% | 98.96% | 92.87% |

| Lipemic | Baseline | Beta Pool Slight | Amyloid 42 2 Moderate | 4000 Gross | pg/mL Total |
|---|---|---|---|---|---|
| Replicate 1 | 3478.11 | 3586.59 | 4288.67 | 3411.32 | 3691.17 |
| Replicate 2 | 4226.72 | 3458.62 | 3391.05 | 3641 | 3679.35 |
| Replicate 3 | 3573.75 | 3530.16 | 3387.5 | 3892.18 | 3595.90 |
| MEAN | 3759.53 | 3525.12 | 3689.07 | 3648.17 | 3655.47 |
| STDEV | 407.42 | 64.13 | 519.27 | 240.51 | 307.83 |
| % CV | 10.84% | 1.82% | 14.08% | 6.59% | 8.33% |
| % Recovery | 93.99% | 88.13% | 92.23% | 91.20% | 91.39% |

| Lipemic | Baseline | Beta Pool Slight | Amyloid 42 3 Moderate | 6000 Gross | pg/mL Total |
|---|---|---|---|---|---|
| Replicate 1 | 5663.22 | 4897.39 | 6049.81 | 4046.59 | 5164.25 |
| Replicate 2 | 4662.02 | 5540.19 | 5727.69 | 4578.2 | 5127.03 |
| Replicate 3 | 4620.36 | 5042 | 4901.74 | 4681.98 | 4811.52 |
| MEAN | 4981.87 | 5159.86 | 5559.75 | 4435.59 | 5034.27 |
| STDEV | 590.44 | 337.22 | 592.17 | 340.86 | 465.17 |
| % CV | 11.85% | 6.54% | 10.65% | 7.68% | 9.18% |
| % Recovery | 83.03% | 86.00% | 92.66% | 73.93% | 83.90% |

| Lipemic | Baseline | Beta Pool Slight | Amyloid 42 4 Moderate | Gross | pg/mL Total |
|---|---|---|---|---|---|
| Replicate 1 | 10620.61 | 9407.96 | 8905.02 | 11148.72 | 10020.58 |
| Replicate 2 | 10451.87 | 10683.08 | 11029.04 | 10561.05 | 10681.26 |
| Replicate 3 | 10432.16 | 10691.1 | 10686.19 | 11870.08 | 10919.88 |
| MEAN | 10501.55 | 10260.71 | 10206.75 | 11193.28 | 10540.57 |
| STDEV | 103.58 | 738.52 | 1140.29 | 655.65 | 659.51 |
| % CV | 0.99% | 7.20% | 11.17% | 5.86% | 6.30% |
| % Recovery | 87.51% | 85.51% | 85.06% | 93.28% | 87.84% |

| Lipemic | Baseline | Beta Pool Slight | Amyloid 42 5 Moderate | Gross | pg/mL Total |
|---|---|---|---|---|---|
| Replicate 1 | 15585.98 | 15188.42 | 15258.95 | 15313.05 | 15336.60 |
| Replicate 2 | 14627.03 | 16766.84 | 14630.3 | 15586.4 | 15402.64 |
| Replicate 3 | 14494.58 | 13756.62 | 17081.41 | 15074.36 | 15101.74 |
| MEAN | 14902.53 | 15237.29 | 15656.89 | 15324.60 | 15280.33 |
| STDEV | 595.58 | 1505.71 | 1273.09 | 256.22 | 907.65 |
| % CV | 4.00% | 9.88% | 8.13% | 1.67% | 5.92% |
| % Recovery | 106.45% | 108.84% | 111.83% | 109.46% | 109.15% |

| Lipemic | Baseline | Beta Pool Slight | Amyloid 42 6 Moderate | 16000 Gross | pg/mL Total |
|---|---|---|---|---|---|
| Replicate 1 | 14926.96 | 14530.24 | 16083.97 | 13096.47 | 14659.41 |
| Replicate 2 | 17968.9 | 14741.02 | 14978.74 | 12618.86 | 15076.88 |
| Replicate 3 | 14277.43 | 16397.86 | 14946.5 | 13619.23 | 14810.26 |
| MEAN | 15724.43 | 15223.04 | 15336.40 | 13111.52 | 14848.85 |
| STDEV | 1970.71 | 1022.87 | 647.61 | 500.35 | 1035.39 |
| % CV | 12.53% | 6.72% | 4.22% | 3.82% | 6.82% |
| % Recovery | 98.28% | 95.14% | 95.85% | 81.95% | 92.81% |

Bilirubin Interference: Six spiked pools were analyzed in triplicate for a baseline, slight, moderate and gross icteric interference.

Beta Amyloid 40 and Beta Amyloid 42 are acceptable for non-icteric and slightly icteric cerebrospinal fluid samples.

| Icteric | Baseline | Beta Pool Slight | Amyloid 42 1 Moderate | 2000 Gross | pg/mL Total |
|---|---|---|---|---|---|
| Replicate 1 | 1488.32 | 1620.2 | 1654.67 | 1631.02 | 1598.55 |
| Replicate 2 | 1910.86 | 1730.53 | 1531.75 | 1433.03 | 1651.54 |
| Replicate 3 | 1883.89 | 1992.47 | 1675.22 | 1325.76 | 1719.34 |
| MEAN | 1761.02 | 1781.07 | 1620.55 | 1463.27 | 1656.48 |
| STDEV | 236.55 | 191.21 | 77.58 | 154.86 | 165.05 |
| % CV | 13.43% | 10.74% | 4.79% | 10.58% | 9.88% |
| % Recovery | 88.05% | 89.05% | 81.03% | 73.16% | 82.82% |

| Icteric | Baseline | Beta Pool Slight | Amyloid 40 1 Moderate | 2000 Gross | pg/mL Total |
|---|---|---|---|---|---|
| Replicate 1 | 2028.09 | 1870.09 | 1943.1 | 2162.25 | 2000.88 |
| Replicate 2 | 2065.04 | 1909.07 | 2169.68 | 2054.9 | 2049.67 |
| Replicate 3 | 1916.17 | 2030.58 | 2128.03 | 2144.2 | 2054.75 |
| MEAN | 2003.10 | 1936.58 | 2080.27 | 2120.45 | 2035.10 |
| STDEV | 77.52 | 83.71 | 120.60 | 57.48 | 84.83 |
| % CV | 3.87% | 4.32% | 5.80% | 2.71% | 4.18% |
| % Recovery | 100.16% | 96.83% | 104.01% | 106.02% | 101.76% |

| Icteric | Baseline | Beta Pool Slight | Amyloid 40 2 Moderate | 4000 Gross | pg/mL Total |
|---|---|---|---|---|---|
| Replicate 1 | 4386.17 | 3259.78 | 3670.62 | 4098.44 | 3853.75 |
| Replicate 2 | 3931.17 | 3534.09 | 3998.32 | 4156.48 | 3905.02 |
| Replicate 3 | 4190.26 | 3432.95 | 3857.11 | 4144.8 | 3906.28 |
| MEAN | 4169.20 | 3408.94 | 3842.02 | 4133.24 | 3888.35 |
| STDEV | 228.23 | 138.72 | 164.37 | 30.70 | 140.51 |
| % CV | 5.47% | 4.07% | 4.28% | 0.74% | 3.64% |
| % Recovery | 104.23% | 85.22% | 96.05% | 103.33% | 97.21% |

| Icteric | Baseline | Beta Pool Slight | Amyloid 40 3 Moderate | 6000 Gross | pg/mL Total |
|---|---|---|---|---|---|
| Replicate 1 | 6020.23 | 5940.6 | 6532.72 | 5627.95 | 6030.38 |
| Replicate 2 | 6100.69 | 6203.06 | 6753.67 | 6142.42 | 6299.96 |
| Replicate 3 | 5896.99 | 7228.16 | 6686.13 | 5976.64 | 6446.98 |
| MEAN | 6005.97 | 6457.27 | 6657.51 | 5915.67 | 6259.11 |
| STDEV | 102.60 | 680.38 | 113.22 | 262.60 | 289.70 |
| % CV | 1.71% | 10.54% | 1.70% | 4.44% | 4.60% |
| % Recovery | 100.10% | 107.62% | 110.96% | 98.59% | 104.32% |

| Icteric | Baseline | Beta Pool Slight | Amyloid 40 4 Moderate | 12000 Gross | pg/mL Total |
|---|---|---|---|---|---|
| Replicate 1 | 12495.31 | 11656.12 | 11097.61 | 9822.68 | 11267.93 |
| Replicate 2 | 12830.89 | 11106.69 | 10397.3 | 9836.78 | 11042.92 |
| Replicate 3 | 11888.74 | 12262.26 | 11055.11 | 11149.72 | 11588.96 |
| MEAN | 12404.98 | 11675.02 | 10850.01 | 10269.73 | 11299.93 |
| STDEV | 477.53 | 578.02 | 392.63 | 762.03 | 552.58 |
| % CV | 3.85% | 4.95% | 3.62% | 7.42% | 4.96% |
| % Recovery | 103.37% | 97.29% | 90.42% | 85.58% | 94.17% |

| Icteric | Baseline | Beta Pool Slight | Amyloid 40 5 Moderate | 14000 Gross | pg/mL Total |
|---|---|---|---|---|---|
| Replicate 1 | 11830.45 | 15117.44 | 13241.28 | 14397.76 | 13646.73 |
| Replicate 2 | 12060.76 | 15861.95 | 12366.55 | 15603.39 | 13973.16 |
| Replicate 3 | 12207.86 | 13692.37 | 14664.53 | 16441.16 | 14251.48 |
| MEAN | 12033.02 | 14890.59 | 13424.12 | 15480.77 | 13957.13 |
| STDEV | 190.23 | 1102.44 | 1159.85 | 1027.20 | 869.93 |
| % CV | 1.58% | 7.40% | 8.64% | 6.64% | 6.06% |
| % Recovery | 85.95% | 106.36% | 95.89% | 110.58% | 99.69% |

| Icteric | Baseline | Beta Pool Slight | Amyloid 40 6 Moderate | 16000 Gross | pg/mL Total |
|---|---|---|---|---|---|
| Replicate 1 | 16532.34 | 12984.53 | 14162.06 | 17720.56 | 15349.87 |
| Replicate 2 | 14859.48 | 13685.93 | 16447.31 | 17366.89 | 15589.90 |
| Replicate 3 | 14600.09 | 15161.21 | 16017.61 | 16461.9 | 15560.20 |
| MEAN | 15330.64 | 13943.89 | 15542.33 | 17183.12 | 15499.99 |
| STDEV | 1048.76 | 1111.03 | 1214.50 | 649.14 | 1005.86 |

| | | | | | |
|---|---|---|---|---|---|
| % CV | 6.84% | 7.97% | 7.81% | 3.78% | 6.60% |
| % Recovery | 95.82% | 87.15% | 97.14% | 107.39% | 96.87% |

| Icteric | Baseline | Beta Pool Slight | Amyloid 42 1 Moderate | 2000 Gross | pg/mL Total |
|---|---|---|---|---|---|
| Replicate 1 | 1488.32 | 1620.2 | 1654.67 | 1631.02 | 1598.55 |
| Replicate 2 | 1910.86 | 1730.53 | 1531.75 | 1433.03 | 1651.54 |
| Replicate 3 | 1883.89 | 1992.47 | 1675.22 | 1325.76 | 1719.34 |
| MEAN | 1761.02 | 1781.07 | 1620.55 | 1463.27 | 1656.48 |
| STDEV | 236.55 | 191.21 | 77.58 | 154.86 | 165.05 |
| % CV | 13.43% | 10.74% | 4.79% | 10.58% | 9.88% |
| % Recovery | 88.05% | 89.05% | 81.03% | 73.16% | 82.82% |

| Icteric | Baseline | Beta Pool Slight | Amyloid 42 2 Moderate | 4000 Gross | pg/mL Total |
|---|---|---|---|---|---|
| Replicate 1 | 3222.05 | 3732.25 | 3145.28 | 2994.84 | 3273.61 |
| Replicate 2 | 3497.19 | 3341.18 | 3648.74 | 3014.42 | 3375.38 |
| Replicate 3 | 3611.9 | 3832.09 | 3394.39 | 2847.73 | 3421.53 |
| MEAN | 3443.71 | 3635.17 | 3396.14 | 2952.33 | 3356.84 |
| STDEV | 200.35 | 259.45 | 251.73 | 91.11 | 200.66 |
| % CV | 5.82% | 7.14% | 7.41% | 3.09% | 5.86% |
| % Recovery | 86.09% | 90.88% | 84.90% | 73.81% | 83.92% |

| Icteric | Baseline | Beta Pool Slight | Amyloid 42 3 Moderate | 6000 Gross | pg/mL Total |
|---|---|---|---|---|---|
| Replicate 1 | 5144.23 | 4728.27 | 4239.65 | 3822.39 | 4483.64 |
| Replicate 2 | 5114.94 | 5040.95 | 4875.55 | 3903.05 | 4733.62 |
| Replicate 3 | 4701.39 | 4930.46 | 4063.35 | 3774.87 | 4367.52 |
| MEAN | 4986.85 | 4899.89 | 4392.85 | 3833.44 | 4528.26 |
| STDEV | 247.65 | 158.57 | 427.22 | 64.80 | 224.56 |
| % CV | 4.97% | 3.24% | 9.73% | 1.69% | 4.90% |
| % Recovery | 83.11% | 81.66% | 73.21% | 63.89% | 75.47% |

| Icteric | Baseline | Beta Pool Slight | Amyloid 42 4 Moderate | 12000 Gross | pg/mL Total |
|---|---|---|---|---|---|
| Replicate 1 | 10827.22 | 10391.44 | 10703.95 | 12734.98 | 11164.40 |
| Replicate 2 | 10500.06 | 9871.15 | 11285.4 | 10390.82 | 10511.86 |
| Replicate 3 | 10391.44 | 10156.67 | 10308.04 | 14883.95 | 11435.03 |
| MEAN | 10572.91 | 10139.75 | 10765.80 | 12669.92 | 11037.09 |
| STDEV | 226.84 | 260.56 | 491.61 | 2247.27 | 806.57 |
| % CV | 2.15% | 2.57% | 4.57% | 17.74% | 6.75% |
| % Recovery | 88.11% | 84.50% | 89.71% | 105.58% | 91.98% |

| Icteric | Baseline | Beta Pool Slight | Amyloid 42 5 Moderate | 14000 Gross | pg/mL Total |
|---|---|---|---|---|---|
| Replicate 1 | 14597.66 | 15694.71 | 16331.02 | 16887.67 | 15877.77 |
| Replicate 2 | 14635.85 | 15134.01 | 16958.66 | 15572.34 | 15575.22 |
| Replicate 3 | 14213.69 | 16612.21 | 20720.11 | 16993.48 | 17134.87 |
| MEAN | 14482.40 | 15813.64 | 18003.26 | 16484.50 | 16195.95 |
| STDEV | 233.49 | 746.24 | 2373.69 | 791.72 | 1036.29 |
| % CV | 1.61% | 4.72% | 13.18% | 4.80% | 6.08% |
| % Recovery | 103.45% | 112.95% | 128.59% | 117.75% | 115.69% |

| Icteric | Baseline | Beta Pool Slight | Amyloid 42 6 Moderate | 16000 Gross | pg/mL Total |
|---|---|---|---|---|---|
| Replicate 1 | 14827.94 | 16055.37 | 16949.58 | 20372.18 | 17051.27 |
| Replicate 2 | 17956.96 | 18569.81 | 16515.45 | 18956.15 | 17999.59 |
| Replicate 3 | 20671.44 | 19288.36 | 17146.77 | 18702.2 | 18952.19 |
| MEAN | 17818.78 | 17971.18 | 16870.60 | 19343.51 | 18001.02 |
| STDEV | 2924.20 | 1697.59 | 322.99 | 899.86 | 1461.16 |
| % CV | 16.41% | 9.45% | 1.91% | 4.65% | 8.11% |
| % Recovery | 111.37% | 112.32% | 105.44% | 120.90% | 112.51% |

Example 11: Ion Suppression

Ten patient samples were extracted.

The acquisition window was opened up to 10 minutes to monitor ion suppression across the gradient. The ten samples were injected through the analytical column while the digested peptide mix of beta amyloid 40 and 42 were infused post-column If the total ion chromatogram (TIC) of AB40 or AB42 showed a decrease of ≥15% of signal intensity when the internal standards for AB40 or AB42 eluted then ion suppression would be determined to be present in the assay.

The TIC of the digested peptides of AB40 and 42 showed no suppression in the gradient when the analyte is eluting. The TIC signal intensity is a flat line and shows ≤15% difference in signal intensity which is within the acceptable parameters of the assay.

Example 12: Carryover

High calibrator standards analyzed followed by four matrix blanks, this sequence was repeated another two times. The mean calculated concentration of the matrix blanks after the high calibrator yields a % Recovery of 0.06% for both Beta Amyloid 40 and 42.

There is no carryover observed for this assay.

| pg/mL | AB 42 | AB 40 |
|---|---|---|
| High_std_1 | 24114.04 | 30552.94 |
| High_std_2 | 21837.25 | 27101.48 |
| High_std_3 | 23955.83 | 26691.95 |
| High_std_4 | 24661.76 | 26510.1 |
| Blank_1 | 3.20 | 22.85 |
| Blank_2 | 0.05 | 16.97 |
| Blank_3 | 15.31 | 14.62 |
| Blank_4 | 19.34 | 37.13 |
| High_std_5 | 23467.62 | 29809.18 |
| High_std_6 | 21763.07 | 26340.7 |
| High_std_7 | 21486.03 | 26665.22 |
| High_std_8 | 22325.03 | 26431.58 |
| Blank_5 | 11.10 | −1.1 |
| Blank_6 | 5.28 | 50.1 |
| Blank_7 | 15.80 | 9.81 |
| High_std_18 | 23019.97 | 25465.63 |
| High_std_19 | 19756.77 | 24195.08 |
| High_std_20 | 26221.01 | 26983.93 |
| High_std_21 | 26237.81 | 27483.79 |
| Blank_15 | 14.56 | 14.64 |
| Blank_16 | 12.74 | 10.31 |
| Blank_17 | 19.97 | 5.05 |
| Blank_18 | 25.07 | 1.96 |

| | Blank | High Standard | % Recovery |
|---|---|---|---|
| AB42 | | | |
| Mean Calculated Value | 12.95 | 23237.18 | 0.06% |
| Mean Standard Deviation | 7.60 | 1941.57 | |
| AB40 | | | |
| Mean Calculated Value | 16.58 | 27019.30 | 0.06% |
| Mean Standard Deviation | 15.29 | 1710.44 | |

Example 13: Reference Interval (RI)

Beta Amyloid 40: 6000.00-15000.00 pg/mL
Beta Amyloid 42: 700.00-4000.00 pg/mL

Example 14 Alzheimer's Patient Data

Figure 8:
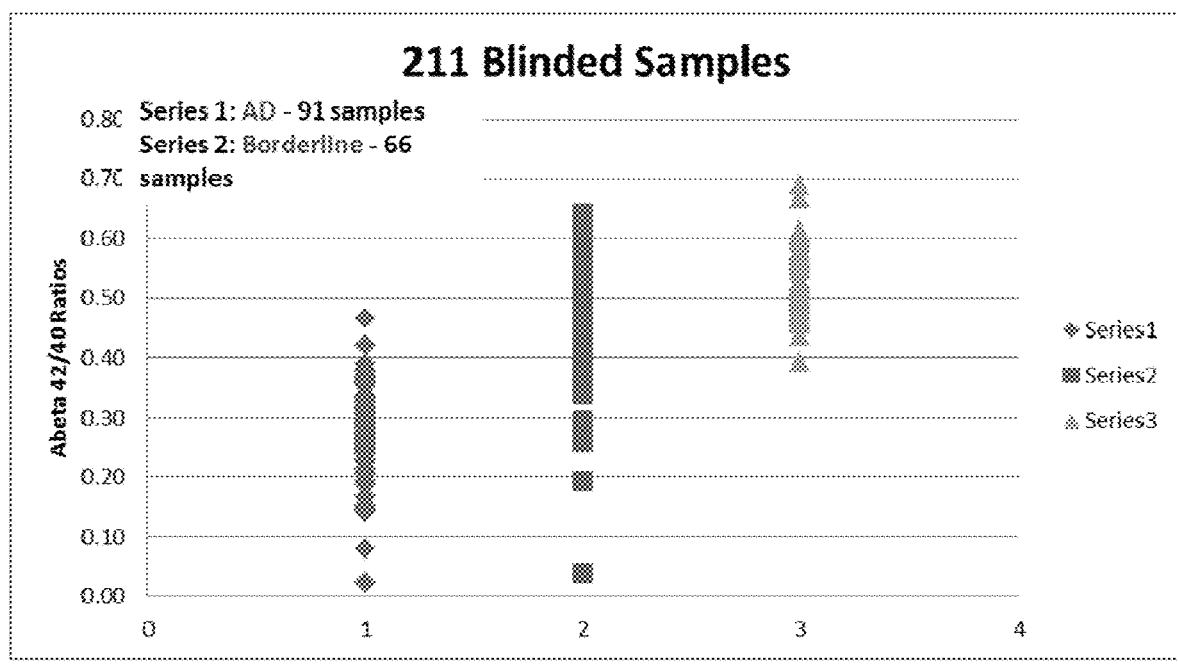
FIG. 8 shows the ratio of Aβ42:Aβ40 in 211 subjects comprising 91 Alzheimer's patients, 66 borderline Alzheimer's patients, and normal subjects.
Figure 9:
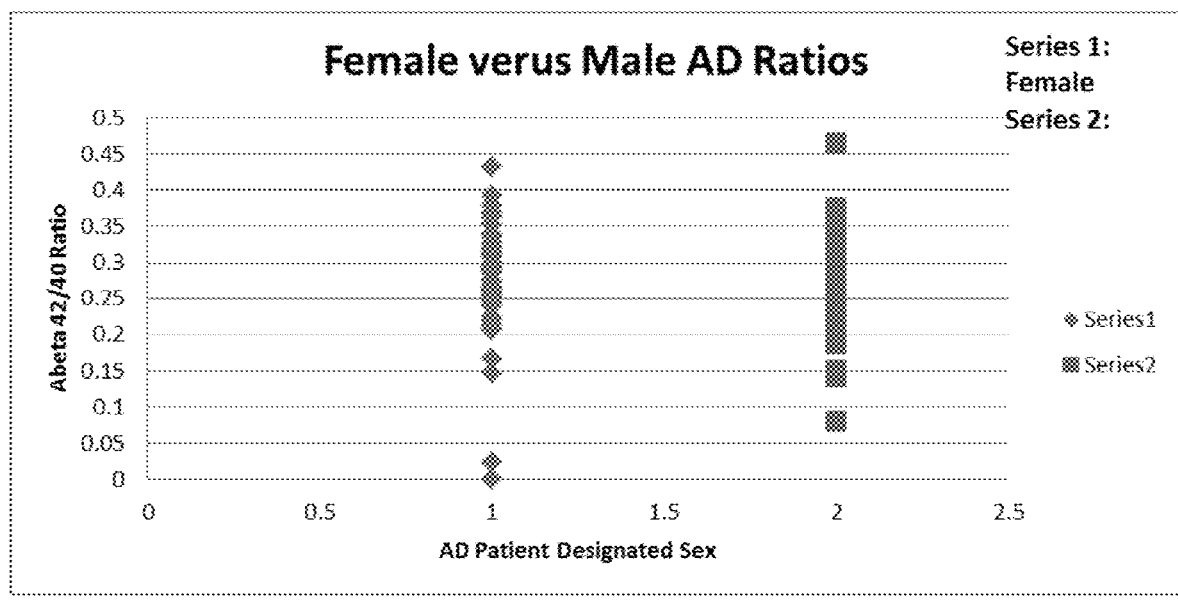
FIG. 9 shows the ratio of Aβ42:Aβ40 in female vs. male Alzheimer's patients.
Figure 10:
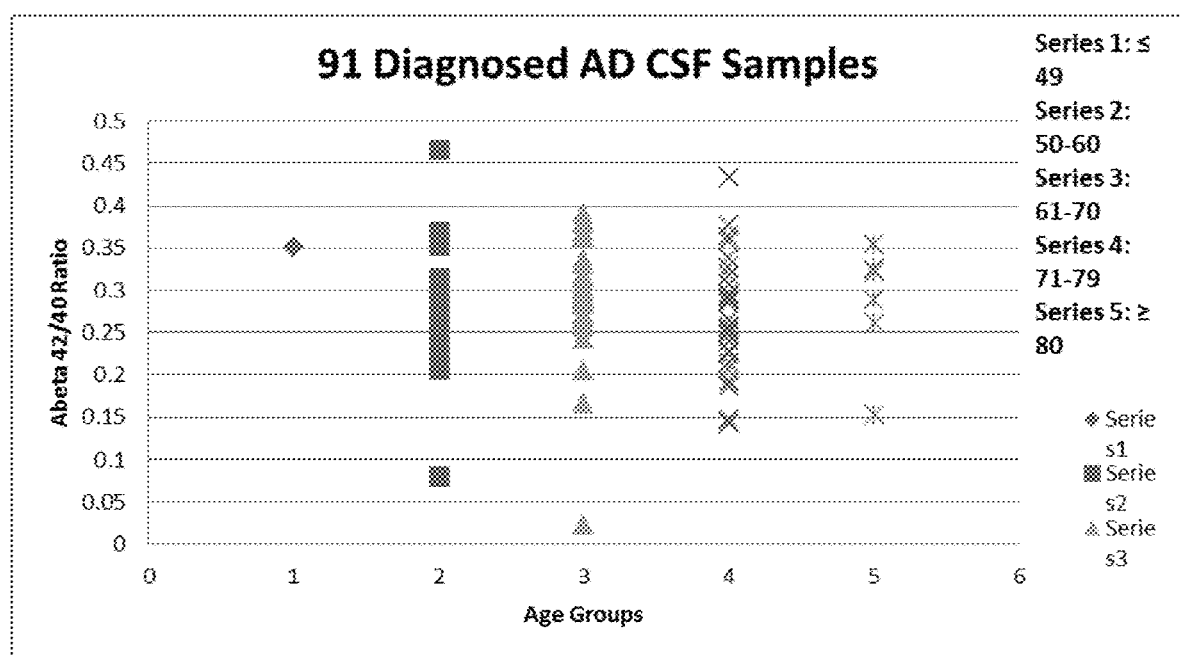
FIG. 10 shows the ratio of Aβ42:Aβ40 in age stratified groups of Alzheimer's patients.

Cerebrospinal fluids (CSF) of 211 subjects, which include patients diagnosed with Alzheimer's disease and normal subjects, were analyzed. FIGS. 8-10.

Aβ40 and Aβ42 were detected in all CSF samples. Surprisingly, Aβ42 levels were about 10 times higher than what has been published. Majority of patient samples were in the range of 1 to 8 ng/mL Alzheimer's patients were distinguishable based on the low ratio of Aβ42:Aβ40, as compared to the borderline patients and normal subjects (highest ratio). FIG. 8.

Example 15: Additional Recovery Study

Sample Preparation: All plastic disposables were pretreated, and Aβ standards were stabilized to prevent non-specific binding and to enhance long-term storage stability.

A strong protein denaturant was added to human CSF (500 uL), and samples underwent a protein digestion followed by solid-phase extraction. Samples were processed on a robotic liquid handler (Hamilton Microlab Star A857) in conjunction with a CEREX IP8 (SPEware) solid-phase extraction manifold.

Separation: HPLC separation was performed on an Aria TLX-4 System (Thermo Scientific) using a Waters XBridge Protein BEH C4 Column, 4.6×100 mm, 3.5 micron 300 Å

Detection: Thermo TSQ Quantiva Triple Quadrupole Mass Spectrometer

Linearity data show an $R^2$ value of at least 0.98 for both peptides, with a % CV of ≤15% across 8 calibrator standards.

The limit of quantitation was 100 pg/mL for both peptides.

Assay precision (% CV) was ≤15%, with a recovery range of 84% to 112% for Aβ40 and Aβ42.

Intra-assay (N=10) and Inter-assay (N=5, 5 days) Precision and Accuracy

| Peptide | Quality Control Level | Expected Concentration (pg/mL) | Intra-assay Mean (pg/mL) | Intra-assay Accuracy (%) | CV (%) | Inter-assay Mean (pg/mL) | Inter-assay Accuracy (%) | CV (%) |
|---|---|---|---|---|---|---|---|---|
| Aβ40 | Low | 750 | 643 | 86 | 14 | 800 | 107 | 15 |
|  | Med | 7,500 | 8,050 | 107 | 12 | 8,127 | 108 | 9 |
|  | High | 15,000 | 16,174 | 108 | 7 | 16,597 | 111 | 8 |
| Aβ42 | Low | 750 | 656 | 87 | 10 | 722 | 96 | 15 |
|  | Med | 7,500 | 7,363 | 98 | 6 | 6,997 | 93 | 6 |
|  | High | 15,000 | 14,614 | 97 | 4 | 14,836 | 99 | 8 |

Assay Stability Over 8 months

| Peptide | Quality Control Level | Expected Concentration (pg/mL) | October 2015 Measured (pg/mL) | October 2015 Accuracy (%) | December 2015 Measured (pg/mL) | December 2015 Accuracy (%) | June 2016 Measured (pg/mL) | June 2016 Accuracy (%) |
|---|---|---|---|---|---|---|---|---|
| Aβ40 | Low | 750 | 660 | 88 | 704 | 94 | 758 | 101 |
|  | Med | 7,500 | 6,891 | 92 | 7,608 | 101 | 6,987 | 93 |
|  | High | 15,000 | 12,656 | 84 | 15,426 | 103 | 14,055 | 94 |
| Aβ42 | Low | 750 | 704 | 94 | 820 | 109 | 815 | 109 |
|  | Med | 7,500 | 8,381 | 112 | 8,074 | 108 | 6,596 | 88 |
|  | High | 15,000 | 13,037 | 87 | 16,853 | 112 | 14,362 | 96 |

Stabilization of Aβ peptides was achieved, allowing for long-term storage of calibrator and quality control standards.

Frozen calibrators have been stable for at least 8 months when stored at −80° C.

Figure 12:
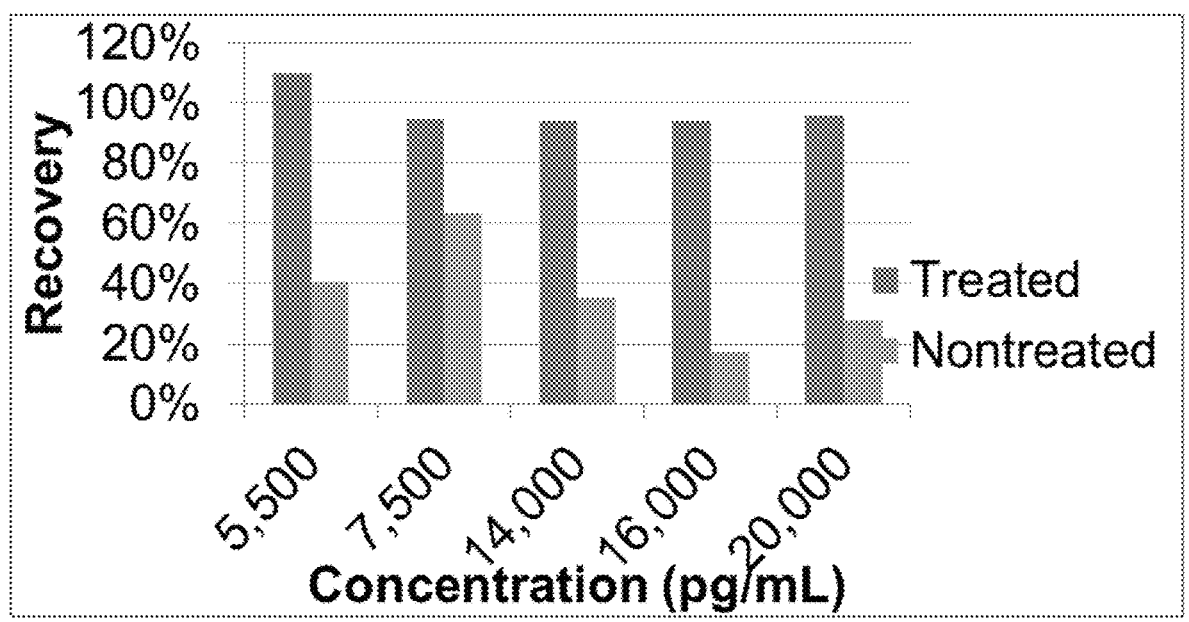
FIG. 12 shows recovery of Aβ40 from treated versus nontreated tubes.
Figure 13:
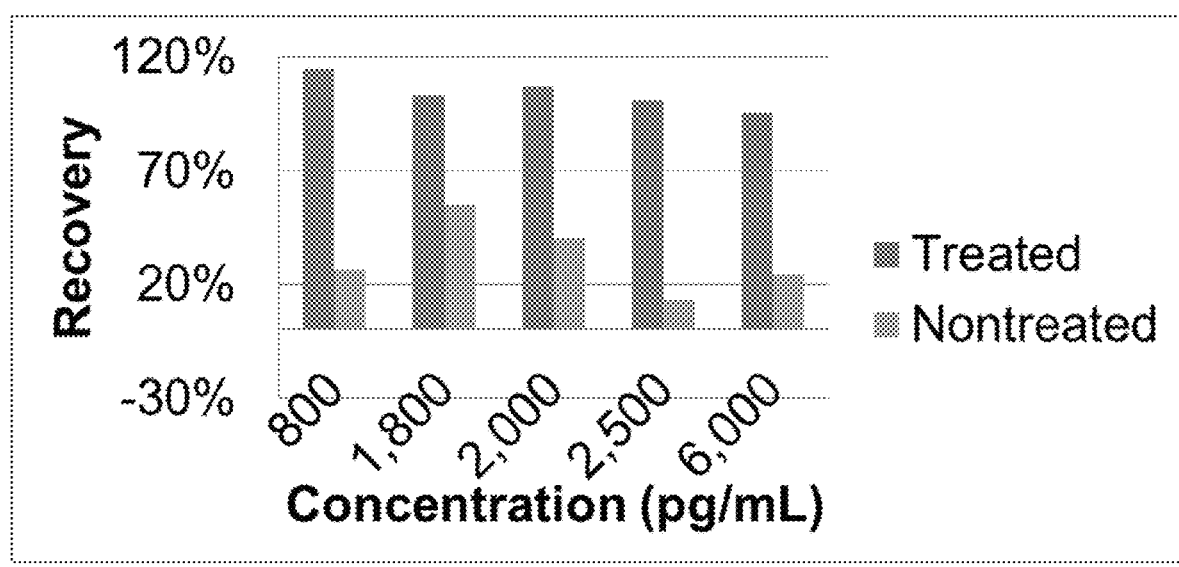
FIG. 13 shows recovery of Aβ42 from treated versus nontreated tubes.
Figure 14:
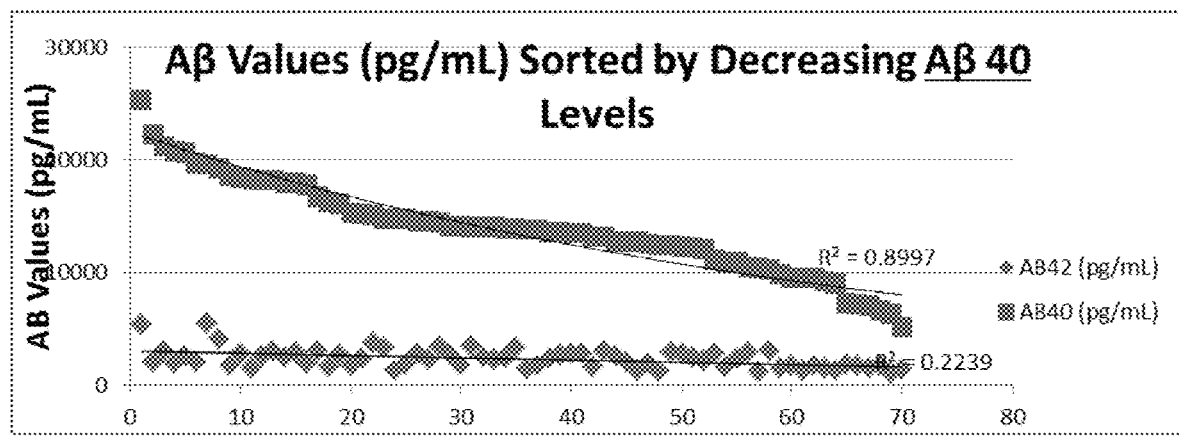
FIG. 14 shows patient Aβ values (μg/mL) sorted by decreasing Aβ40 levels.
Figure 15:
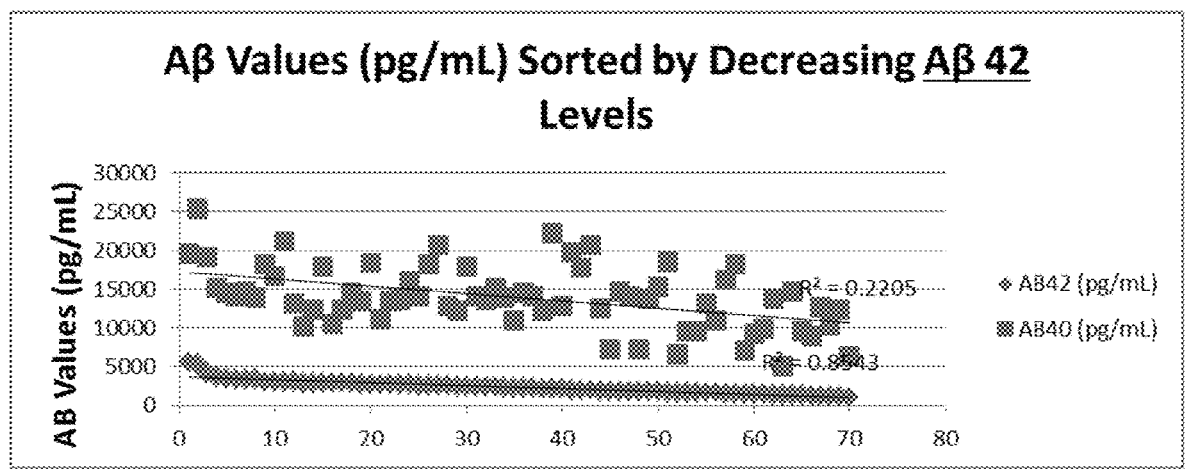
FIG. 15 shows patient Aβ values (μg/mL) sorted by decreasing Aβ42 levels.
Figure 16:
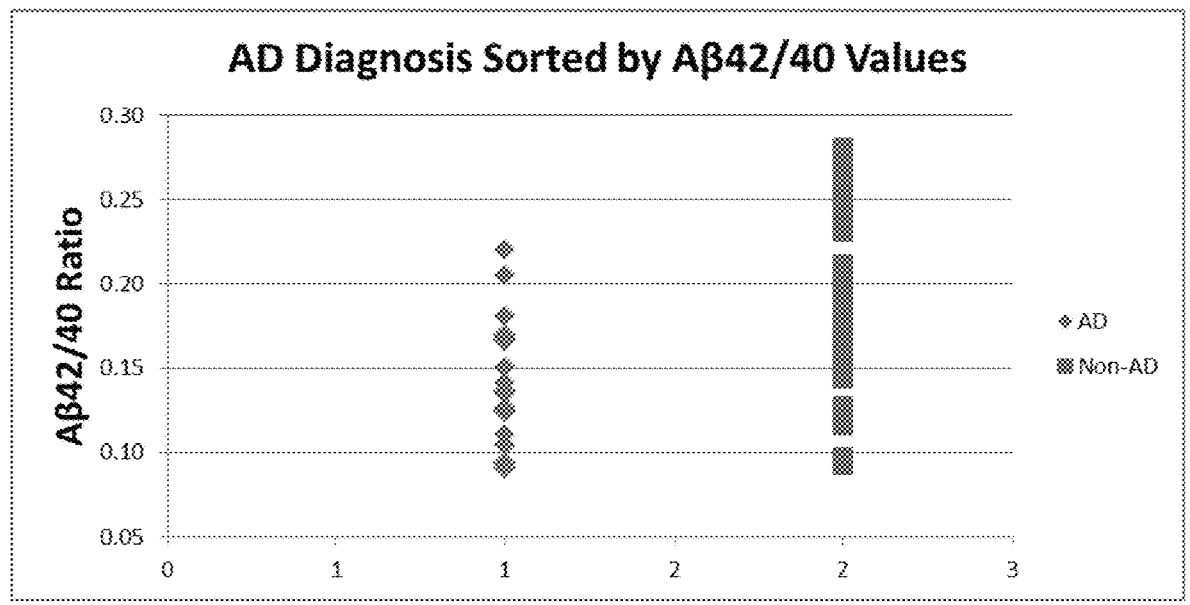
FIG. 16 shows patient Alzheimer's Disease diagnosis sorted by Aβ42/Aβ40 values.
Figure 17:
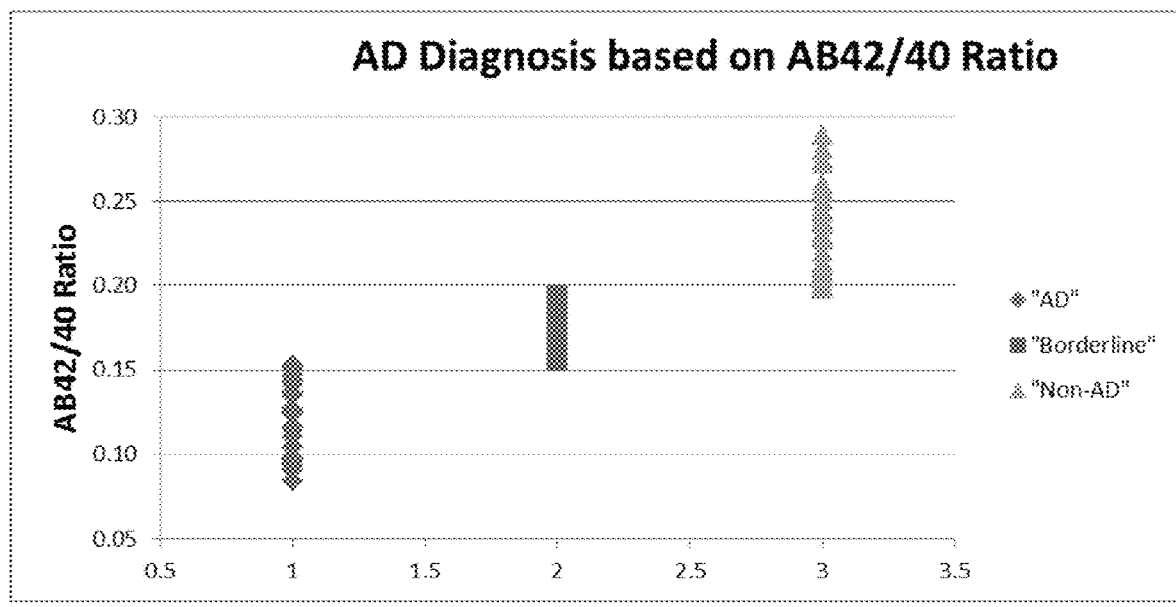
FIG. 17 shows patient Alzheimer's Disease diagnosis based on Aβ42/Aβ40 ratio.

Stabilization measures eliminated nonspecific binding and yielded a higher analyte recovery. FIGS. 12 and 13.

Values for patient CSF Aβ42 concentrations were higher using the LC-MS/MS assay than those using ELISA assays. This is consistent with previous reports comparing the 2 methodolgies. Future work will determine if the pre-analytical factors described herein might help explain the discrepancy.

| Patient | LC-MS/MS (pg/mL) | ELISA (pg/mL) |
|---|---|---|
| 1 | 1,668 | 536 |
| 2 | 1,617 | 534 |
| 3 | 2,808 | 624 |
| 4 | 3,184 | 850 |
| 5 | 4,061 | 913 |
| 6 | 2,142 | 672 |
| 7 | 1,878 | 627 |
| 8 | 2,829 | 566 |
| 9 | 1,882 | 633 |
| 10 | 1,634 | 614 |
| 11 | 2,706 | 644 |
| 12 | 773 | 466 |
| 13 | 1,801 | 602 |
| 14 | 3,891 | 739 |
| 15 | 1,524 | 671 |
| 16 | 2,300 | 605 |
| 17 | 1,167 | 458 |
| 18 | 1,842 | 625 |
| 19 | 2,431 | 665 |
| 20 | 2,814 | 938 |

Conclusion: This novel approach eliminated one of the main challenges in quantitating Aβ40 and Aβ42: poor reproducibility caused by nonspecific binding.

Example 16: Patient Diagnostic Study

Three quality controls (low, medium, high) were ran representing three distinct points along the calibration curve. QC's were ran at the beginning and end of the run to ensure accurate quantitation throughout the plate. Quality control accuracy is shown below:

| Abeta 40 | Expected (pg/mL) | Calculated (pg/mL) | % Accuracy |
|---|---|---|---|
| Front: Low QC | 750 | 743.28 | 99.10% |
| Front: Medium QC | 7500 | 6724.33 | 89.66% |
| Front: High QC | 15000 | 13554.62 | 90.36% |
| Back: Low QC | 750 | 754.58 | 100.61% |
| Back: Medium QC | 7500 | 7351.87 | 98.02% |
| Back: High QC | 15000 | 13911.65 | 92.74% |

| Abeta 42 | Expected (pg/mL) | Calculated (pg/mL) | % Accuracy |
|---|---|---|---|
| Front: Low QC | 750 | 815.71 | 108.76% |
| Front: Medium QC | 7500 | 6930.69 | 92.41% |
| Front: High QC | 15000 | 13976.57 | 93.18% |
| Back: Low QC | 750 | 667.22 | 88.96% |
| Back: Medium QC | 7500 | 6341.3 | 84.55% |
| Back: High QC | 15000 | 13384.45 | 89.23% |

Aβ40 and 42 Patient Samples Ranges

Based off of 72 patient samples

Aβ40: 5135.33-25348.94 pg/mL

Aβ42: 1068.00-5499.76 pg/mL

Normalize varying levels of Aβ40 and 42.

As Aβ42 values decrease due to plaqueing or insufficient clearance, the ratio of Aβ42/40 also decreases.

Aβ40 and 42 levels appear to increase/decrease independent of one another.

Data was sorted by Aβ42/40 ratio and split into two sets based of off the median (Aβ42/40=0.17)

Half of the data into <Aβ42/40 Median

Half of the data into >Aβ42/40 Median

Mean, standard deviation, and % CV was calculated:

For ratio values <Aβ42/40 Median, values ≥1SD were removed

For ratio values >Aβ42/40 Median, values ≤1SD were removed

1SD outliers were placed into a "Borderline" category

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of amyloid beta 40 (Aβ40) and amyloid beta 42 (Aβ42) in a sample, said method comprising:
   (a) digesting amyloid beta in the sample to generate Aβ40 comprising the sequence GAIIGLMVGGVV (SEQ ID NO:2) and Aβ42 comprising the sequence GAIIGLMVGGVVIA (SEQ ID NO:4);
   (b) purifying Aβ40 and Aβ42 in the sample;
   (b) ionizing Aβ40 and Aβ42 in the sample to produce one or more precursor ions;
   (c) generating one or more fragment ions of Aβ40 and Aβ42; and
   (d) determining the amount of the one or more fragment ion(s) from step (d) by mass spectrometry, wherein the one or more fragment ions comprises an ion with a mass/charge ratio selected from the group consisting of 812.37±0.5, 869.4±0.5, 968.43±0.5, 869.39±0.5, 968.44±0.5, 1067.5±0.5, and 1180.57±0.5.

2. The method of claim 1, wherein said purifying comprises liquid chromatography.

3. The method of claim 2, wherein said liquid chromatography comprises high performance liquid chromatography (HPLC).

4. The method of claim 1, wherein said method further comprises a C-4 analytical column.

5. The method of claim 1, further comprising pretreating surfaces of equipment that come in contact with the sample with an agent that prevents amyloid beta from sticking to the surfaces.

6. The method of claim 5, wherein the agent is *E. coli* lysate.

7. The method of claim 1, further comprising incubating the sample with an agent that stabilizes amyloid beta.

8. The method of claim 7, wherein said agent comprises an antibody that binds to the C-terminus of amyloid beta, an antibody that binds to the N-terminus of amyloid beta, apolipoprotein E2, apolipoprotein E4, or a combination thereof.

9. The method of claim 7, wherein said agent confers stability through at least three freeze-thaw cycles.

10. The method of claim 7, wherein said agent confers stability for at least 2 months at −70° C.

11. The method of claim 1, wherein the method comprises a mixed mode anion exchange extraction.

12. The method of claim 1, wherein said ionization comprises heated electrospray ionization (HESI).

13. The method of claim 1, wherein said ionization comprises ionizing in positive mode.

14. The method of claim 1, wherein said generation of fragment ions comprises using collision energy of between 20V to 45V.

15. The method of claim 1, further comprising adding an internal standard.

16. The method of claim 15, wherein said internal standard is isotopically labeled.

17. The method of claim 16, wherein said internal standard comprises $^{13}C^{15}N$ labeling.

18. The method of claim 17, wherein the precursor ion of the internal standard has a mass/charge ratio of 1110.7±0.5.

19. The method of claim 17, wherein the one or more fragment ions of the internal standard has a mass/charge ratio of 768.48±0.5, 825.5±0.5, or 882.52±0.5.

20. The method of claim 1, wherein the limit of quantitation of the method is less than or equal to 10 ng/ml.

21. The method of claim 1, wherein said digestion comprises digesting with Lys C.

22. The method of claim 21, wherein said digestion further comprises adding urea.

23. The method of claim 22, wherein said digestion further comprises digestion in microwave.

24. The method of claim 1, wherein the Aβ40 and/or Aβ42 further comprise a winged peptide.

25. The method of claim 24, wherein the winged peptide is hydrophilic.

26. The method of claim 24, wherein the winged peptide comprises one or more N-terminal or C-terminal amino acid residues.

27. The method of claim 1, wherein the method comprises determining the ratio of Aβ42 to Aβ40.

* * * * *